US 7,153,916 B2
Dec. 26, 2006

(12) United States Patent
Tanabiki et al.

(10) Patent No.: US 7,153,916 B2
(45) Date of Patent: Dec. 26, 2006

(54) TRANSITION METAL COMPOUND, CATALYST FOR POLYMERIZATION OF OLEFIN, AND PROCESS FOR POLYMERIZATION OF OFELIN USING THE CATALYST

(75) Inventors: Masao Tanabiki, Yokkaichi (JP); Hideo Nagashima, Kasuga (JP)

(73) Assignee: Tosoh Corporation, Shinnanyo (JP)

( * ) Notice: Subject to any disclaimer, the term of this patent is extended or adjusted under 35 U.S.C. 154(b) by 154 days.

(21) Appl. No.: 10/094,799

(22) Filed: Mar. 12, 2002

(65) Prior Publication Data
US 2003/0018145 A1 Jan. 23, 2003

(30) Foreign Application Priority Data

Mar. 12, 2001 (JP) ............................. 2001-068371
Dec. 26, 2001 (JP) ............................. 2001-394289
Dec. 26, 2001 (JP) ............................. 2001-394290

(51) Int. Cl.
C08F 4/44 (2006.01)
B01J 31/38 (2006.01)

(52) U.S. Cl. ..................... 526/171; 526/172; 502/155; 502/157

(58) Field of Classification Search ................ 526/171, 526/172; 502/155, 167
See application file for complete search history.

(56) References Cited

U.S. PATENT DOCUMENTS 6,309,997 B1 * 10/2001 Fujita et al. ................ 502/167

FOREIGN PATENT DOCUMENTS

| JP | 2-261809 | 10/1990 |
|---|---|---|
| JP | 2001-106719 | 4/2001 |
| JP | 2001-240610 | 9/2001 |
| WO | WO 94/04141 | 3/1994 |
| WO | WO 96/23010 | 8/1996 |
| WO | WO 00/56781 | 9/2000 |
| WO | WO 01/30865 | 5/2001 |

OTHER PUBLICATIONS

Younkin et al., Science, vol. 287, pp. 460-462.*
Y. Ito, et al., Database Crossfire Beilstein Online, AN 8186527, XP-002198469, pp. 1-4, Feb. 26, 2000.
E. Carmona, et al., Database CA Online, AN 1990:217207, XP-002198470, pp. 1-4, "Multiple Insertion Reactions of Tert-Butyl Isocyanide into Nickel-Alkyl Bonds", 1990.
M. P. Bubnov, et al., Database CA Online, AN 1993:580992, XP-002198471, pp. 1-15, "ESR Investigation of Monosemiquinone Nickel Complexes in Solution", 1993.
S. Otsuka, et al., Database CA Online, AN 1973:418839, XP-002198472, pp. 1-8, "Chemistry of Alkoxycarbonyl, Acyl, and Alkyl Compounds of Nickel(II) and Palladium(II)", 1973.
K. Aoki, et al., Database CA Online, AN 1976:44311, XP-002198473, pp. 1-3, "Interactions of Isocyanide With Transition Metal Complexes. XII. Crystal and Molecular Structure of .PI.-", 1976.
M. J. Scott, et al., Organometallics, vol. 16, No. 26, XP-002198468, pp. 5857-5868, "Isocyanide Insertion Reactions With Organometallic Group 4 Tropocoronand Complexes: Formation of $\eta^2$-Iminoacyl, Enediamido, $\eta^2$-Imine, and $\mu$-Imido Products", 1997.
L. K. Johnson, et al., J. Am. Chem. Soc., vol. 117, No. 23, pp. 6414-6415, "New Pd(II)- and Ni(II)-Based Catalysts for Polymerization of Ethylene and $\alpha$-Olefins", 1995.
W. Keim, et al., Angew. Chem. Int. Ed. Engl., vol. 117, No. 6, pp. 466-467, "Novel Coordination of (Benzoylmethylene)Triphenylphosphorane in a Nickel Oligomerization Catalyst", 1978.
C. Wang, et al., Organometallics, vol. 17, No. 15, pp. 3149-3151. "Neutral Nickel(II)—Based Catalysts for Ethylene Polymerization", 1998.
T. R. Younkin, et al., Science, vol. 287, pp. 460-462, "Neutral, Single-Component Nickel (II) Polyolefin Catalysts That Tolerate Heteroatoms", Jan. 21, 2000.
F. A. Hicks, et al., Organometallics, vol. 20, No. 15, pp. 3216-3219, "A Highly Active Anilinotropone-Based Neutral Nickel(II) Catalyst for Ethylene Polymerization", 2001.
S. D. Ittel, et al., Chemical Reviews, vol. 100, No. 4, pp. 1169-1203, "Late-Metal Catalysts for Ethylene Homo- and Copolymerization", 2000.
W. H. Glaze, et al., Journal of the American Chemical Society, pp. 7196-7199, " $\sigma$-Alkyl or $\sigma$-Acyl Isocyanide Complexes of Nickel(II) and Palladium(II). Preparation and Successive Insertion Reactions", Dec. 3, 1969.
Y. Yamamoto, et al., Bull. Chem. Soc. Jpn., Short Communications, vol. 43, No. 8, p. 2653, "Single, Double and Triple Insertion of Cyclohexyl Isocyanide into Methyl-Paladium Sigma Bond", Aug. 1970.
Y. Yamamoto, et al., Inorganic Chemistry, vol. 11, No. 1, pp. 211-215, "Studies on Interactions of Isocyanides With Transition Metal Complexes. VIII. Reactions of Alkyl Isocyanide With Dicarbonyl-$\pi$Cyclopentadienylalkyliron", 1972.
P. M. Treichel, Organometallic Chemistry, vol. 11, pp. 22-86, "Transition Metal-Isocyanide Complexes".
J. Vicente, et al., Organometallics, vol. 21, No. 2, pp. 272-283, "Synthesis and Reactivity Toward Isonitriles of (2-Aminoaryl)Palladium(II) Complexes", 2002.
U.S. Appl. No. 10/022,772, filed Dec. 20, 2001, pending.
U.S. Appl. No. 10/094,799, filed Mar. 12, 2002, pending.

* cited by examiner

*Primary Examiner*—Robert D. Harlan
(74) *Attorney, Agent, or Firm*—Oblon, Spivak, McClelland, Maier & Neustadt, P.C.

(57) ABSTRACT

Catalyst for polymerization of an olefin is provided, which comprises (A) a transition metal compound having a carbon-metal bond structure and (B) an activating co-catalyst, or (A) a transition metal compound having a carbon-metal bond structure, (B) an activating cocatalyst and (C) an organometallic compound.

17 Claims, 2 Drawing Sheets

TRANSITION METAL COMPOUND, CATALYST FOR POLYMERIZATION OF OLEFIN, AND PROCESS FOR POLYMERIZATION OF OFELIN USING THE CATALYST

BACKGROUND OF THE INVENTION (1) Field of the Invention

This invention relates a transition metal compound, a catalyst for polymerization of an olefin comprising the transition metal compound, and a process for polymerizing an olefin using the catalyst.

(2) Description of the Related Art

As a catalyst for polymerization of an olefin, a metallocene catalyst comprising a combination of a complex having a cyclopentadienyl ring as a ligand with an aluminoxane attracts attention because the catalyst has a high catalytic activity, gives a polymer having a narrow molecular weight distribution and is capable of controlling the microstructure of the polymer. Such metallocene catalyst is proposed in, for example, Japanese Unexamined Patent Publication No. S58-19309.

In recent years, it has been reported that a catalyst comprising a late transition metal complex gives a polyolefin having a structure with many branches, which structure is distinguishable from that of a polymer produced with the conventional metallocene catalyst. Such complex includes, for example, a diimine complex disclosed in J. Am. Chem. Soc., 117, 6414 (1995) and WO96/23010; a salicylaldimine complex disclosed in Science, 287, 460 (2000) and WO00/56781; and an anilinotropone complex disclosed in Organometallics, 20, 3217 (2001) and WO01/30865.

SUMMARY OF THE INVENTION

A primary object of the present invention is to provide a novel transition metal compound, which is useful as an ingredient of a catalyst for polymerization of an olefin.

Another object of the present invention is to provide a catalyst for polymerization of an olefin, which enables the production of polyolefin with enhanced efficiency.

Still another object of the present, invention is to provide a process for polymerizing an olefin with enhanced efficiency.

In one aspect of the present invention, there are provided transition metal compounds represented by the following formulae (1), and (4) through (9).

Formula (1):

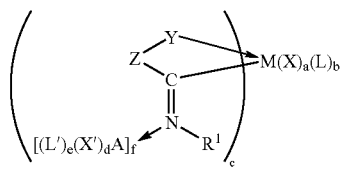

wherein $R^1$ represents a hydrogen atom, a hydrocarbon group having 1 to 30 carbon atoms, a substituted silyl group, a substituted armide group, a substituted alkoxy group, a substituted aryloxy group, or a hydrocarbon group containing a substituted silyl group, an atom of group 15 or group 16 of the periodic table or a halogen atom;

z represents a substituent selected from the group consisting of substituents represented by the following formulae (2):

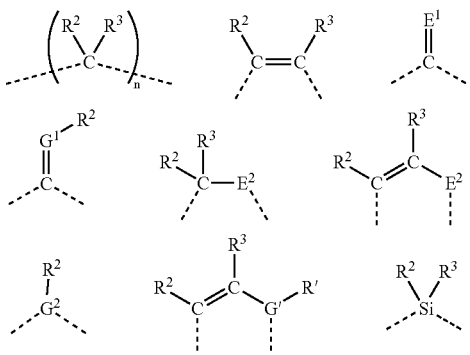

wherein $R'$, $R^2$ and $R^3$ independently represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, $R'$, $R^2$ and $R^3$ may be the same or different and two members selected from $R'$, $R^2$ and $R^3$ may be bonded together to form a ring, provided that at least two rings can be formed; $E^1$ and $E^2$ represent an atom of group 16 of the periodic table, $G'$, $G^1$ and $G^2$ represent an atom of group 15 of the periodic table, n is an integer of 0 to 2 provided that a case when n is 0 means that Y and the iminoacyl group in formula (1) are directly bonded to each other;

Y represents a substituent selected from the group consisting of substituents represented by the following formulae (3):

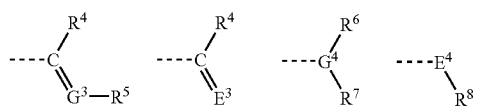

wherein $R^4$, $R^7$ and $R^8$ independently represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, $R^5$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, $R^6$ represents a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, $E^3$ and $E^4$ represent an atom of group 16 of the periodic table, $G^3$ and $G^4$ represent an atom of group 15 of the periodic table, $R^4$ and $R^5$ may be bonded together to form a ring, and $R^6$ and $R^7$ may be bonded together to form a ring;

two members selected from $R^1$, Z and Y may be bonded together to form a ring, provided that at least two rings can be formed;

A represents a transition metal atom of groups 3 to 11 of the periodic table or a typical element of groups 1, 2 and 11 to 16 of the periodic table;

X' represents a hydrogen atom, a hydrocarbon group having 1 to 20 carbon atoms, a substituted silyl group, a substituted amide group, a substituted alkoxy group, a substituted aryloxy group, a hydrocarbon group containing a substituted silyl group, or a hydrocarbon group containing an atom of group 15 or group 16 of the periodic table or a halogen atom, or X' is a halogen atom; and d is an integer of 0 to 6 and, when n is at least 2, X's may be the same or different;

L' is a coordinate bond-forming compound having a coordinating member selected from the group consisting of π electron, atoms of groups 14, 15 and 16 of the periodic table and halogen atoms, and e is an integer of 0 to 6 and, when e is at least 2, L's may be the same or different;

d is an oxidation number of the central metal A, and f is an integer of 0 or 1;

M represents a: transition metal atom of groups 3 to 11 of the periodic table;

X represents a hydrogen atom, a hydrocarbon group having 1 to 20 carbon atoms, a substituted silyl group, a substituted amide group, a substituted alkoxy group, a substituted aryloxy group, a hydrocarbon group containing a silyl group, or a hydrocarbon group containing an atom of group 15 or group 16 of the periodic table or a halogen atom, or X' is a halogen atom; and a is an integer of 1 to 5 and, when n is at least 2, Xs may be the same or different;

L is a coordinate bond-forming compound having a coordinating member selected from the group consisting of π electron, atoms of groups 14, 15 and 16 of the periodic table and halogen atoms, and b is an integer of 0 to 6 and, when b is at least 2, Ls may be the same or different; and X and L may be bonded to each other; L and $R^1$ may be bonded to each other, and L and Y may be bonded to each other; and c is an integer of 1 to 5 and the sum of a+c is an oxidation number of the central metal M.

Formula (4):

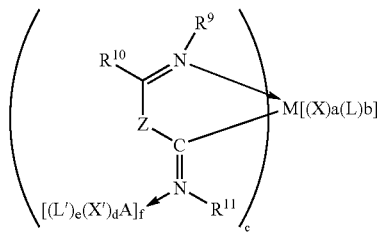

wherein $R^9$ and $R^{11}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom; $R^{10}$ in represents a hydrogen atom, a hydrocarbon group having 1 to 20 carbon atoms, a substituted silyl group, a substituted amide group, a substituted alkoxcy group, a substituted aryloxy group, or a hydrocarbon group containing a substituted silyl group, an atom of group 15 or group 16 of the periodic table or a halogen atom; Z, M, X, L, A, X', L', a, b, c, d, e and f are the same as Z, M, X, L, A, X', L', a, b, c, d, e and f, which are defined for formula (1); two members selected from $R^9$, $R^{10}$, $R^{11}$ and Z may be bonded to each other to form a ring, provided that at least two rings can be formed; X and L may be bonded to each other, L and $R^9$ may be bonded to each other, and L and $R^{11}$ may be bonded to each other.

Formula (5):

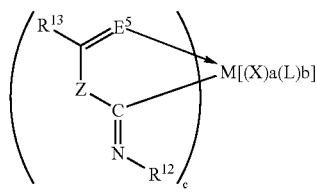

wherein $R^{12}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom; $R^{13}$ represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom; $E^5$ represents an atom of group 16 of the periodic table; Z, M, X, L, a, b and c are the same as Z, M, X, L, a, b and c, respectively, which are defined for formula (1); two members selected from $R^{12}$, $R^{13}$ and Z may be bonded to each other to form a ring, X and L may be bonded to each other, and L and $R^{12}$ may be bonded to each other.

Formula (6):

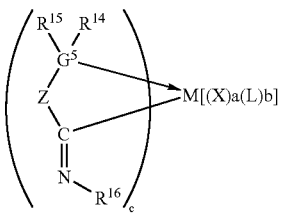

wherein $R^{14}$ and $R^{15}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, $R^{14}$ and $R^{15}$ may be the same or different, and $R^{14}$ and $R^{15}$ may be bonded together to form a ring; $R^{16}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom; $G^5$ represents an atom of group 15 of the periodic table; Z, M, X, L, a, b and c are the same as Z, M, X, L, a, b and c, respectively, which are defined for formula (1); two members selected from $R^{14}$, $R^{15}$, $R^{16}$ and Z may be bonded to each other to form a ring, provided that at least two rings can be formed; X and L may be bonded to each other, L and $R^{14}$ may be bonded to each other, L and $R^{15}$ may be bonded to each other, and L and $R^{16}$ may be bonded to each other.

Formula (7):

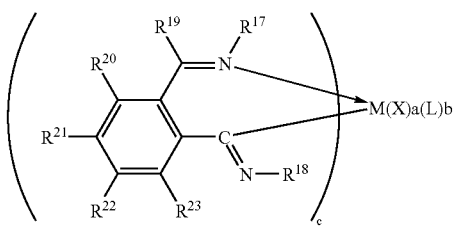

wherein $R^{17}$ and $R^{18}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, and $R^{17}$ and $R^{18}$ may be the same different; $R^{19}$ through $R^{23}$ represent a hydrogen atom, a halogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, $R^{19}$ through $R^{23}$ may be the same or different, and two members selected from $R^{17}$ through $R^{23}$ may be bonded together to form a ring, provided that at least two rings can be formed; M, X, L, a, b and c are the same as M, X, L, a, b and c, respectively, which are defined for formula (1); and X and L may be bonded to each other, L and $R^{17}$ may be bonded to each other, and L and $R^{18}$ may be bonded to each other.

Formula (8):

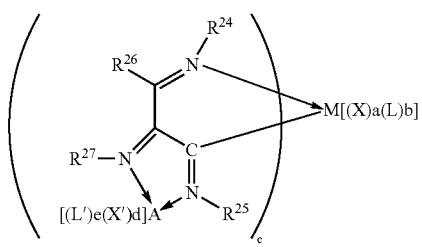

wherein $R^{24}$ through $R^{27}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom; and M, X, L, A, X', L', a, b, c, d and e are the same as M, X, L, A, X', L', a, b, c, d and e, respectively, which are defined for formula (1).

Formula (9):

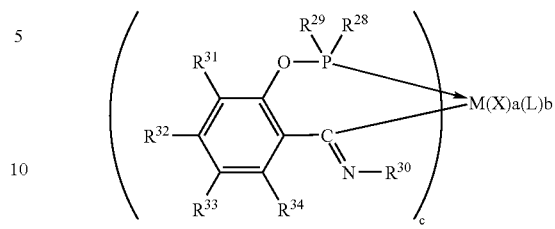

wherein $R^{28}$, $R^{29}$ and $R^{31}$ through $R^{34}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom; $R^{30}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, M, X, L, a, b and c are the same as M, X, L, a, b and c, respectively, which are defined for formula (1); and X and L may be bonded to each other, L and $R^{28}$ may be bonded to each other, L and $R^{29}$ may be bonded to each other, and L and $R^{30}$ may be bonded to each other.

In another aspect of the present invention, there is provided a catalyst for polymerization of an olefin, which comprises (A) a transition metal compound as represented by any one of formulae (1), and (4) through (9), and (B) an activating cocatalyst.

In still another aspect of the present invention, there is provided a catalyst for polymerization of an olefin, which comprises (A) a transition metal compound as represented by any one of the following general formulae (10) to (14), and (B) an activating cocatalyst.

Formula (10):

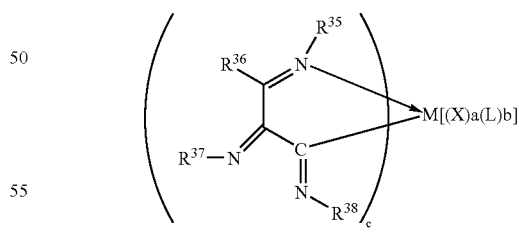

wherein $R^{35}$ through $R^{38}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom; and M, X, L, a, b and c are the same as M, X, L, a, b and c, respectively, which are defined for formula (1).

Formula (11):

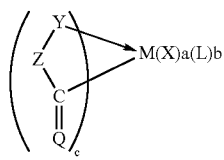

wherein Q represents an element of group 16 of the periodic table or $C(R^{39})(R^{40})$ wherein $R^{39}$ and $R^{40}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom;

Z, Y, M, X, L, a, b and c are the same as Z, Y, M, X, L, a, b and c, respectively, which are defined for formula (1); and two members selected from Q, Z and Y may be bonded together to form a ring, provided that at least two rings can be formed; X and L may be bonded to each other, and L and Y may be bonded to each other.

Formula (12):

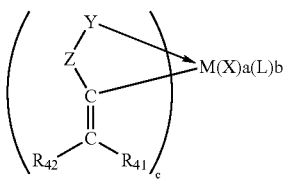

wherein $R^{41}$ and $R^{42}$ represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom, and $R^{41}$ and $R^{42}$ may be the same or different;

Z, Y, M, X, L, a, b and c are the same as Z, Y, M, X, L, a, b and c, respectively, which are defined for formula (1); sand two members selected from $R^{41}$, $R^{42}$, Z and Y may be bonded together to form a ring, X and L may be bonded to each other, L and $R^{41}$ may be bonded to each other, L and $R^{42}$ may be bonded to each other, and L and Y may be bonded together.

Formula (13):

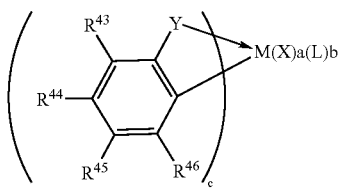

wherein $R^{43}$ through $R^{46}$ represent a hydrogen atom, a hydrocarbon group having 1 to 20 carbon atoms, a substituted silyl group, a substituted amide group, a substituted alkoxy group, a substituted aryloxy group, a halogen atom, or a substituent containing an atom of group 15 or group 16 of the periodic table, and $R^{43}$ through $R^{46}$ may be the same or different;

Y, M, X, L, a, b and c are the same as Y, M, X, L, a, b and c, respectively, which are defined for formula (1); and two members selected from Y and $R^{43}$ through $R^{46}$ may be bonded together to form a ring, provided that at least two rings can be formed; X and L may be bonded to each other, L and $R^{46}$ may be bonded to each other, and L and Y may be bonded to each other.

Formula (14):

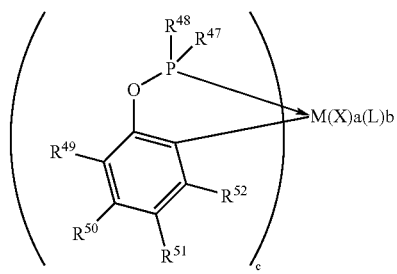

wherein $R^{47}$ through $R^{52}$ represent a hydrogen atom, a hydrocarbon group having 1 to 20 carbon atoms, a substituted silyl group, a substituted amide group, a substituted alkoxy group, a substituted aryloxy group, a halogen atom, or a substituent containing an atom of group 15 or group 16 of the periodic table, and $R^{47}$ through $R^{52}$ may be the same or different;

M, X, L, a, b and c are the same as M, X, L, a, b and c, respectively, which are defined for formula (1); and two members selected from $R^{47}$ through $R^{52}$ may be bonded together to form a ring, X and L may be bonded to each other, L and $R^{47}$ may be bonded to each other, L and $R^{48}$ may be bonded to each other, and L and $R^{52}$ may be bonded together.

In a further aspect of the present invention, there is provided a catalyst for polymerization of an olefin, which comprises (A) a transition metal compound as represented by any one of formulae (1), and (4) through (14), (B) an activating cocatalyst, and (C) an organometallic compound.

In a further aspect of the present invention, there is provided a process for polymerizing an olefin, which comprises polymerizing an olefin in the presence of a catalyst comprising (A) a transition metal compound as represented by any one of formulae (1) and (4) through (14), and (B) an activating cocatalyst.

In a further aspect of the present invention, there is provided a process for polymerizing an olefin, which comprises polymerizing an olefin in the presence of a catalyst comprising (A) a transition metal compound as represented by any one of formulae (1) and (4) through (14), (B) an activating cocatalyst, and (C) an organometallic compound.

DETAILED DESCRIPTION OF THE INVENTION

Transition Metal Compounds

Figure 1:
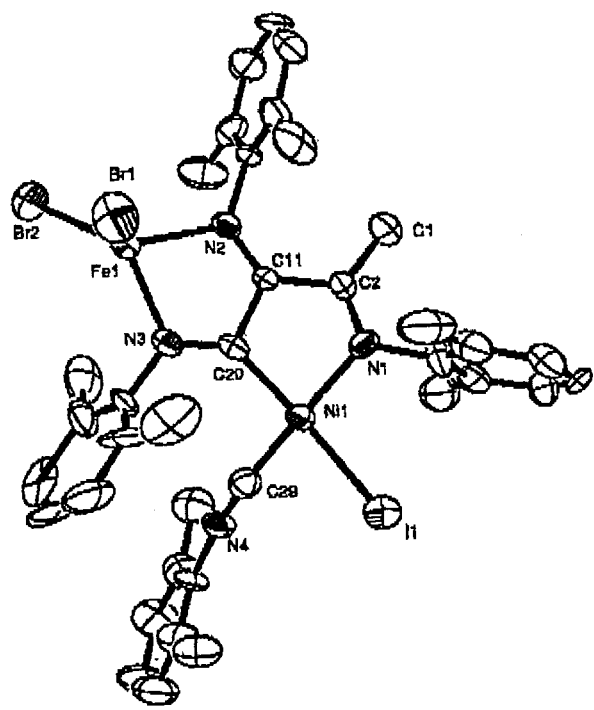
FIG. 1 is an ORTEP diagram of complex 3a-Fe [Iodo[1,2,3-tris(2,6-dimethylphenylimino)butyl](2,6-dimethylphenylisocyanide)nickel(II)]dibromoiron(II).

Novel transition metal compounds are represented by the above-recited formulae (1) and (4) through (9).

In formula (1), $R^1$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, there can be mentioned methyl, ethyl, vinyl, n-propyl, isopropyl, allyl, n-butyl, isobutyl, tert-butyl, pentyl, neopentyl, cyclopentyl, hexyl, cyclohexyl, phenyl, heptyl, benzyl, 2-methylphenyl, 4-methylphenyl, octyl, 2,6-dimethylphenyl, 2-ethylphenyl, nonyl, cumyl, 2-isopropylphenyl, 2,4,6-trimethylphenyl, 2-ethyl-6-methylphenyl, decyl, naphthyl, adamantyl, 2-tert-butylphenyl, 2,6-diethylphenyl, 2-methyl-6-isopropylphenyl, undecyl, 2-ethyl-6-isopropyl, 2,6-diethyl-4-methylphenyl, dodecyl, 2,6-diisopropylphenyl, 2-biphenyl, 2-cyclohexylphenyl, tridecyl, 2,6-diisopropyl-4-methylphenyl, tetradecyl, 2,6-dibutylphenyl, 1-anthracenyl, pentadecyl, 2,6-di-tert-butyl-4-methylphenyl, 2-phenyl-6-isopropyl, hexadecyl, 2-naphthylphenyl, 2-tert-butyl-6-phenylphenyl, heptadecyl, 2-tert-butyl-4-methyl-6-phenylphenyl, octadecyl, 2,6-diphenylphenyl, nonadecyl, triphenylmethyl, 4-methy-2,6-diphenylphenyl, arachidyl, 2,6-di-p-triphenyl, heneicosanyl, 2,6-(p-tolyl)-4-methylphenyl, docosanyl, 2,6-diphenyl-4-tert-butylphenyl, tricosanyl, 2,6-(p-tolyl)-4-isopropyl, tetracosanyl, 2,4,6-triphenylphenyl, pentacosanyl, 2,6-diphenyl-4-(p-tolyl)phenyl, hexacosanyl, 2,6-(p-tolyl)-4-biphenyl, heptacosanyl, octacosanyl, nonacosanyl, triacontanyl and 2,6-bis(biphenyl)phenyl groups. Of these, 2,6-dimethylphenyl, 2,6-diisopropylphenyl, 2-isopropylphenyl and 2-biphenyl groups are preferable. As specific examples of the substituted silyl group, there can be mentioned trimethylsilyl, dimethylphenylsilyl, triisopropylsilyl, dimethylmethoxysilyl, dimethyl-tertbutylsilyl, diphenylmethylsilyl and triphenylsilyl groups. As specific examples of the substituted amide group, there can be mentioned dimethylamide, diethylamide, diisopropylamide, diphenylamide and methylphenylamide groups. As substituted alkoxy groups, there can be mentioned methoxy, ethoxy, isopropoxy and tert-butoxy groups. As specific examples of the substituted aryloxy groups, there can be mentioned phenoxy, 4-methylphenoxy, 2,6-dimethylphenoxy and 1-naphthoxy groups. As specific examples of the hydrocarbon group containing a substituted silyl group, an atom of group 15 or group 16 of the periodic table or a halogen atom, there can be mentioned trimethylsilylmethyl, dimethylphenyl-silymethyl, 2-dimethylaminophenyl, 2-diethylaminophenyl, 2-diisopropylaminophenyl, 2-pyridyl, 6-methyl-2-pyridyl, 2-pyridylphenyl, 2-imidazolyl, 2-cyanophenyl, 2-dimethylphosphinophenyl, 2-diphenylphosphinophenyl, triphenylphosphoranylidenemethyl, 2-methoxyphenyl, 2-ethoxyphenyl, 2-isopropoxyphenyl, 2-phenoxyphenyl, 2-thiomethylphenyl, methylsulfonylmethyl, p-toluenesulfonyl-methyl, trifluoromethyl, 2,2,2-trifluoroethyl, pentafluorophenyl and 2-chloro-1-methylethyl groups.

Z represents a substituent selected from the group consisting of substituents represented by the following formulae (2):

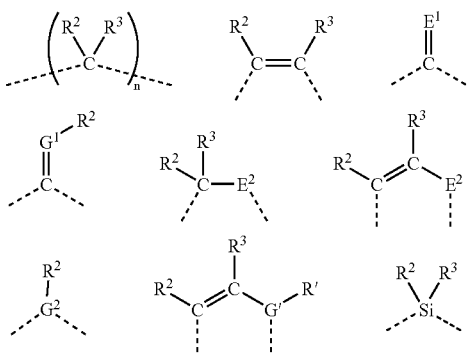

wherein R', $R^2$ and $R^3$ independently represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, there can be mentioned methyl, ethyl, vinyl, n-propyl, isopropyl, allyl, n-butyl, isobutyl, tert-butyl, pentyl, neopentyl, cyclopentyl, hexyl, cyclohexyl, phenyl, heptyl, benzyl, 2-methylphenyl, 4-methylphenyl, octyl, 2,6-dimethylphenyl, 2-ethylphenyl, nonyl, cumyl, 2-isopropylphenyl, 2,4,6-trimethylphenyl, 2-ethyl-6-methylphenyl, decyl, naphthyl, adamantyl, 2-tert-butylphenyl, 2,6-diethylphenyl, 2-methyl-6-isopropylphenyl, undecyl, 2-ethyl-6-isopropyl, 2,6-diethyl-4-methylphenyl, dodecyl, 2,6-diisopropylphenyl, 2-biphenyl, 2-cyclohexylphenyl, tridecyl, 2,6-diisopropyl-4-methylphenyl, tetradecyl, 2,6-dibutylphenyl, 1-anthracenyl, pentadecyl, 2,6-di-tert-butyl-4-methylphenyl, 2-phenyl-6-isopropyl, hexadecyl, 2-naphthylphenyl, 2-tert-butyl-6-phenylphenyl, heptadecyl, 2-tert-butyl-4-methyl-6-phenylphenyl, octadecyl, 2,6-diphenylphenyl, nonadecyl, triphenylmethyl, 4-methy-2,6-diphenylphenyl, arachidyl and 2,6-di-p-triphenyl groups. As specific examples of the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those which are hereinbefore recited for $R^1$ in formula (1). R', $R^2$ and $R^3$ may be the same or different. Two members selected from R', $R^2$ and $R^3$ may be bonded together to form a ring, provided that at least two rings can be formed. $E^1$ and $E^2$ represent an atom of group 16 of the periodic table. G', $G^1$ and $G^2$ represent an atom of group 15 of the periodic table. n is an integer of 0 to 2 provided that a case when n is 0 means that Y and the iminoacyl group in formula (1) are directly bonded to each other.

As specific examples of the substituent Z, there can be mentioned substituents represented by the following formulae.

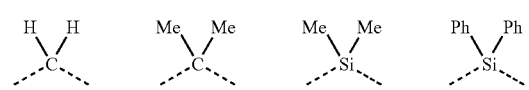

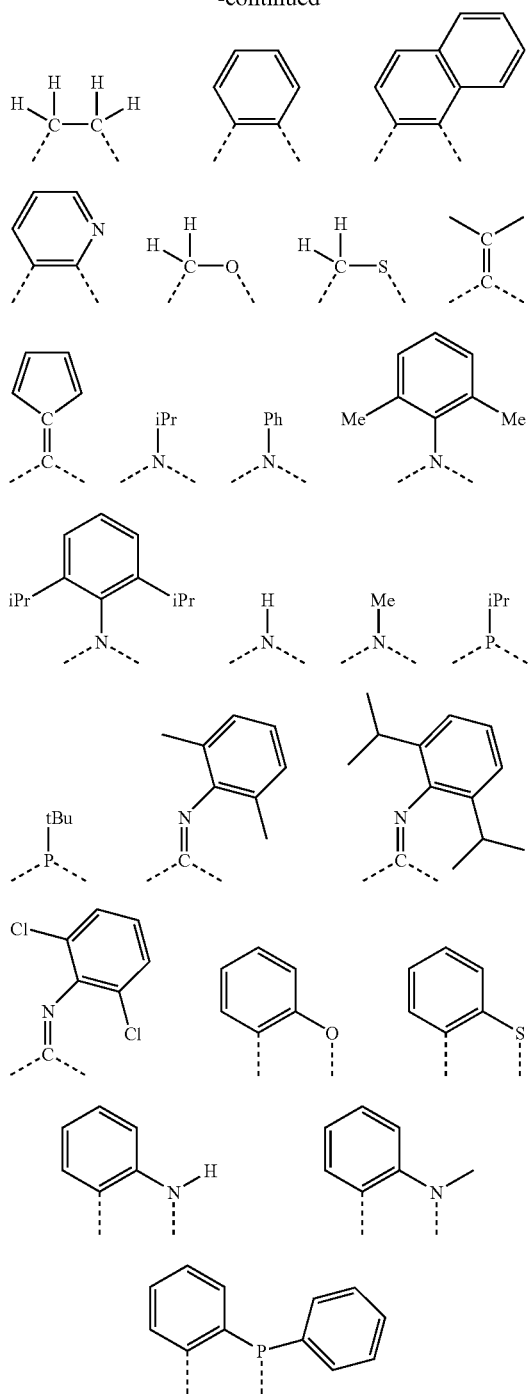

Y represents a substituent selected from substituents represented by the following formulae (3):

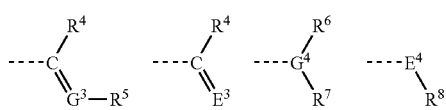

wherein $R^4$, $R^7$ and $R^8$ independently represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those which are hereinbefore recited for R', $R^2$ and $R^3$ in formula (2). $R^5$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those which are hereinbefore recited for $R^1$ in formula (1). $R^6$ represents a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those which are hereinbefore recited for R', $R^2$ and $R^3$ in formula (2). $E^3$ and $E^4$ represent an atom of group 16 of the periodic table. $G^3$ and $G^4$ represent an atom of group 15 of the periodic table. $R^4$ and $R^5$ may be bonded together to form a ring, and $R^6$ and $R^7$ may be bonded together to form a ring.

As specific examples of the substituent Y, there can be mentioned substituents represented by the following formulae.

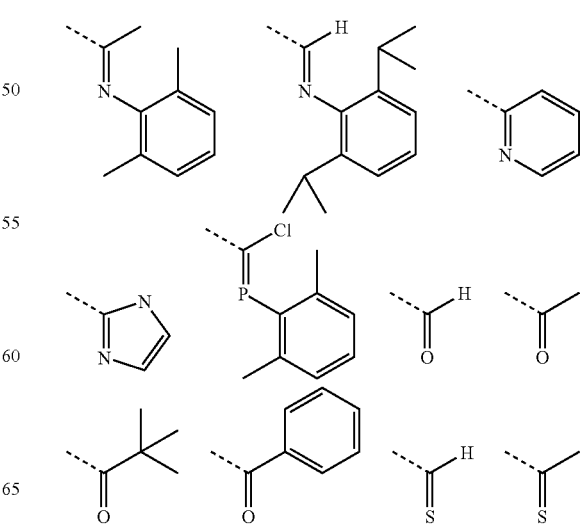

-continued

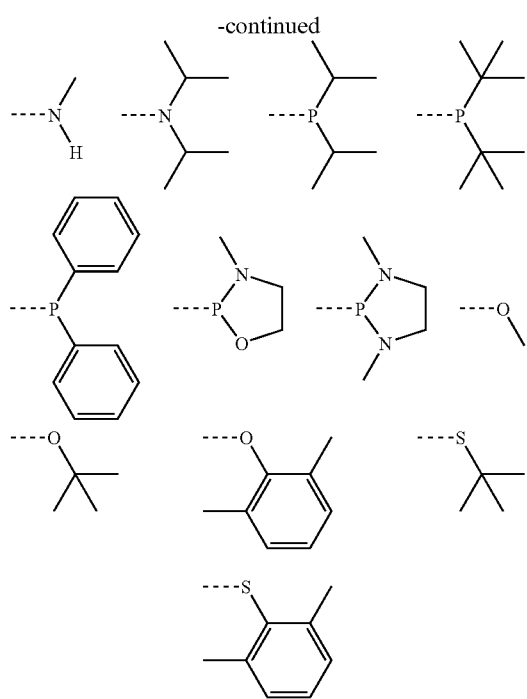

Two members selected from R¹, Z and Y In formula (1) may be bonded together to form a ring.

A represents a transition metal atom of groups 3 to 11 of the periodic table or a typical element of groups 1, 2 and 11 to 16 of the periodic table. As specific examples of the transition metal atom of groups 3 to 11 of the periodic table, there can be mentioned yttrium, samarium, neodymium, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver and gold. Of these, titanium, zirconium, chromium, iron, ruthenium, cobalt, rhodium, nickel, palladium and platinum. Nickel and palladium are especially preferable. As specific examples of the typical element of groups 1, 2 and 11 to 16 of the periodic table, there can be mentioned lithium, sodium, potassium, magnesium, calcium, boron, aluminum, gallium, indium, tin, lead, antimony, bismuth, selenium and tellurium.

X' represents a hydrogen atom, a hydrocarbon group having 1 to 20 carbon atoms, a substituted silyl group, a substituted amide group, a substituted alkoxy group, a substituted aryloxy group, a hydrocarbon group containing a substituted silyl group, or a hydrocarbon group containing an atom of group 15 or group 16 of the periodic table or a halogen atom, or X' is a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those which are hereinbefore recited for R', R² and R³ in formula (2). As specific examples of the halogen atom, there can be mentioned fluorine, chlorine, bromine and iodine. d is an integer of 0 to 6 and, when n is at least 2, X's may be the same or different.

L' is a coordinate bond-forming compound having a coordinating member selected from the group consisting of π electron, atoms of groups 14, 15 and 16 of the periodic table and halogen atoms. As specific examples of the coordinate bond-forming compound having a coordinating member selected from the group consisting of π electron, and atoms of groups 14, 15 and 16 of the periodic table, there can be mentioned ethylene, propylene, butadiene, 1,5-cyclooctadiene, π-allyl, 2,6-dimethylphenylisocyanide, 2,6-dimethylphenylisocyanide, 2,6-diisopropylphenylisocyanide, 2-isopropylphenylisocyanide, 2-biphenylisocyanide, trimethylamine, triethylamine, N,N-dimethylaniline, pyridine, acetonitrile, benzonitrile, trimethylphosphine, dimethylphenylphosphine, methyldiphenylphosphine, triphenylphosphine, trimethyl phosphite, triethyl phosphate, triphenyl phosphite, triphenylphosphine oxide, diethyl ether, tetrahydrofuran and dimethylsulfide. e is an integer of 0 to 6 and, when e is at least 2, L's may be the same or different.

d is an oxidation number of the central metal A. f is an integer of 0 or 1.

M represents a transition metal atom of groups 3 to 11 of the periodic table. As specific examples of the transition metal atom of groups 3 to 11 of the periodic table, there can be mentioned yttrium, samarium, neodymium, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver and gold. Of these, titanium, zirconium, chromium, iron, ruthenium, cobalt, rhodium, nickel, palladium and platinum. Nickel and palladium are especially preferable.

X represents a hydrogen atom, a hydrocarbon group having 1 to 20 carbon atoms, a substituted silyl group, a substituted amide group, a substituted alkoxy group, a substituted aryloxy group, a hydrocarbon group containing a silyl group, or a hydrocarbon group containing an atom of group 15 or group 16 of the periodic table or a halogen atom, or X is a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those which are hereinbefore recited for R', R² and R³ in formula (2). As specific examples of the halogen atom, there can be mentioned fluorine, chlorine, bromine and iodine. a is an integer of 1 to 5 and, when n is at least 2, Xs may be the same or different.

L is a coordinate bond-forming compound having a coordinating atom selected from the group consisting of π electron, atoms of groups 14, 15 and 16 of the periodic table and halogen atoms. As specific examples of the coordinate bond-forming compound having a coordinating member selected from the group consisting of π electron, and atoms of groups 14, 15 and 16 of the periodic table, there can be mentioned those which are hereinbefore recited for L' in formula (1). b is an integer of 0 to 6 and, when b is at least 2, Ls may be the same or different. X and L may be bonded to each other, L and R¹ may be bonded to each other, and L and Y may be bonded to each other.

c is an integer of 1 to 5 and the sum of "a+c" is an oxidation number of the central metal M.

As specific examples of the transition metal compound represented by formula (1), there can be mentioned compounds represented by the following formulae.
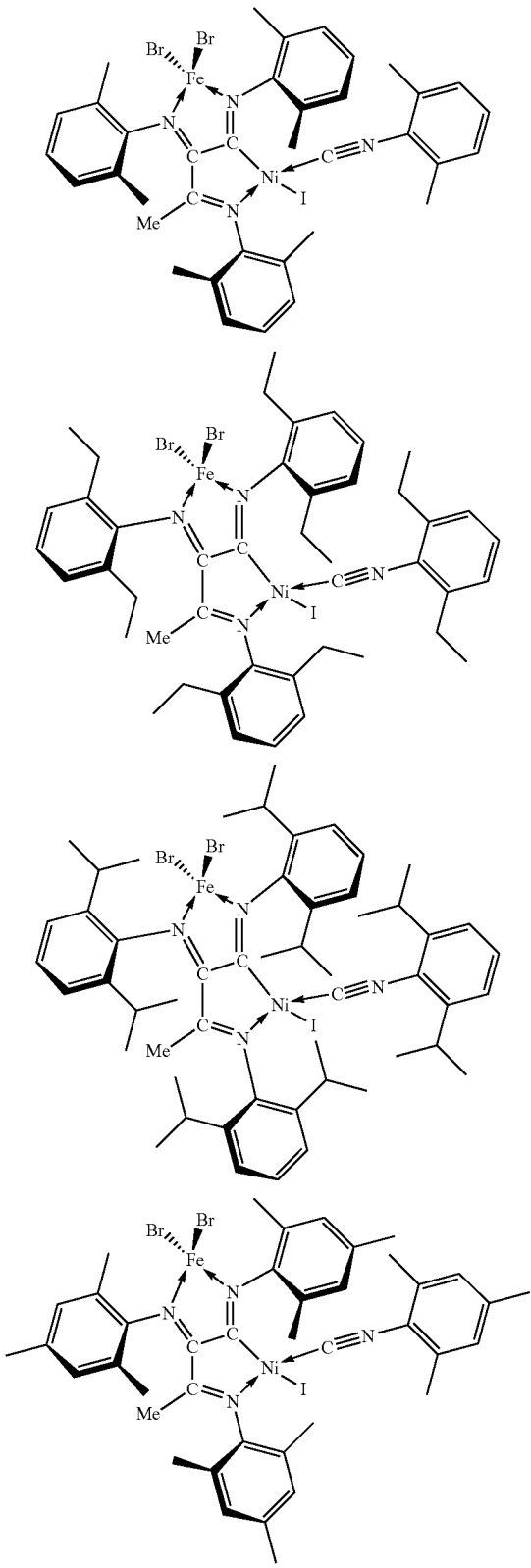
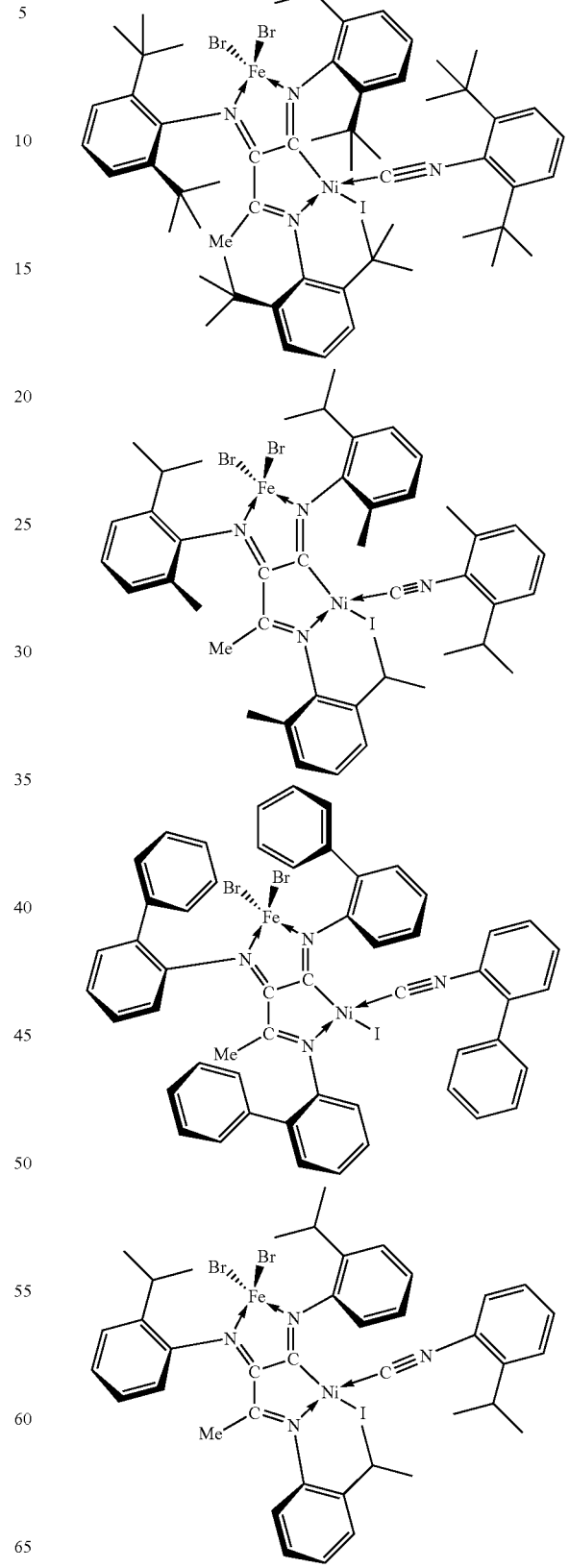

-continued
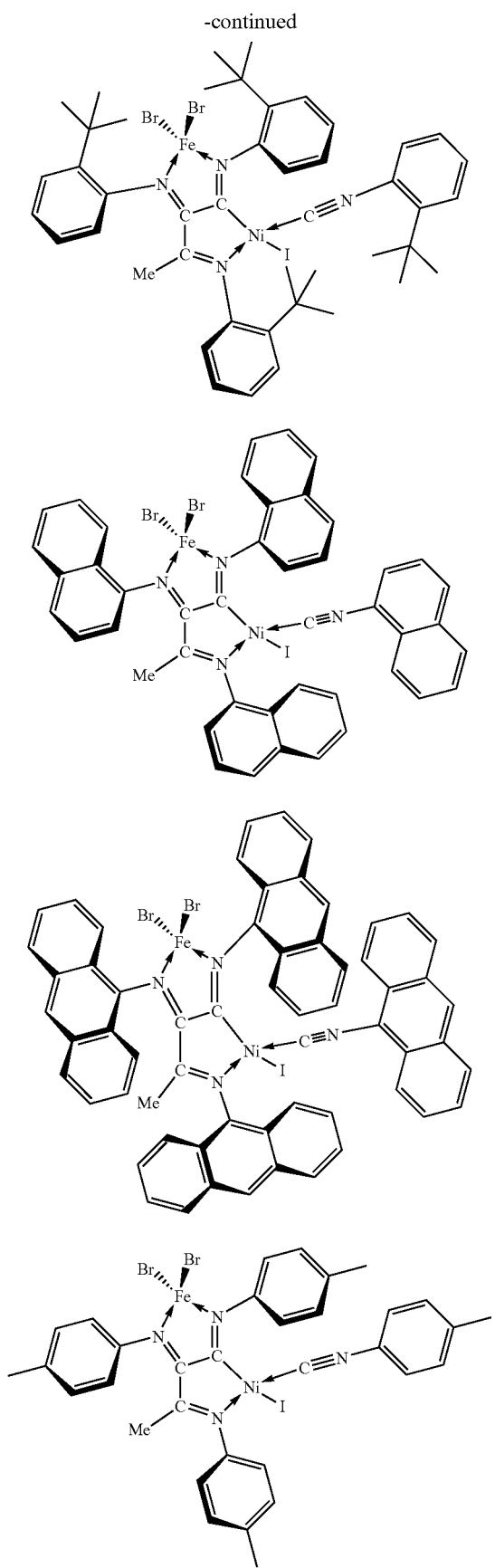
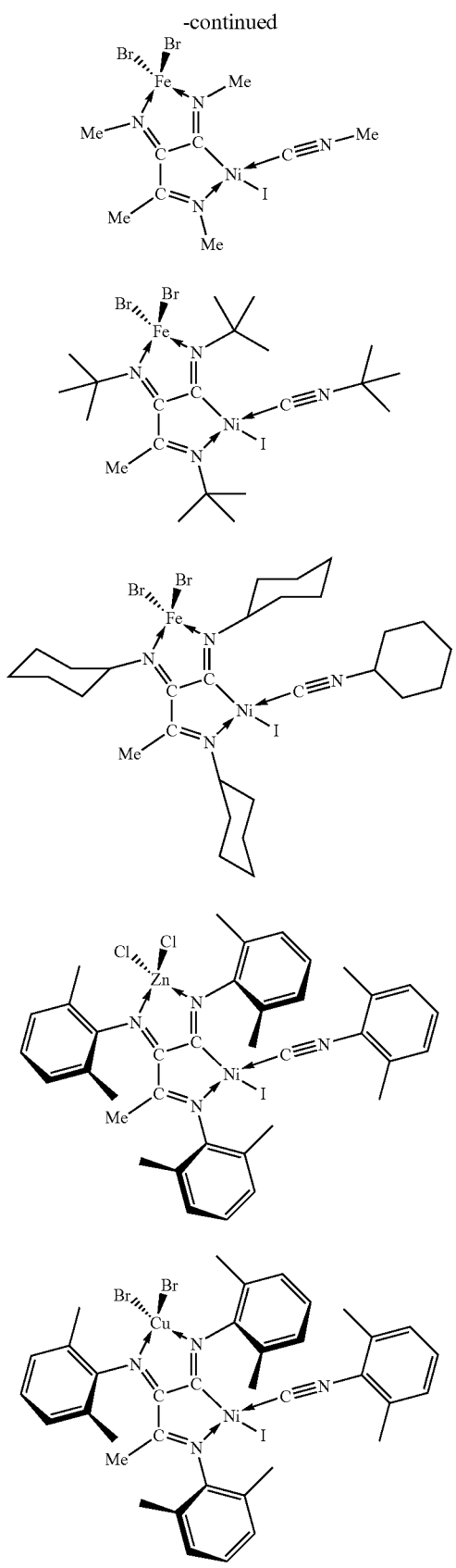

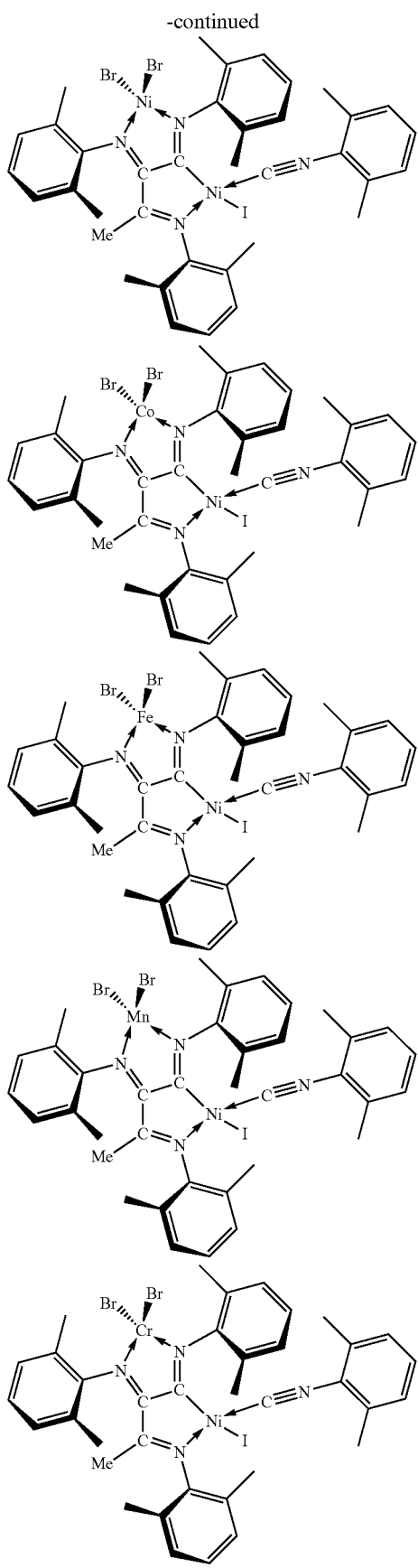
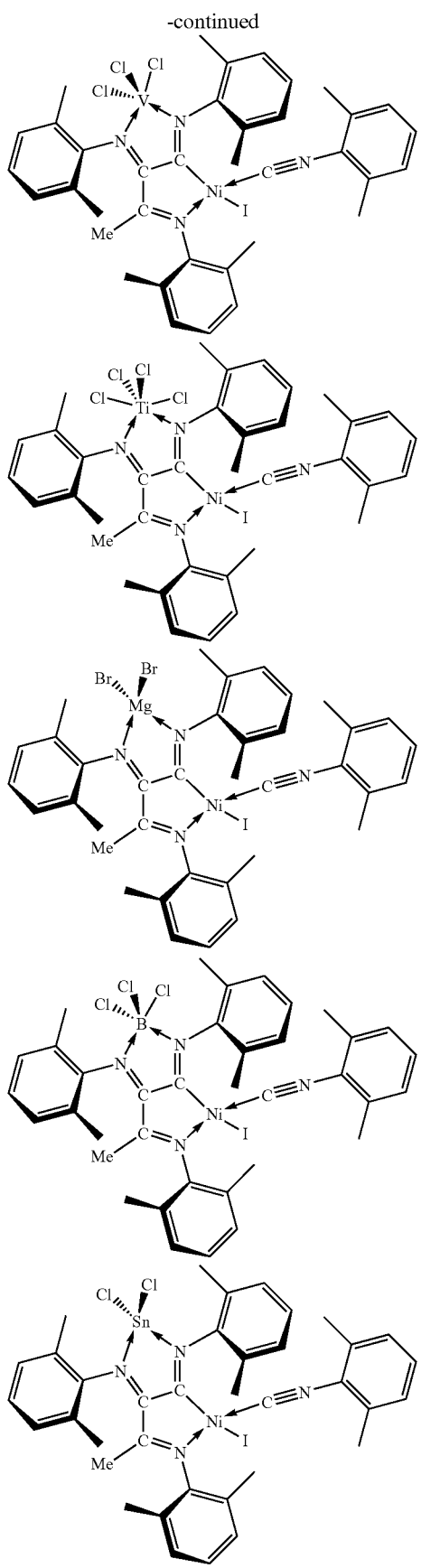

-continued
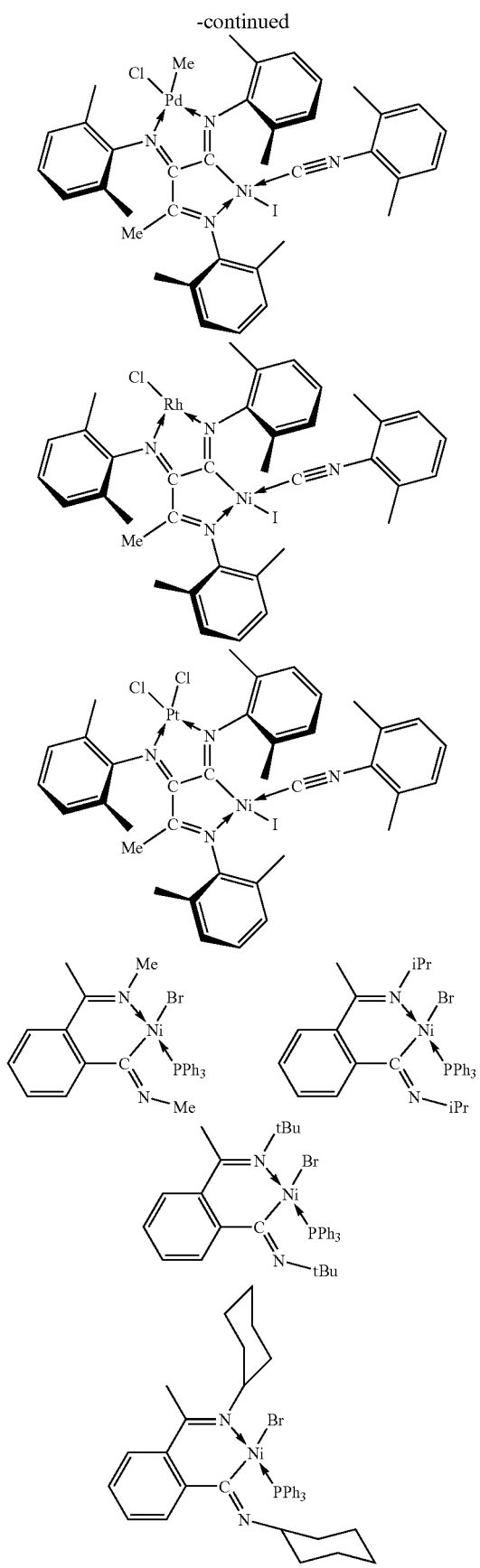
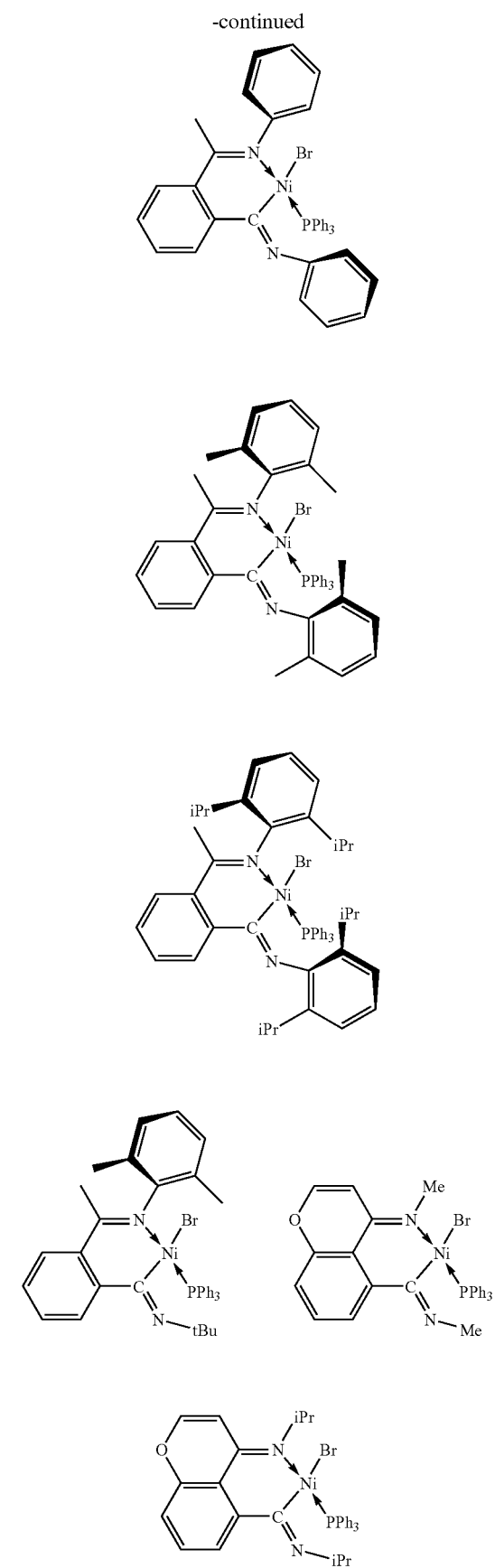

-continued
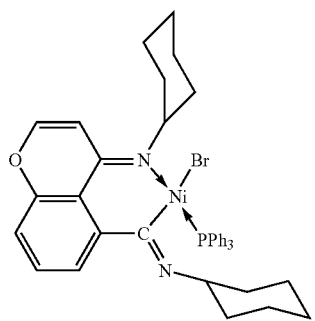
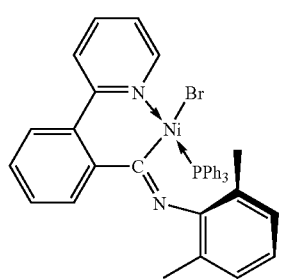
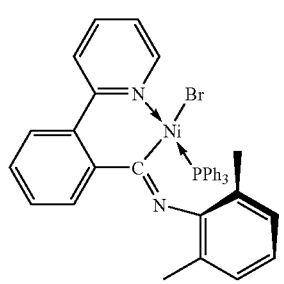
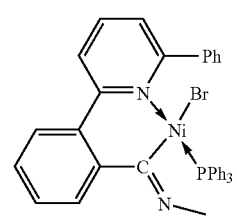
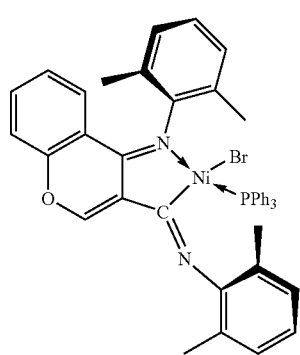
-continued
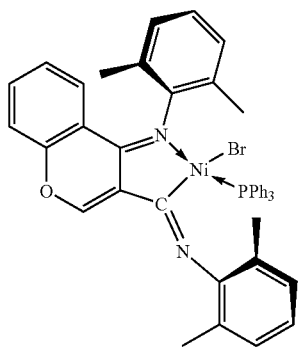
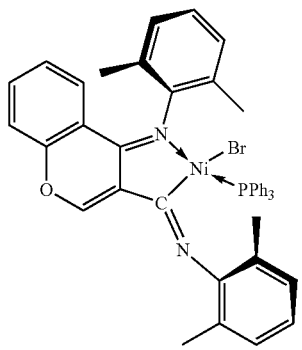
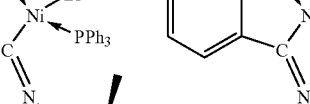
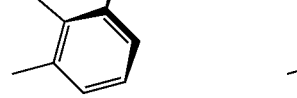
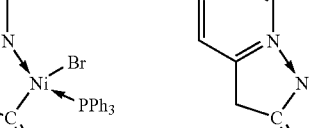
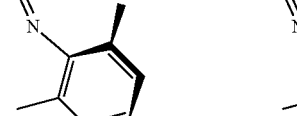
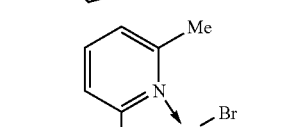
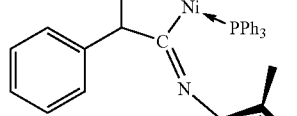
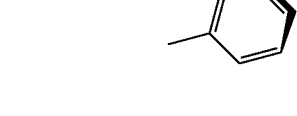

-continued
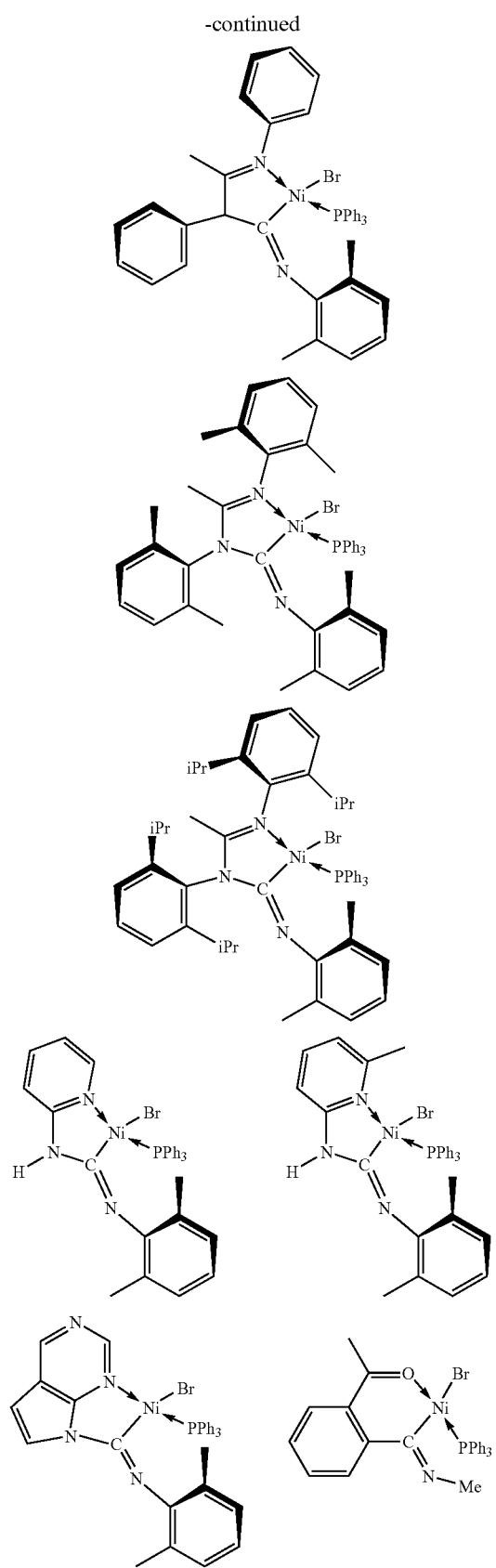
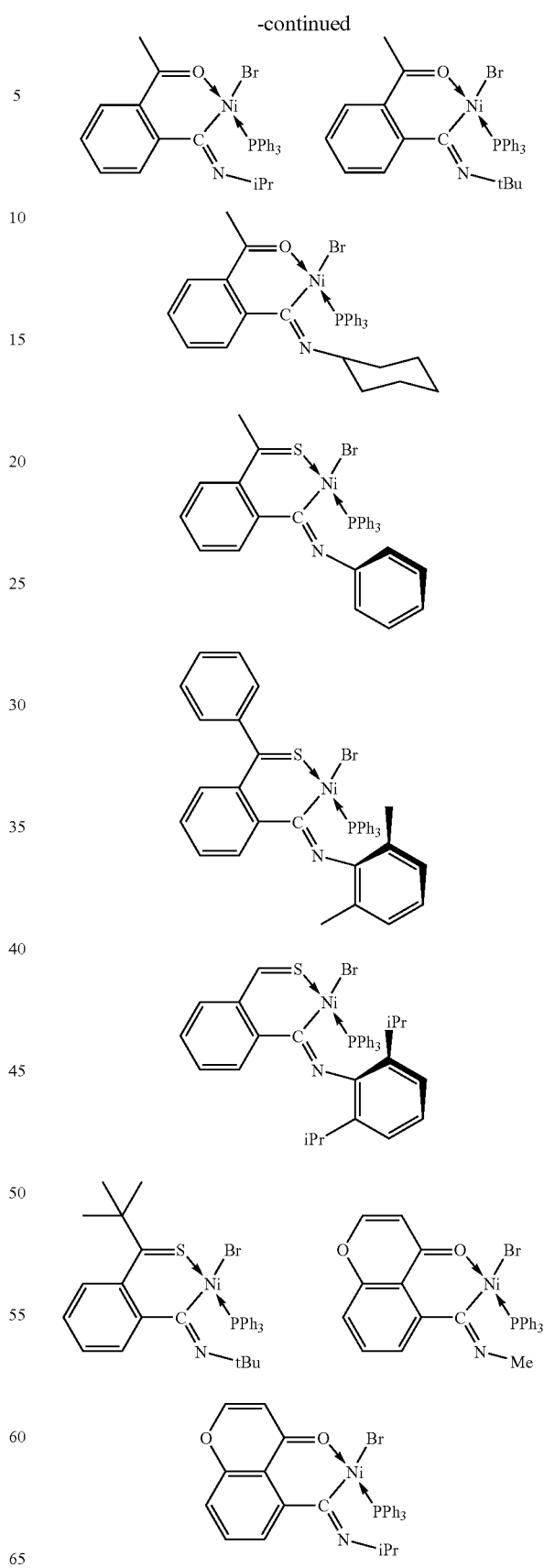

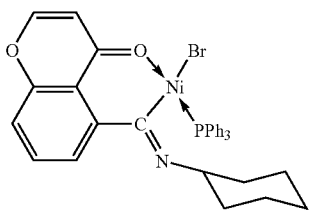
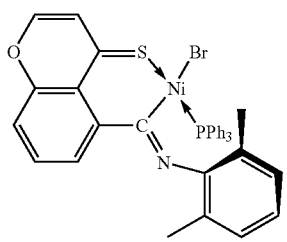
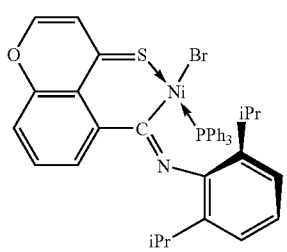
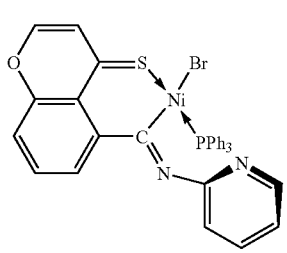
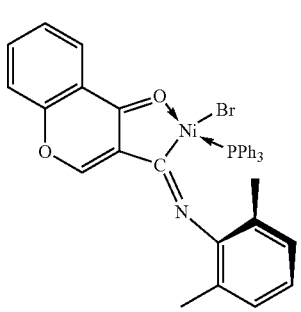
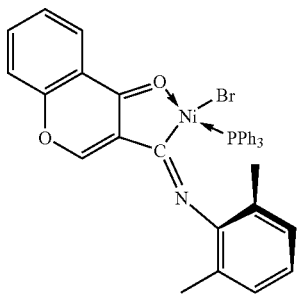
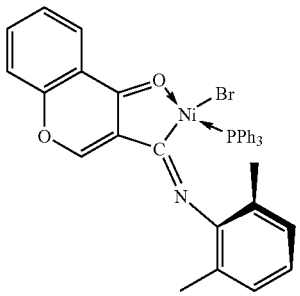
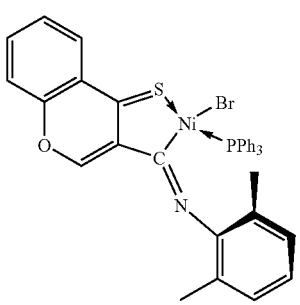
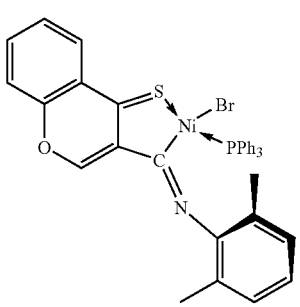
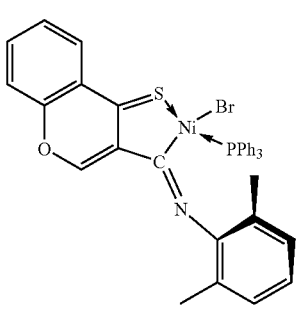
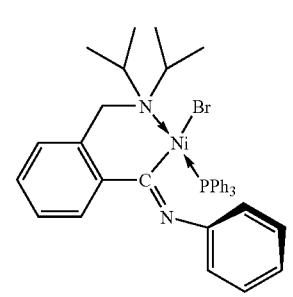

-continued
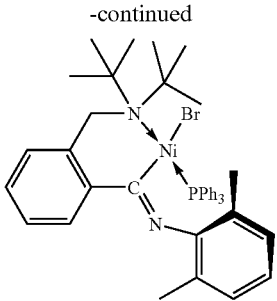
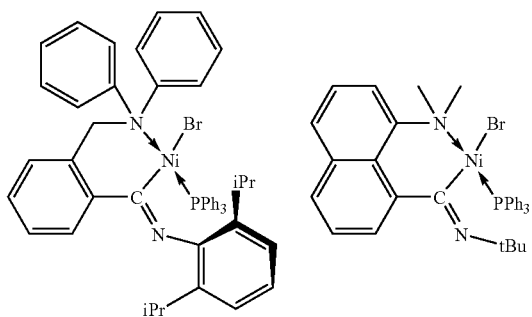
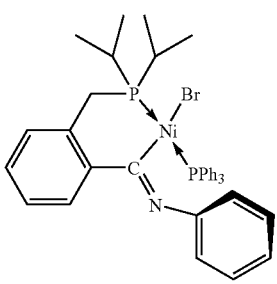
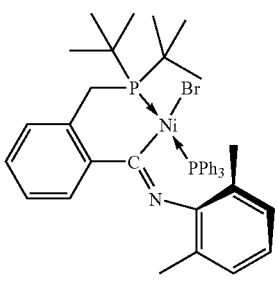
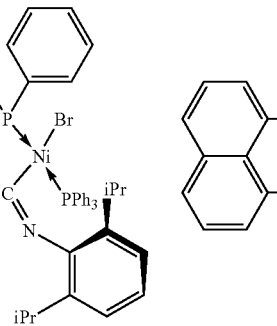
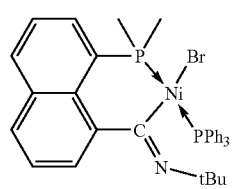
-continued
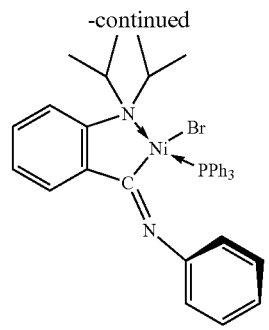
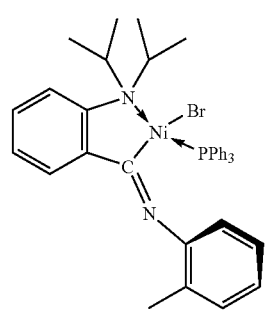
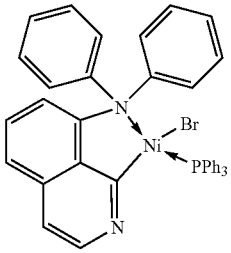
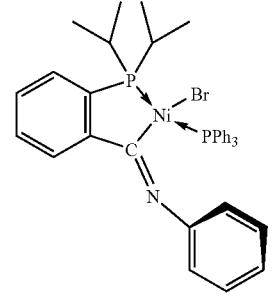
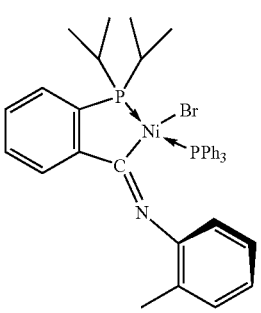
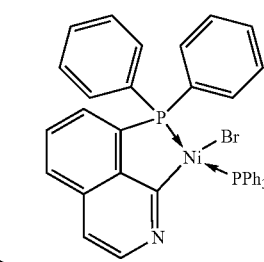
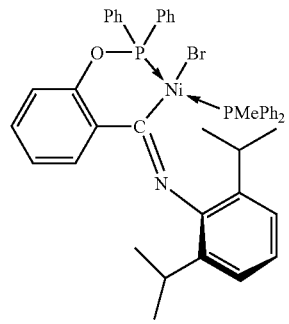

-continued

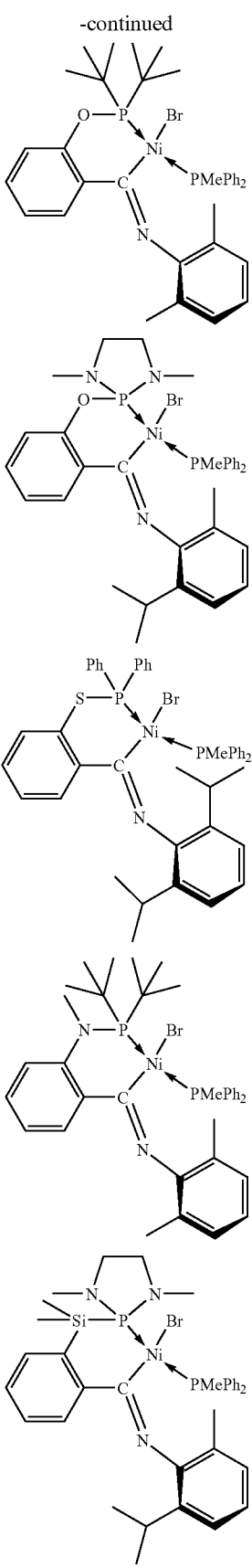

The process for preparing the transition metal compound of formula (1) is not particularly limited, but the transition metal compound of formula (1) can be prepared by the following process.

A ligand precursor represented by the following general formula (1-A):

wherein Y and Z are the same as Y and Z, respectively, which are defined for formula (1), and X" represents a, hydrogen atom, a substituted silyl group, a substituted stannyl group or a halogen atom, is allowed to react with a raw material complex containing a transition metal M wherein M is the same as M defined for formula (1), to give an intermediate represented by the following general formula (1-B):

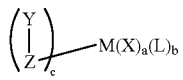

wherein Y, Z, M, X, L, a, b and c are the same as Y, Z, M, X, L, a, b and c, respectively, which are defined for formula (1). More specifically, X" in the ligand precursor of formula (1-A) is metallized by an organometal reagent at a low temperature, and the thus-obtained compound is allowed to react with the transition metal-containing raw material complex to give a transition metal compound of formula (1-B). Alternatively, X" in the ligand precursor of formula (1-A) is not metallized, and the ligand precursor of formula (1-A) Is allowed to react with a raw material complex which is a transition metal compound having a low valence, whereby oxidative addition of C—X" bond proceeds to give a transition metal compound of formula (1-B).

The transition metal compound of formula (1-B) is allowed to react with an isocyanide represented by the general formula: C≡N—R$^1$ wherein R$^1$ is the same as defined for formula (1), to give a transition metal compound represented by the following general formula (1-C):

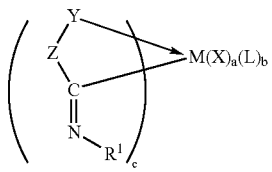

wherein Y, Z, R$^1$, M, X, L, a, b and c are the same as Y, Z, R$^1$, M, X, L, a, b and c, respectively, which are defined for formula (1). The transition metal compound of formula (1-C) is the same as a transition metal compound of formula (1) wherein f is 0.

The transition metal compound of formula (1-C) is allowed to react with a compound represented by the general formula: A(X')d(L')e wherein A, X', L', d and e are the same as A, X', L', d and e, respectively, which are defined for formula (1), to give the transition metal compound of formula (1).

When f is 0, a reaction product of the compound of formula (1-B) with the isocyanide of C≡N—R¹ can be used as a catalyst ingredient for polymerization of an olefin instead of the transition metal compound of formula (1) without separation of the reaction product.

A reaction product of the transition metal compound of formula (1-C) with the compound of formula: A(X')d(L')e can be used as a catalyst ingredient for polymerization of an olefin instead of the transition metal compound of formula (1) without separation of the reaction product.

In formula (4) representing a transition metal compound of the present invention, $R^9$ and $R^{11}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for $R^1$ in formula (1).

$R^{10}$ represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for R', $R^2$ and $R^3$ in formula (2).

Z, M, X, L, A, X', L', a, b, c, d, e and f are the same as Z, M, X, L, A, X', L', a, b, c, d, e and f, which are defined for formula (1). Two members selected from $R^9$, $R^{10}$, $R^{11}$ and Z may be bonded to each other to form a ring, provided that at least two rings can be formed. X and L may be bonded to each other, L and $R^9$ may be bonded to each other, and L and $R^{11}$ may be bonded to each other.

As specific examples of the transition metal compound represented by formula (4), there can be mentioned compounds represented by the following formulae.

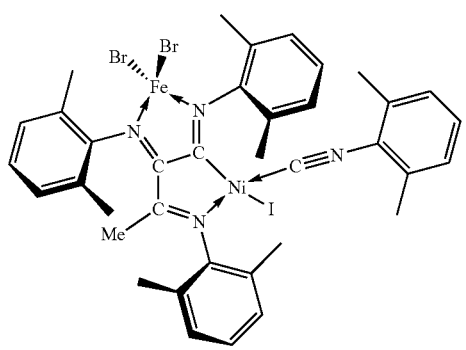

-continued

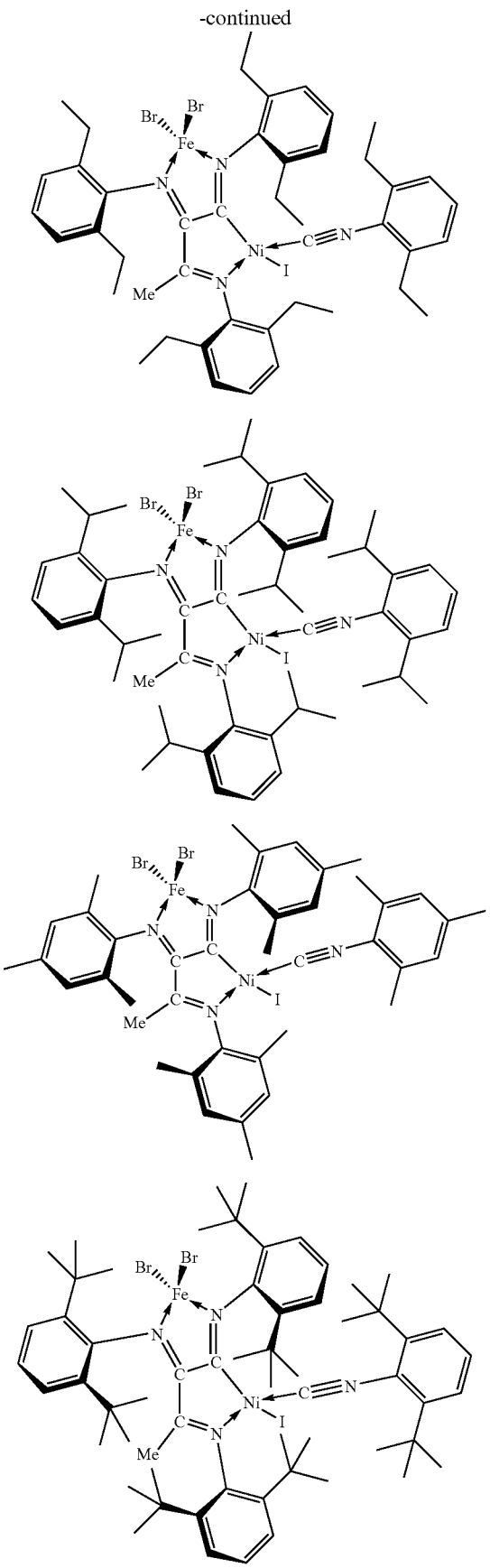

-continued
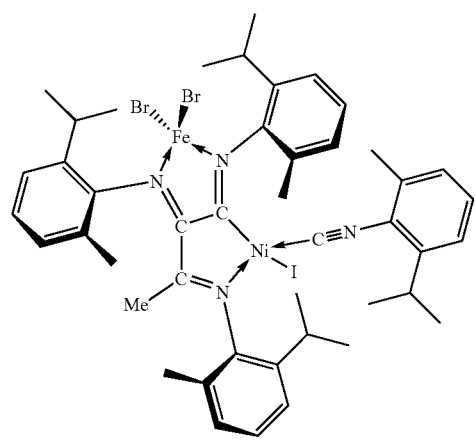
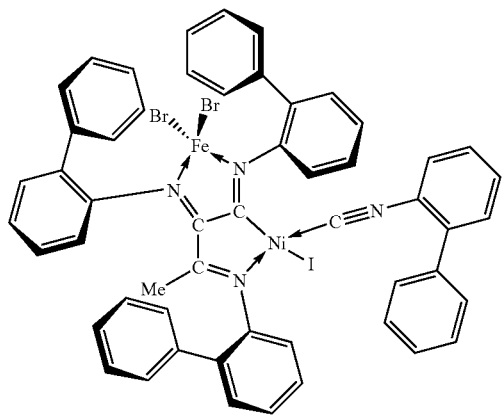
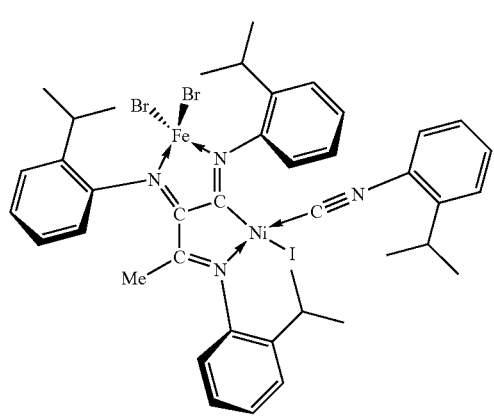
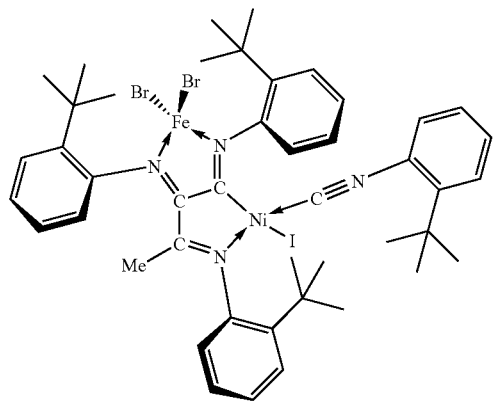
-continued
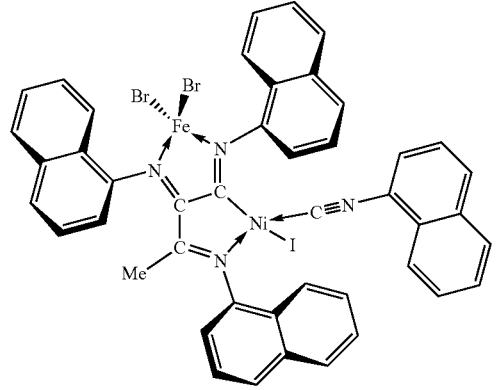
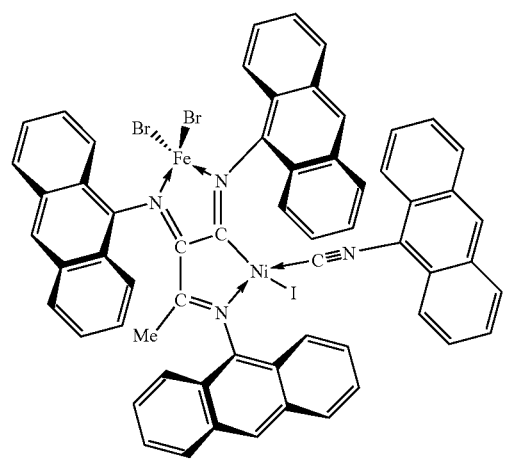
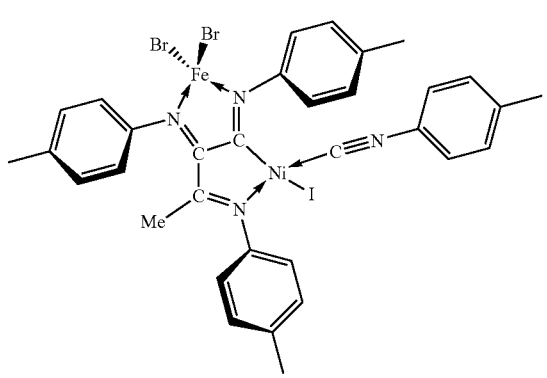
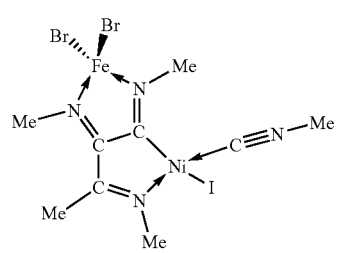

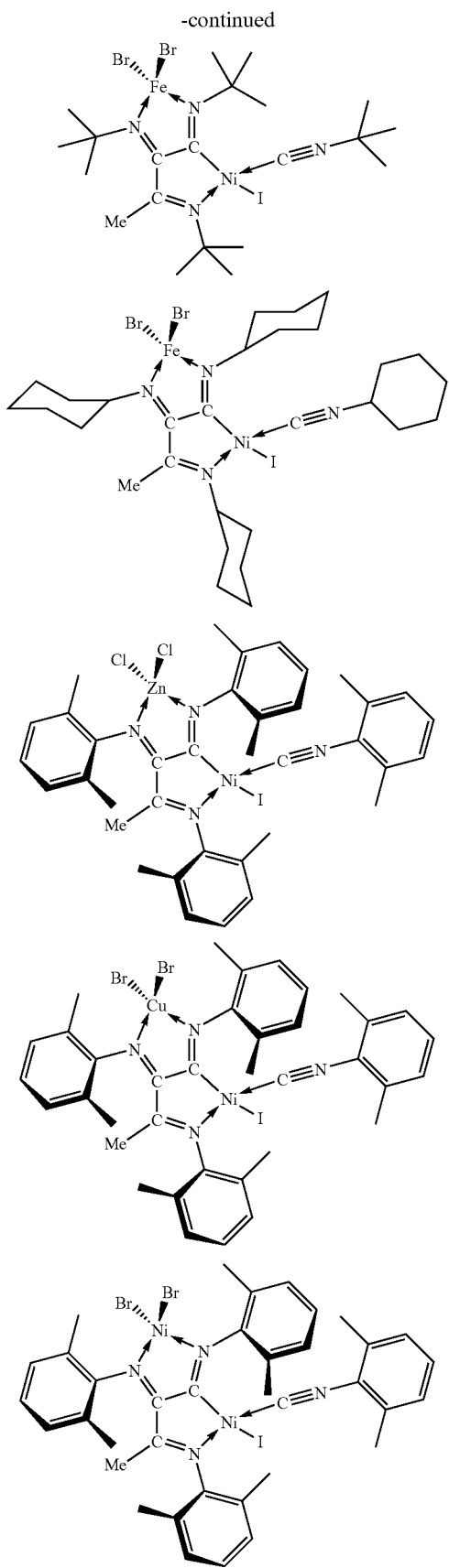
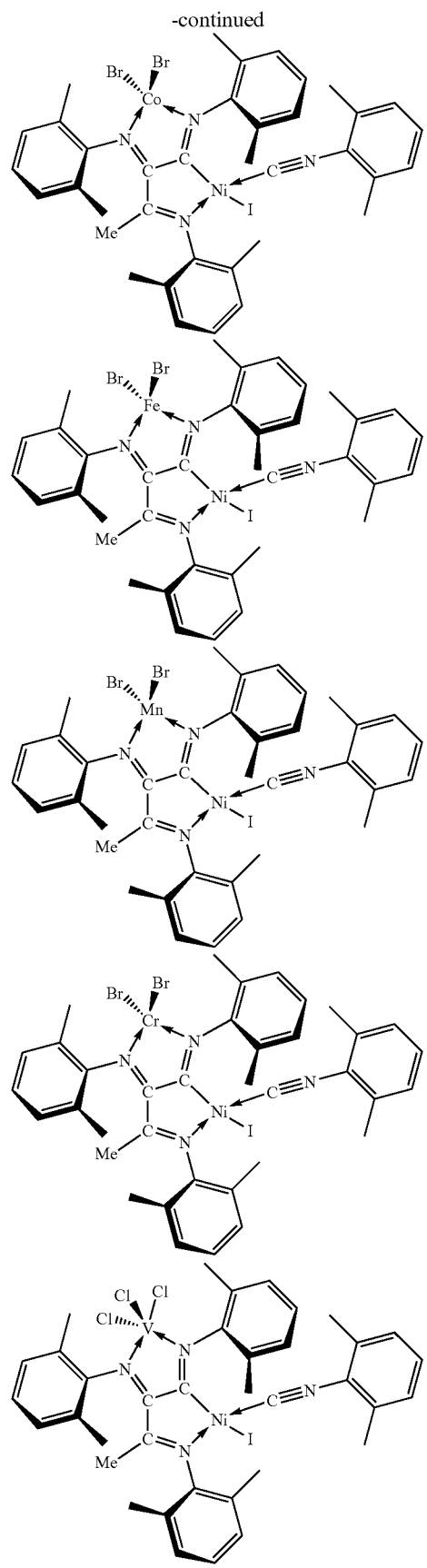

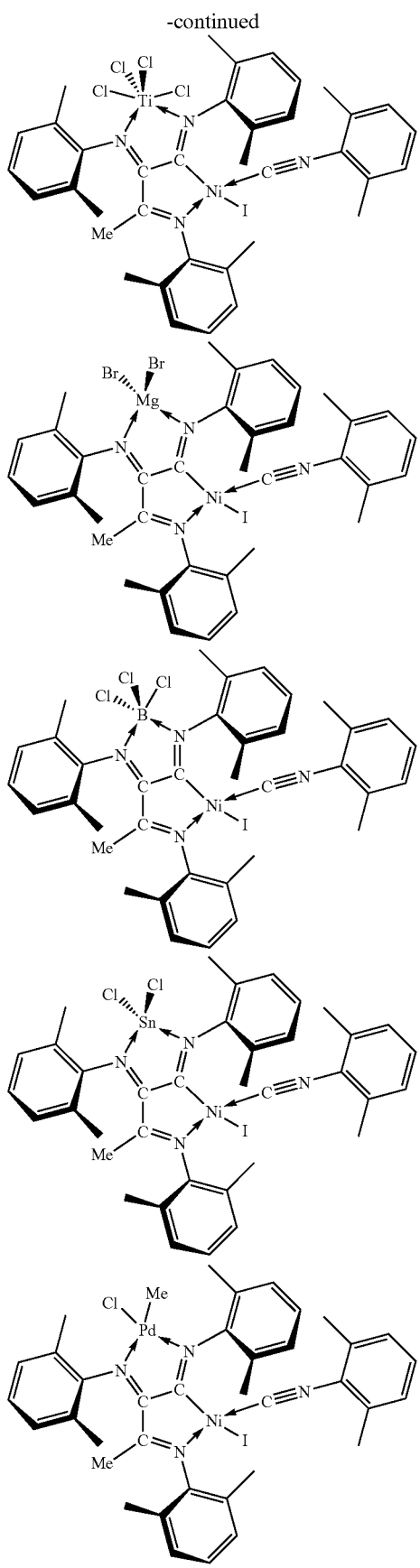
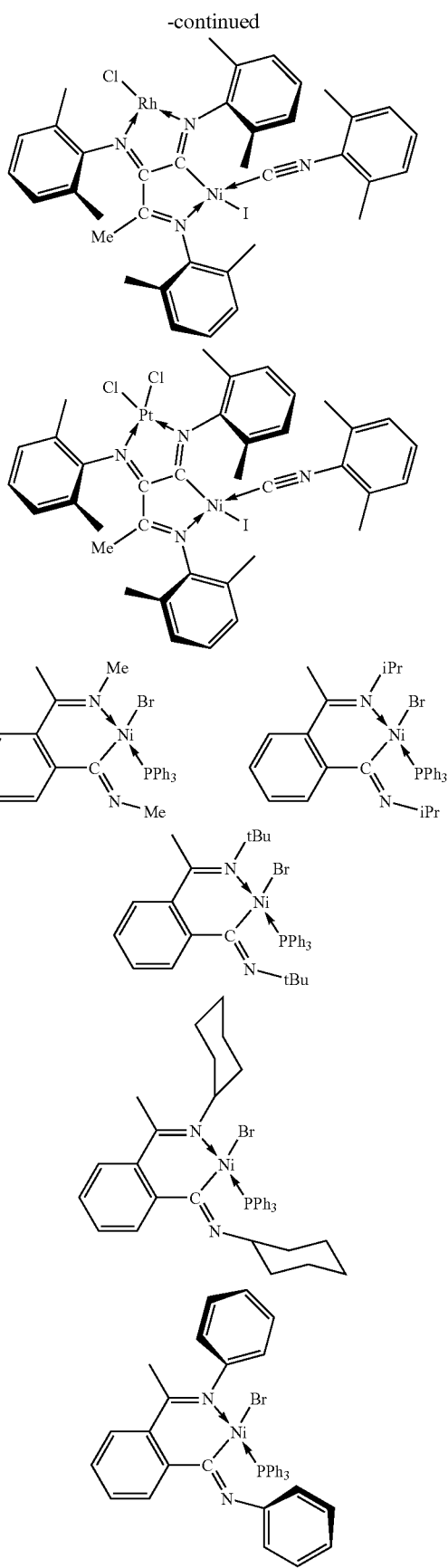

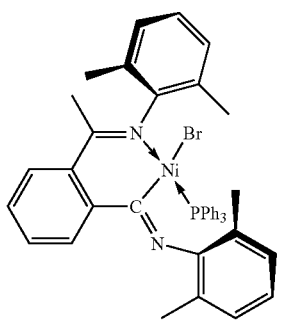
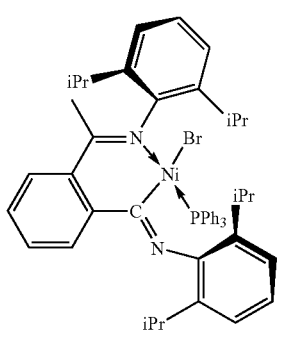
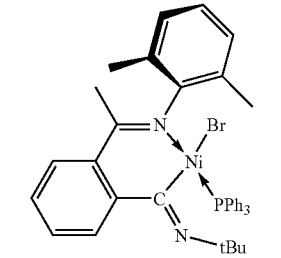
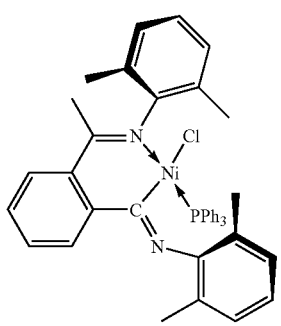
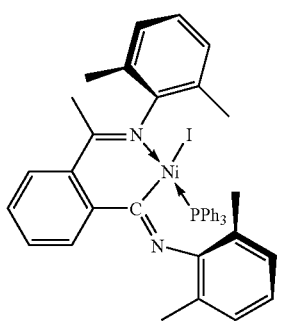
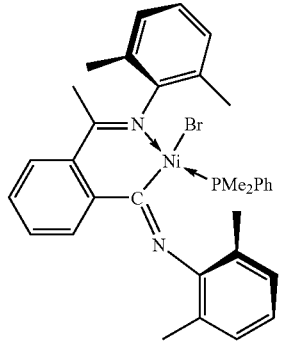
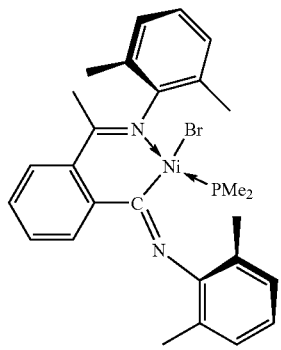
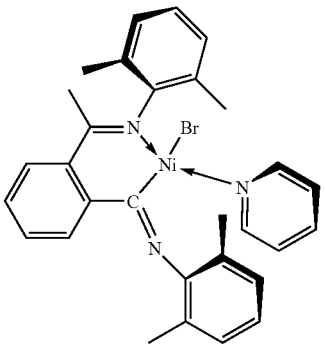
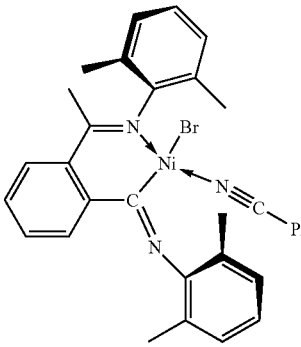

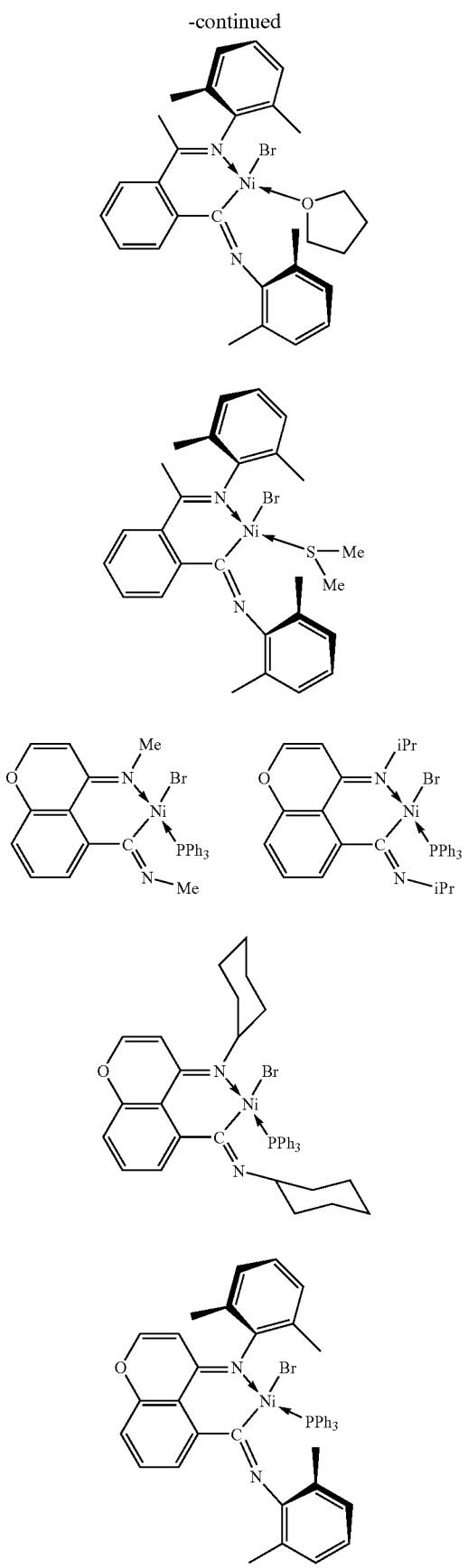
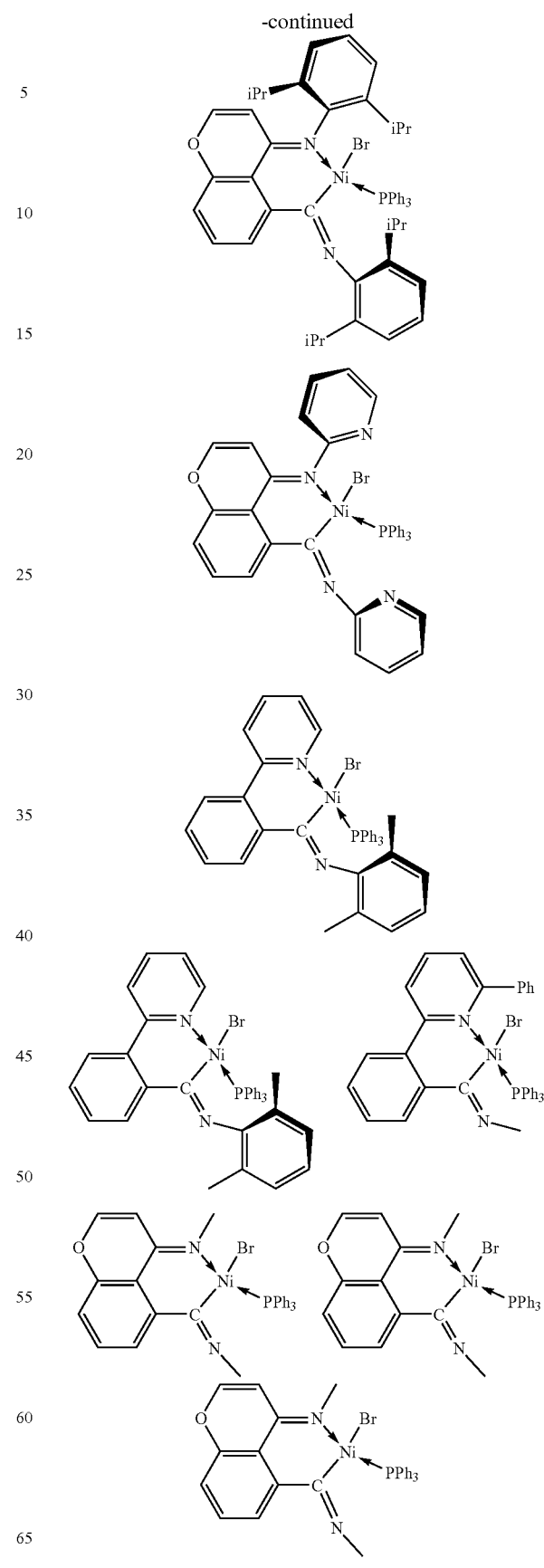

-continued
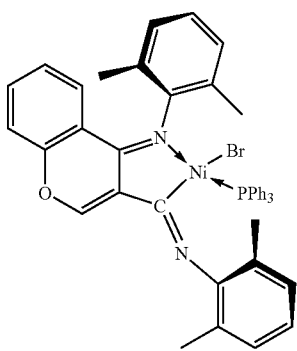
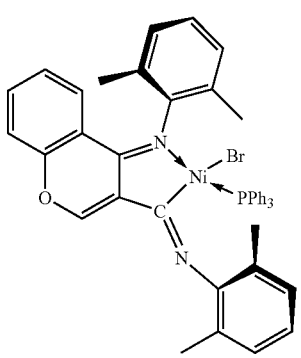
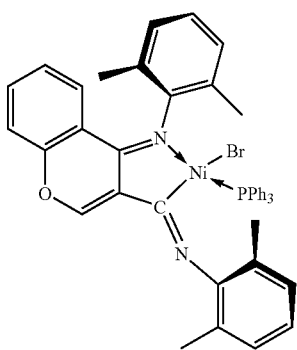
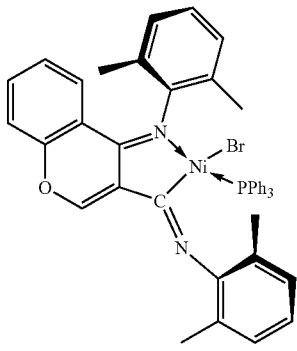
-continued
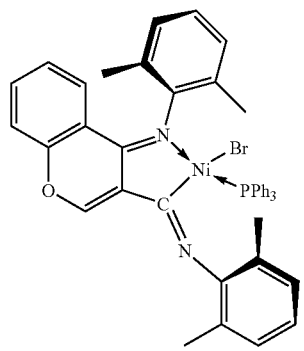
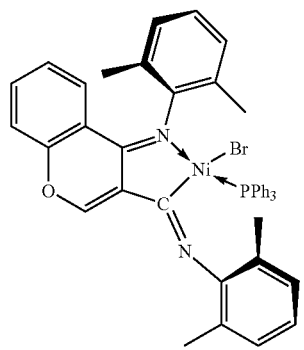
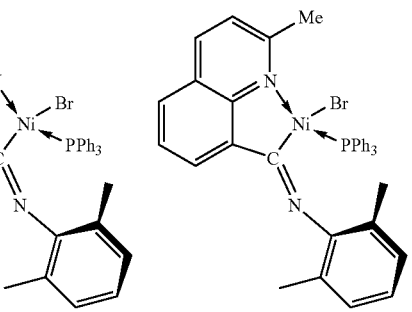
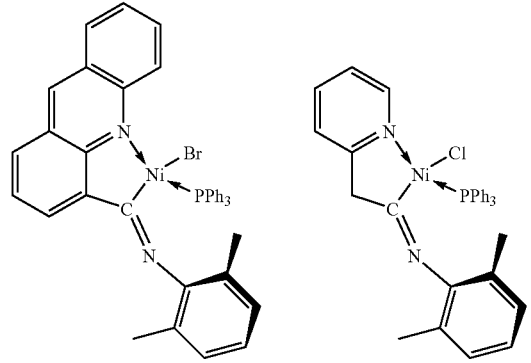
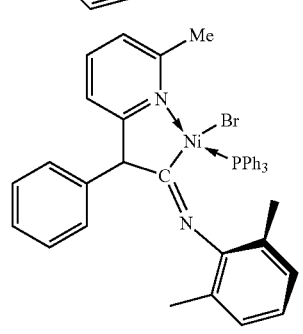

-continued

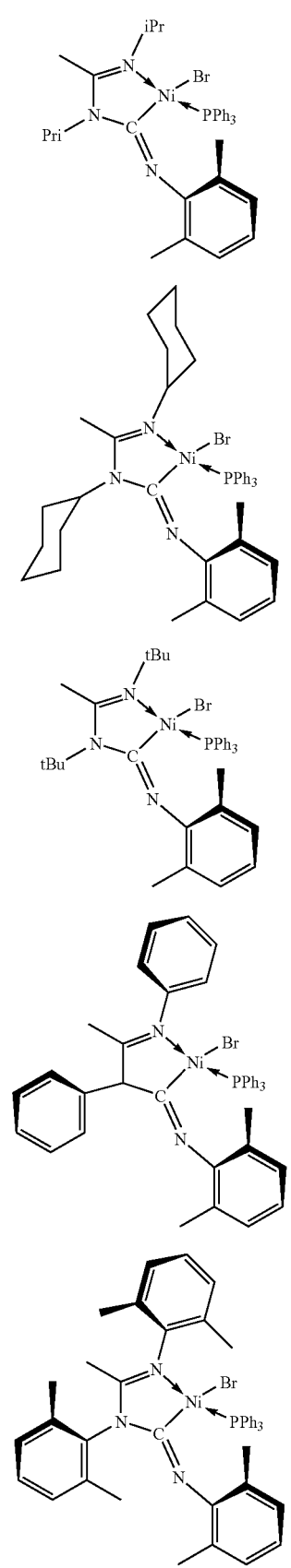

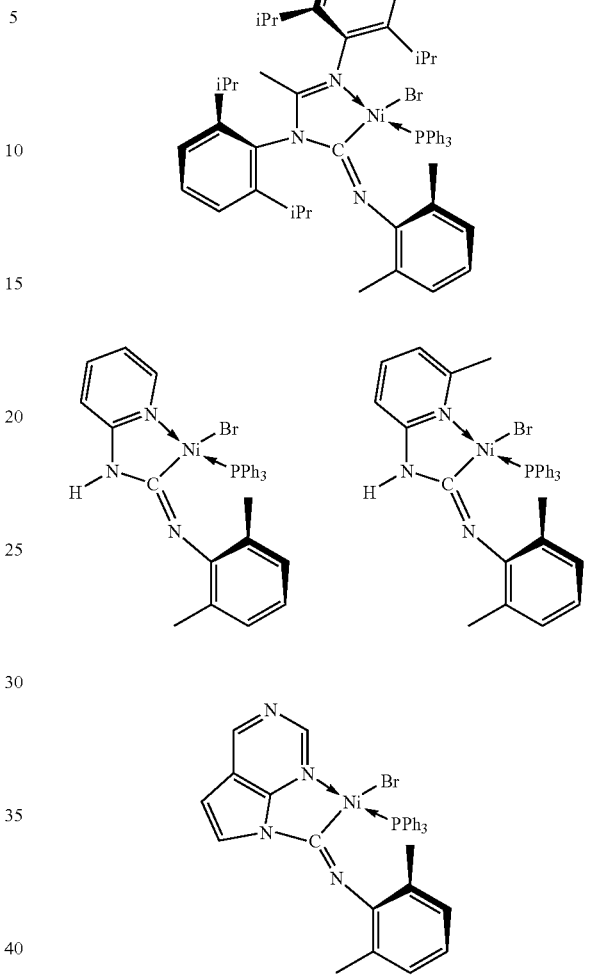

The process for preparing the transition metal compound of formula (4) is not particularly limited, but the transition metal compound of formula (4) can be prepared by the following process.

A ligand precursor represented by the following general formula (4-A):

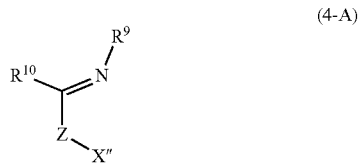

(4-A)

wherein $R^9$, $R^{10}$ and Z are the same as $R^9$, $R^{10}$ and Z, respectively, which are defined for formula (4), and X" represents a hydrogen atom, a substituted silyl group, a substituted stannyl group or a halogen atom, is allowed to react with a raw material complex containing a transition metal M wherein M is the same as M defined for formula (4), to give an intermediate represented by the following general formula (4-B):

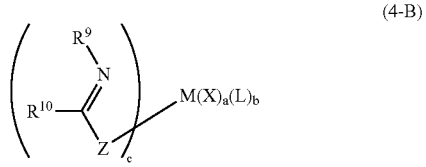

(4-B)

wherein $R^9$, $R^{10}$, Z, M, X, L, a, b and c are the same as $R^9$, $R^{10}$, Z, M, X, L, a, b and c, respectively, which are defined for formula (4). More specifically, X" in the ligand precursor of formula (4-A) is metallized by an organometal reagent at a low temperature, and the thus-obtained compound is allowed to react with the transition metal-containing raw material complex to give a transition metal compound of formula (4-B). Alternatively, X" in the ligand precursor of formula (4-A) is not metallized, and the ligand precursor of formula (4-A) is allowed to react with a raw material complex which is a transition metal compound having a low valence, whereby oxidative addition of Z-X" bond proceeds to give a transition metal compound of formula (4-B).

The transition metal compound of formula (4-B) is allowed to react with an isocyanide represented by the general formula: C≡N—$R^{11}$ wherein $R^{11}$ is the same as $R^{11}$ defined for formula (4), to give a transition metal compound represented by the following general formula (4-C):

(4-C)

wherein $R^9$, $R^{10}$, $R^{11}$, Z, M, X, L, a, b and c are the same as $R^9$, $R^{10}$, $R^{11}$, Z, M, X, L, a, b and c, respectively, which are defined for formula (4). The transition metal compound of formula (4-C) is the same as a transition metal compound of formula (4) wherein f is 0.

The transition metal compound of formula (4-C) is allowed to react with a compound represented by the general formula: A(X')d(L')e wherein A, X', L', d and e are the same as A, X', L', d and e, respectively, which are defined for formula (4), to give the transition metal compound of formula (4).

When f is 0, a reaction product of the compound of formula (4-B) with the isocyanide of C≡N—$R^{11}$ can be used as a catalyst ingredient for polymerization of an olefin instead of the transition metal compound of formula (4) without separation of the reaction product.

A reaction product of the transition metal compound of formula (4-C) with the compound of formula: A(X')d(L')e can be used as a catalyst ingredient for polymerization of an olefin instead of the transition metal compound of formula (4) without separation of the reaction product.

In formula (5) representing a transition metal compound of the present invention, $R^{12}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for $R^1$ in formula (1).

$R^{13}$ represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for R', $R^2$ and $R^3$ in formula (2).

$E^5$ represents an atom of group 16 of the periodic table. Z, M, X, L, a, b and c are the same as Z, M, X, L, a, b and c, respectively, which are defined for formula (1). Two members selected from $R^{12}$, $R^{13}$ and Z may be bonded to each other to form a ring, provided that at least two rings can be formed. X and L may be bonded to each other, and L and $R^{12}$ may be bonded to each other.

As specific examples of the transition metal compound represented by formula (5), there can be mentioned compounds represented by the following formulae.

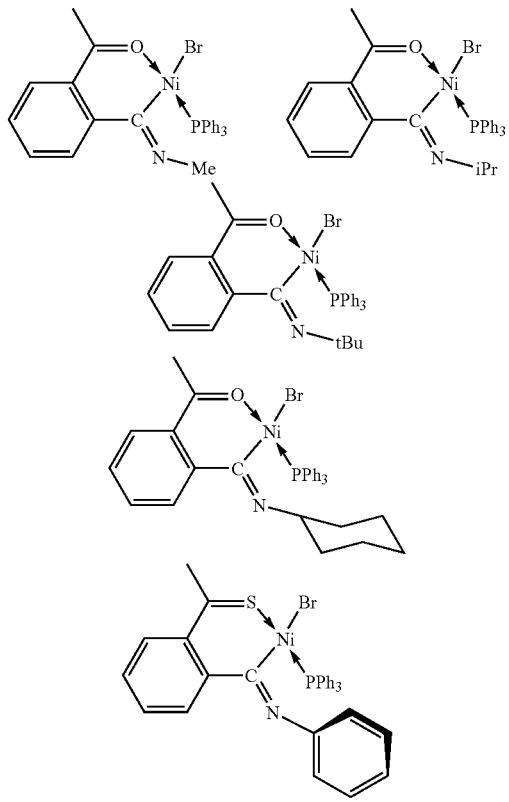

-continued
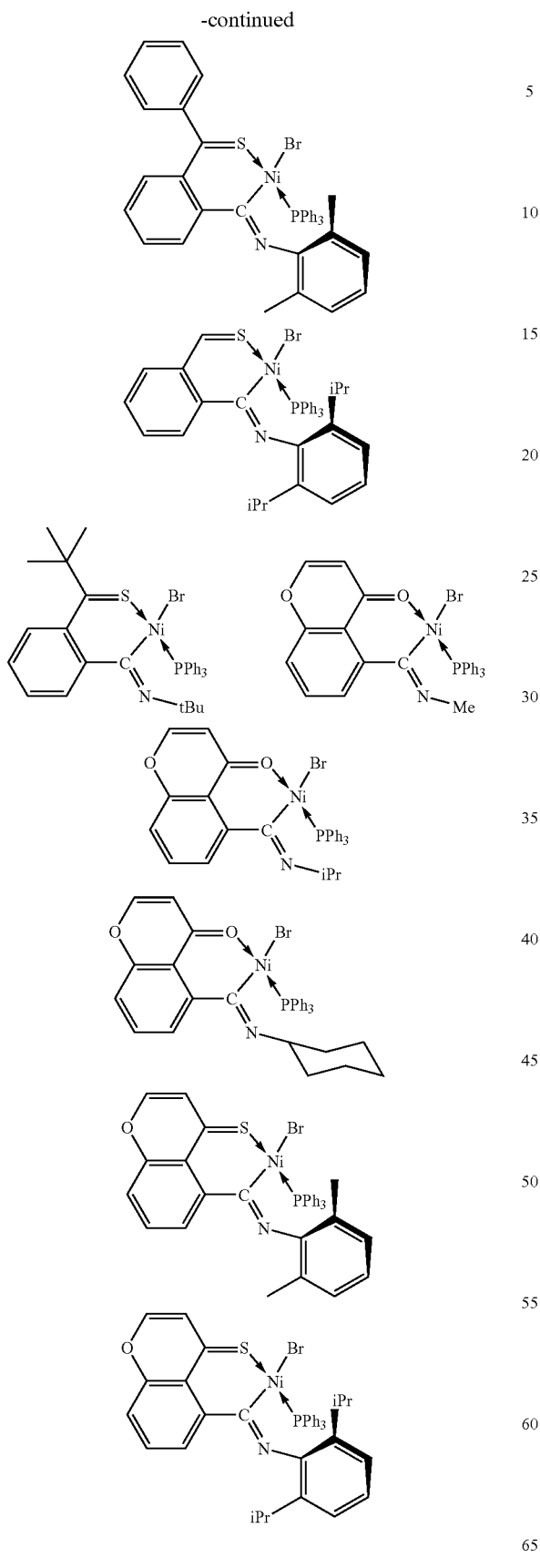
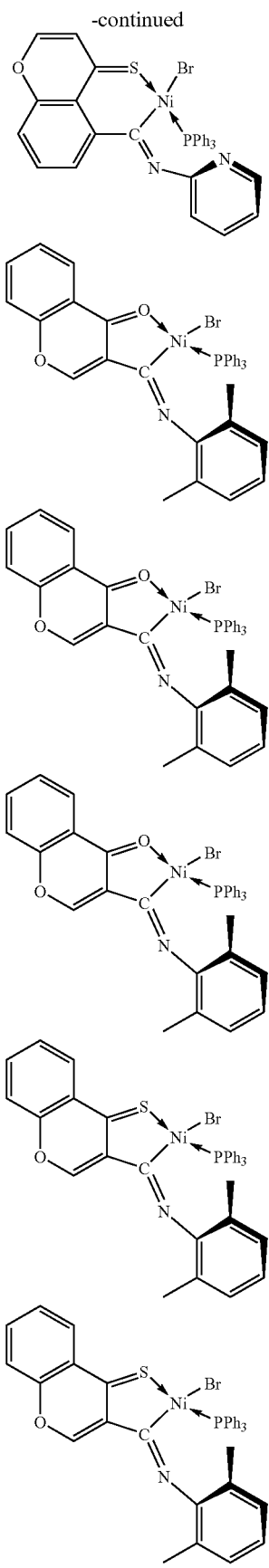

-continued

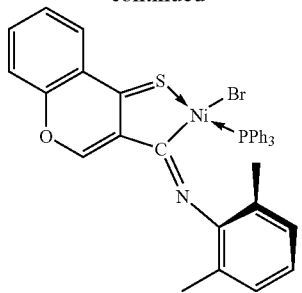

The process for preparing the transition metal compound of formula (5) is not particularly limited, but the transition metal compound of formula (5) can be prepared by the following process.

A ligand precursor represented by the following general tint formula (5-A):

(5-A)

wherein $R^{13}$, $E^5$ and Z are the same as $R^{13}$, $E^5$ and Z, respectively, which are defined for formula (5), and X" represents a hydrogen atom, a substituted silyl group, a substituted stannyl group, a substituted sulfonate group or a halogen atom, is allowed to react with a raw material complex containing a transition metal M wherein M is the same as M defined for formula (5), to give a transition metal compound represented by the following general formula (5-B):

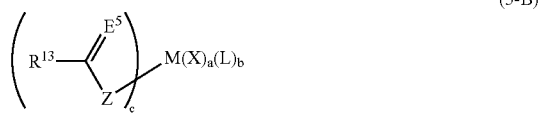
(5-B)

wherein $R^{13}$, $E^5$, Z, M, X, L, a, b and c are the same as $R^{13}$, $E^5$, Z, M, X, L, a, b and c, respectively, which are defined for formula (5). More specifically, X" in the ligand precursor of formula (5-A) is metallized by an-organometal reagent at a low temperature, and the thus-obtained compound is allowed to react with the transition metal-containing raw material complex to give a transition metal compound of formula (5-B). Alternatively, X" in the ligand precursor of formula (5-A) is not metallized, and the ligand precursor of formula (5-A) is allowed to react with a raw material complex which is a transition metal compound having a low valence, whereby oxidative addition of Z-X" bond proceeds to give a transition metal compound of formula (5-B).

The transition metal compound of formula (5-B) is allowed to react with an isocyanide represented by the general formula: C≡N—$R^{12}$ wherein $R^{12}$ is the same as $R^{12}$ defined for formula (5), to give a transition metal compound represented by the general formula (5).

A reaction product of the compound of formula (5-B) with the isocyanide of C≡N—$R^{12}$ can be used as a catalyst ingredient for polymerization of an olefin instead of the transition metal compound of formula (5) without separation of the reaction product.

In formula (6) representing a transition metal compound of the present invention, $R^{14}$ and $R^{15}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for R', $R^2$ and $R^3$ in formula (2). $R^{14}$ and $R^{15}$ may be the same or different. $R^{14}$ and $R^{15}$ may be bonded together to form a ring.

$R^{16}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for $R^1$ in formula (1).

$G^5$ represents an atom of group 15 of the periodic table; Z, M, X, L, a, b and c are the same as Z, M, X, L, a, b and c, respectively, which are defined for formula (1). Two members selected from $R^{14}$, $R^{15}$, $R^{16}$ and Z may be bonded together to form a ring, provided that at least two rings can be formed. X and L may be bonded to each other, L and $R^{14}$ may be bonded to each other, L and $R^{15}$ may be bonded to each other, and L and $R^{16}$ may be bonded to each other.

As specific examples of the transition metal compound represented by formula (6), there can be mentioned compounds represented by the following formulae.

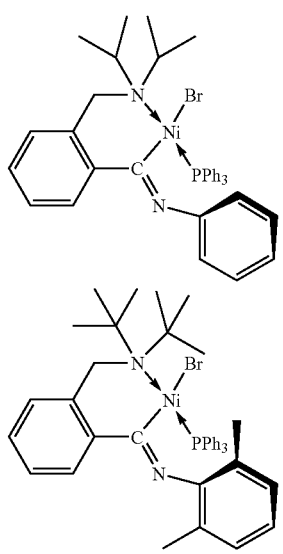

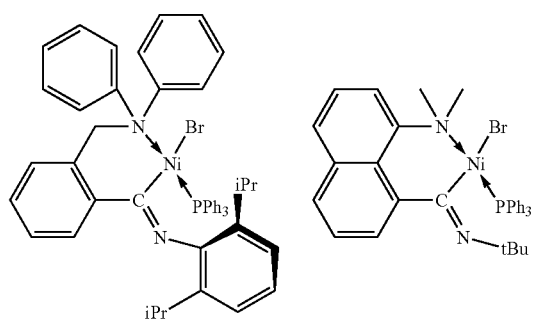
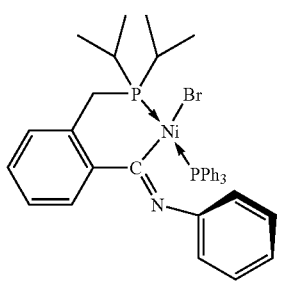
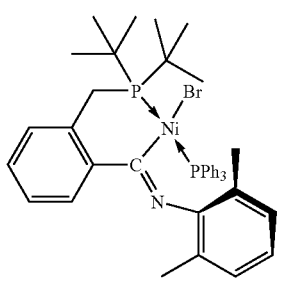
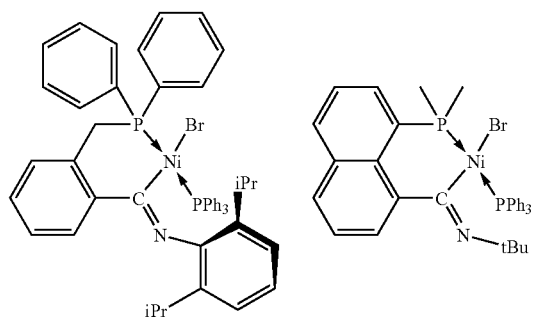
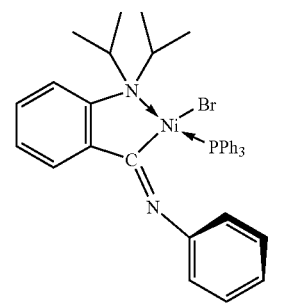
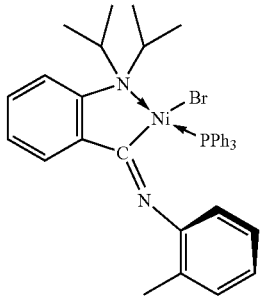
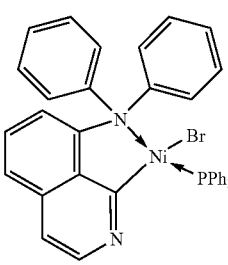
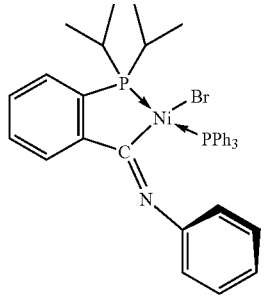
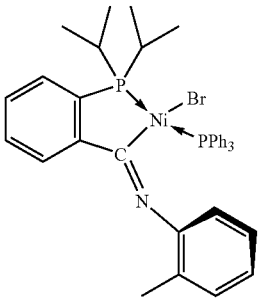
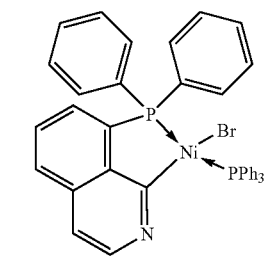
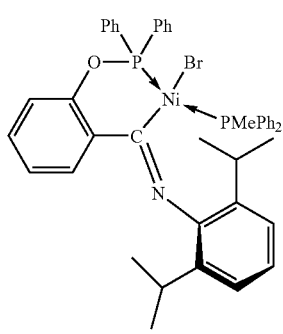
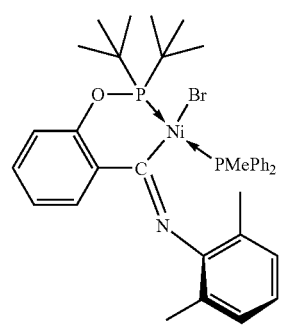

-continued

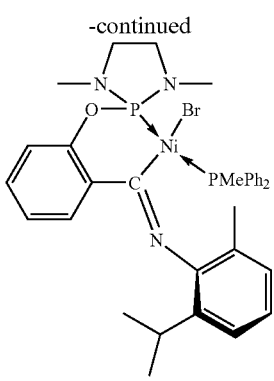

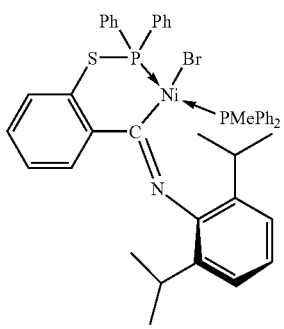

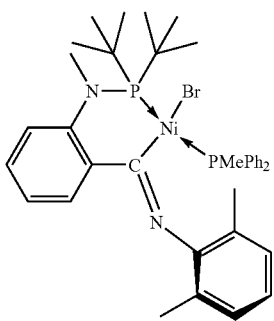

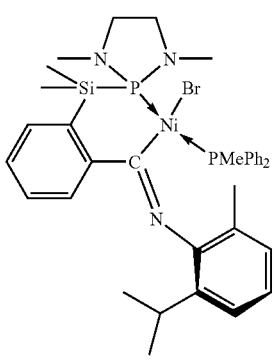

The process for preparing the transition metal compound of formula (6) is not particularly limited, but the transition metal compound of formula (6) can be prepared by the following process.

A ligand precursor represented by the following general formula (6-A):

wherein $R^{14}$, $R^{15}$, $G^5$ and Z are the same as $R^{14}$, $R^{15}$, $G^5$ and Z, respectively, which are defined for formula (6), and X" represents a hydrogen atom, a substituted silyl group, a substituted stannyl group, a substituted sulfonate group or a halogen atom, is allowed to react with a raw material complex containing a transition metal M wherein M is the same as M defined for formula (6), to give a transition metal compound represented by the following general formula (6-B):

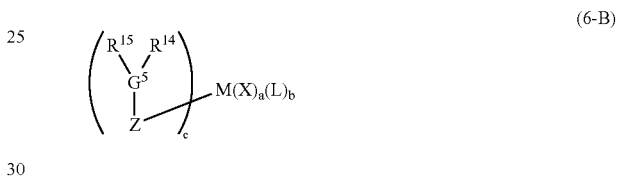

wherein $R^{14}$, $R^{15}$, $G^5$, Z, M, X, L, a, b and c are the same as $R^{14}$, $R^{15}$, $G^5$, Z, M, X, L, a, b and c, respectively, which are defined for formula (6). More specifically, X" in the ligand precursor of formula (6-A) is metallized by an organometal reagent at a low temperature, and the thus-obtained compound is allowed to react with the transition metal-containing raw material complex to give a transition metal compound of formula (6-B). Alternatively, X" in the ligand precursor of formula (6-A) is not metallized, and the ligand precursor of formula (6-A) is allowed to react with a raw material complex which is a transition metal compound having a low valence, whereby oxidative addition of Z-X" bond proceeds to give a transition metal compound of formula (6-B).

The transition metal compound of formula (6-B) is allowed to react with an isocyanide represented by the general formula: C≡N—$R^{16}$ wherein $R^{16}$ is the same as $R^{16}$ defined for formula (6), to give a transition metal compound represented by the general formula (6).

A reaction product of the compound of formula (6-B) with the isocyanide of C≡N—$R^{16}$ can be used as a catalyst ingredient for polymerization of an olefin instead of the transition metal compound of formula (6) without separation of the reaction product.

In formula (7) representing a transition metal compound of the present invention, $R^{17}$ and $R^{18}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for R¹ in formula (1). $R^{17}$ and $R^{18}$ may be the same or different.

$R^{19}$ through $R^{23}$ represent a hydrogen atom, a halogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for R', $R^2$ and $R^3$ in formula (2). As specific examples of the halogen atom, there can be mentioned fluorine, chlorine, bromine and iodine. $R^{19}$ through $R^{23}$ may be the same or different. Two members selected from $R^{17}$ through $R^{23}$ may be bonded together to form a ring, provided that at least two rings can be formed. M, X, L, a, b and c are the same as M, X, L, a, b and c, respectively, which are defined for formula (1). X and L may be bonded to each other, L and $R^{17}$ may be bonded to each other, and L and $R^{18}$ may be bonded to each other.

As specific examples of the transition metal compound represented by formula (7), there can be mentioned compounds represented by the following formulae.

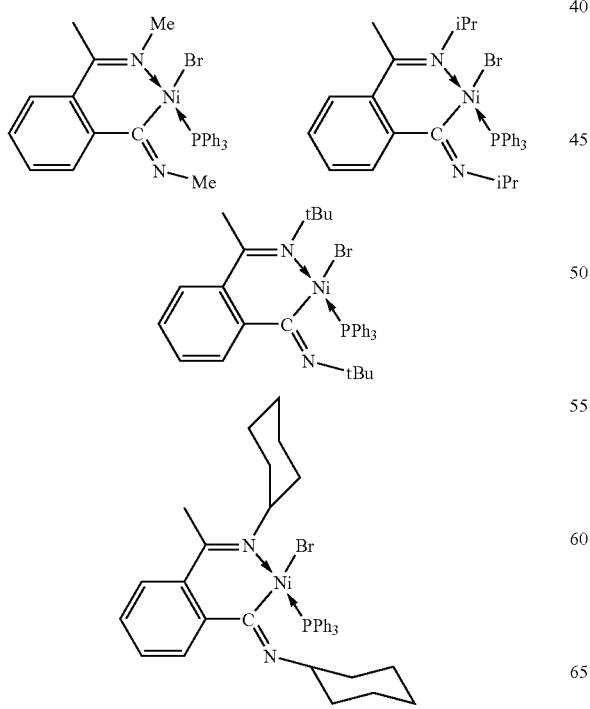

-continued

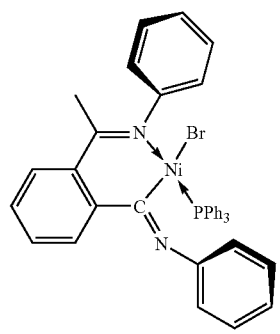

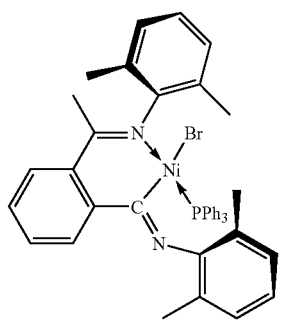

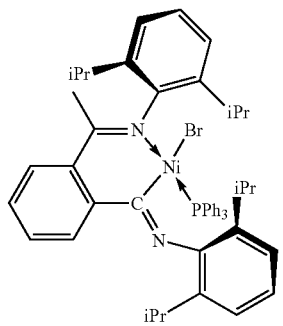

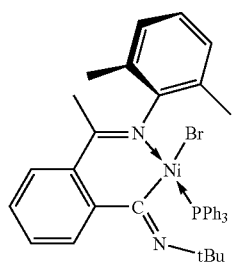

-continued

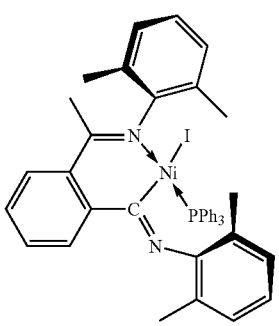

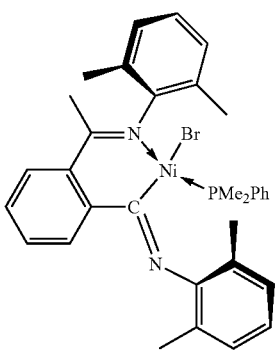

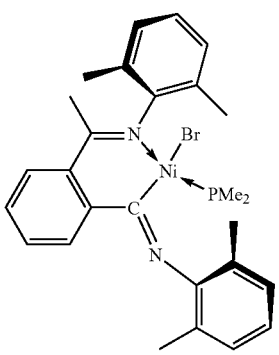

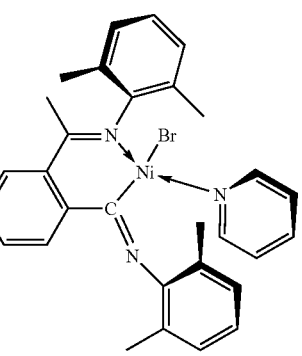

-continued

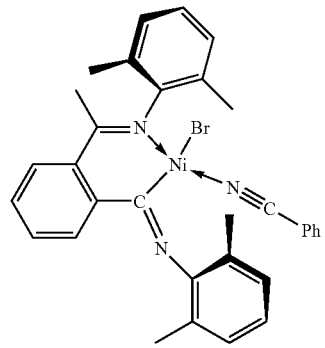

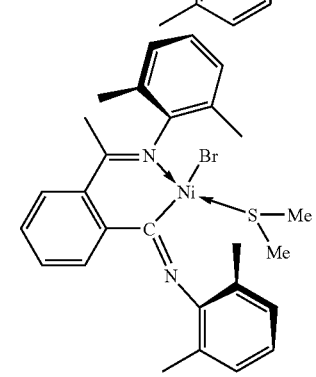

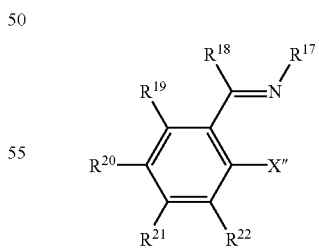

The process for preparing the transition metal compound of formula (7) is not particularly limited, but the transition metal compound of formula (7) can be prepared by the following process.

A ligand precursor represented by the following general formula (7-A):

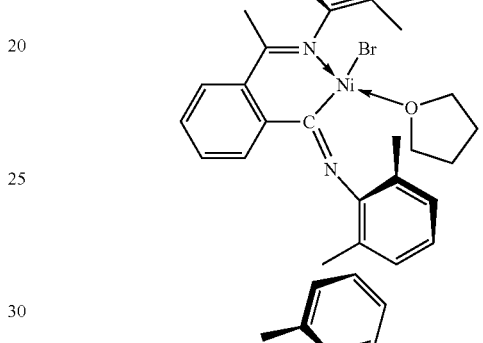

wherein $R^{17}$ and $R^{19}$ through $R^{23}$ are the same as $R^{17}$ and $R^{19}$ through $R^{23}$, respectively, which are defined for formula (7), and X" represents a hydrogen atom, a substituted silyl group, a substituted stannyl group, a substituted sulfonate group or a halogen atom, is allowed to react with a raw material complex containing a transition metal M wherein M is the same as M defined for formula (7), to give a transition metal compound represented by the following general formula (7-B):

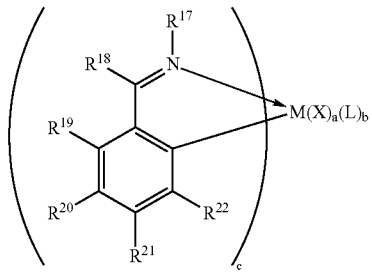

wherein $R^{17}$, $R^{19}$ through $R^{23}$, M, X, L, a, b and c are the same as $R^{17}$, $R^{19}$ through $R^{23}$, M, X, L, a, b and c, respectively, which are defined for formula (7). More specifically, X" in the ligand precursor of formula (7-A) is metallized by an organometal reagent at a low temperature, and the thus-obtained compound is allowed to react with the transition metal-containing raw material complex to give a transition metal compound of formula (7-B). Alternatively, X" in the ligand precursor of formula (7-A) is not metallized, and the ligand precursor of formula (7-A) is allowed to react with a raw material complex which is a transition metal compound having a low valence, whereby oxidative addition of C—X" bond proceeds to give a transition metal compound of formula (7-B).

The transition metal compound of formula (7-B) is allowed to react with an isocyanide represented by the general formula: $C\equiv N-R^{18}$ wherein $R^{18}$ is the same as $R^{18}$ defined for formula (7), to give a transition metal compound represented by the general formula (7).

A reaction product of the compound of formula (7-B) with the isocyanide of $C\equiv N-R^{18}$ can be used as a catalyst ingredient for polymerization of an olefin instead of the transition metal compound of formula (7) without separation of the reaction product.

In formula (8) representing a transition metal compound of the present invention, $R^{24}$ through $R^{27}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for $R^1$ in formula (1). M, X, L, A, X', L', a, b, c, d and e are the same as M, X, L, A, X', L', a, b, c, d and e, respectively, which are defined for formula (1).

As specific examples of the transition metal compound represented by formula (8), there can be mentioned compounds represented by the following formulae.

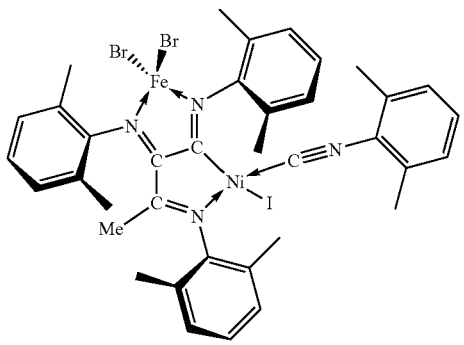

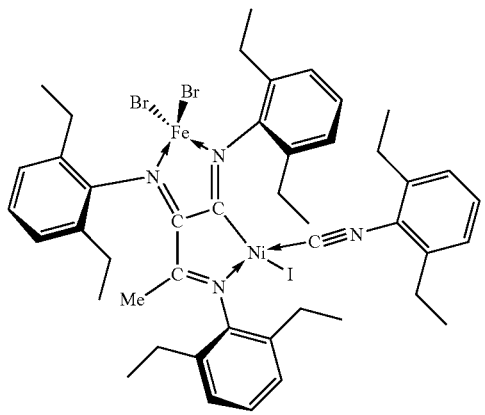

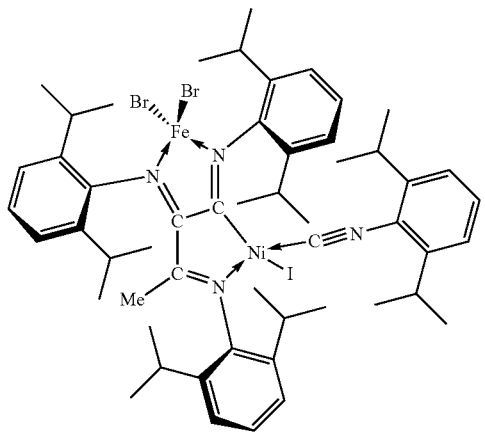

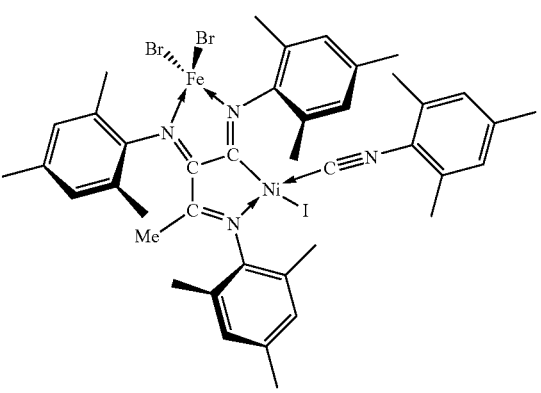

-continued
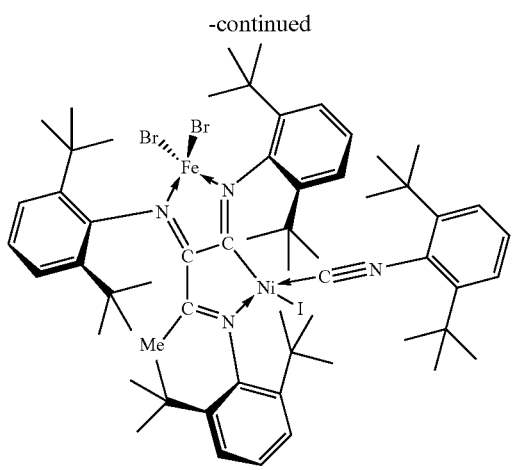
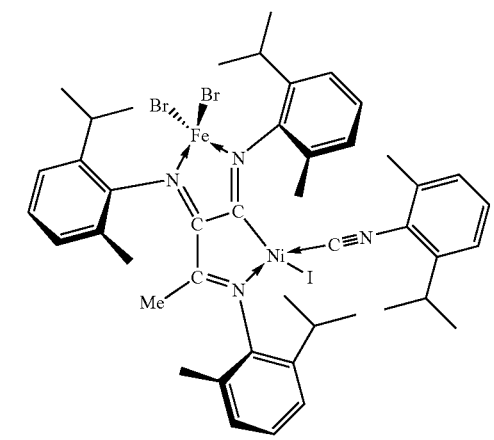
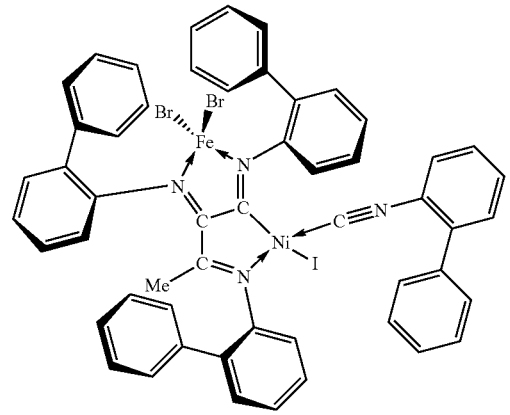
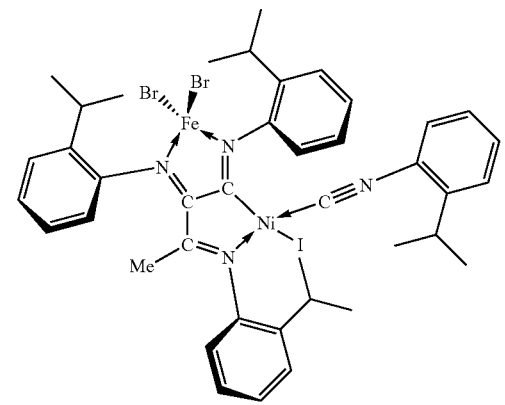
-continued
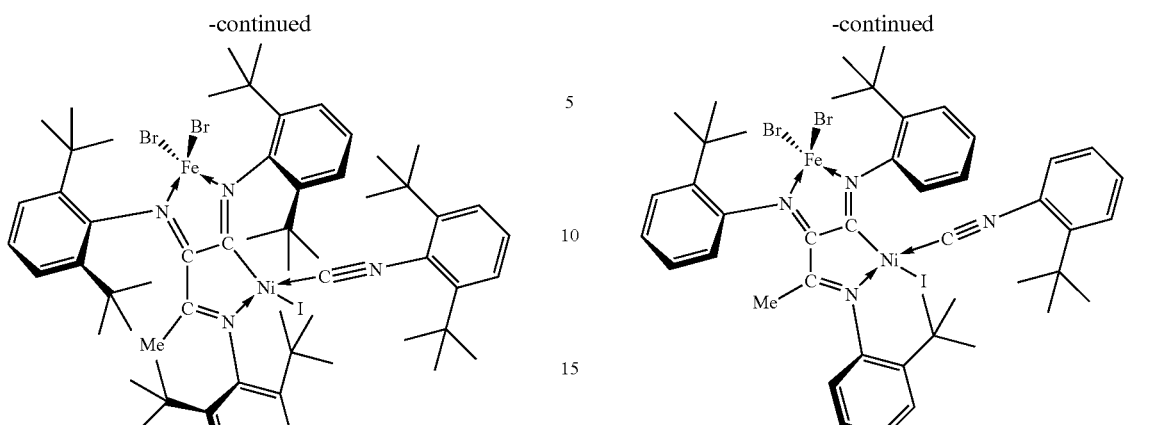
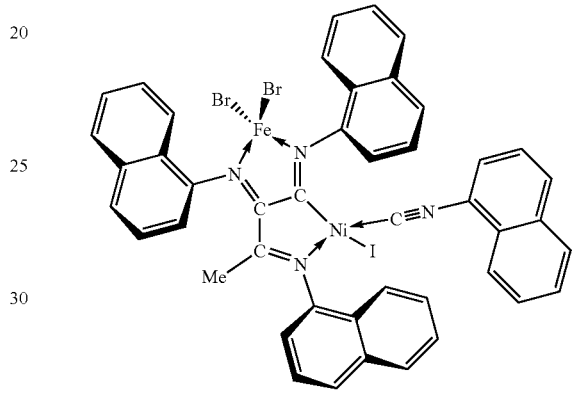
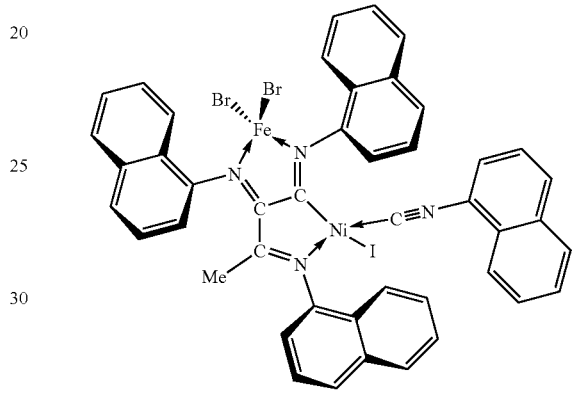
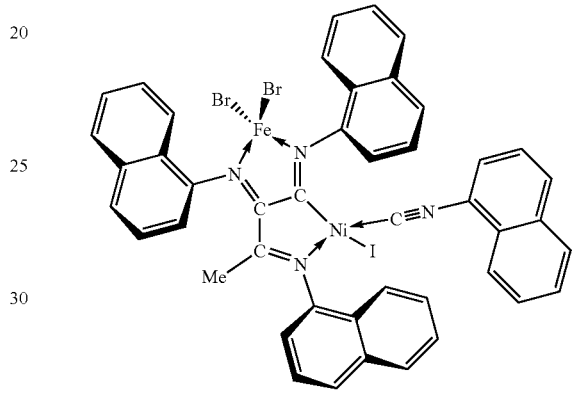
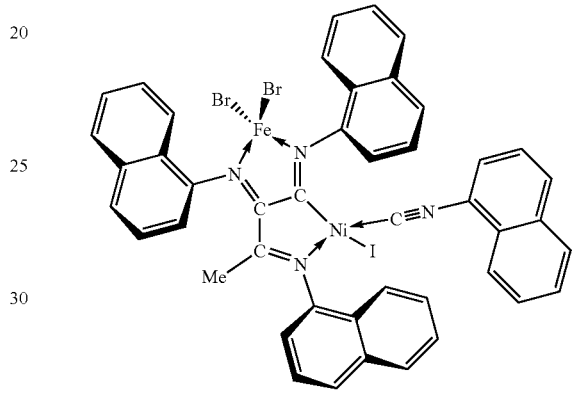

-continued
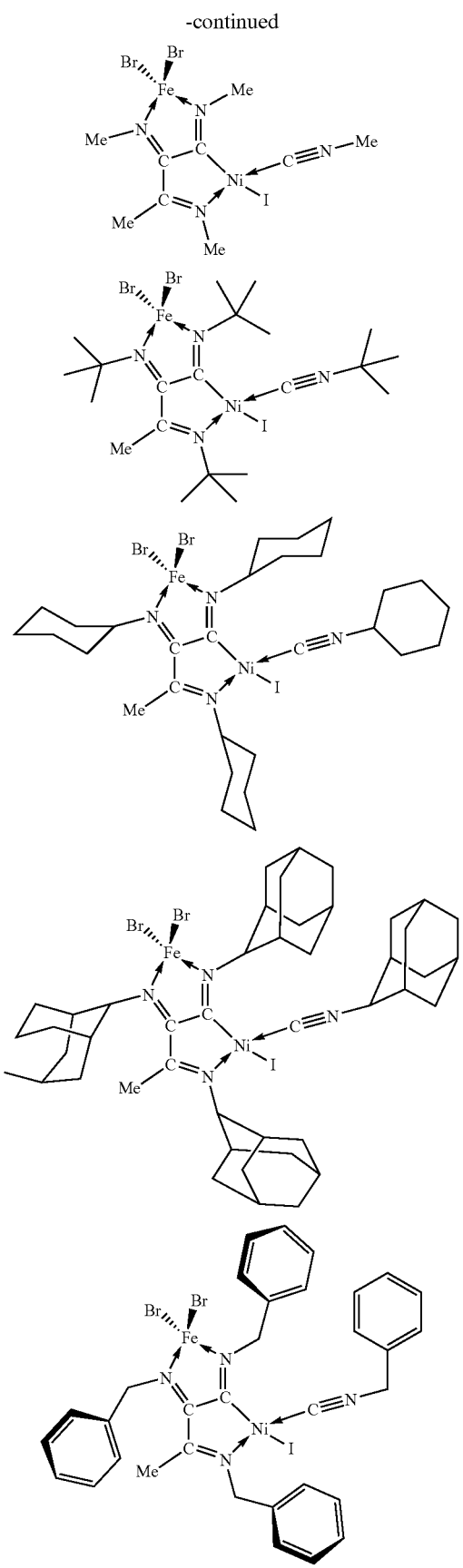
-continued
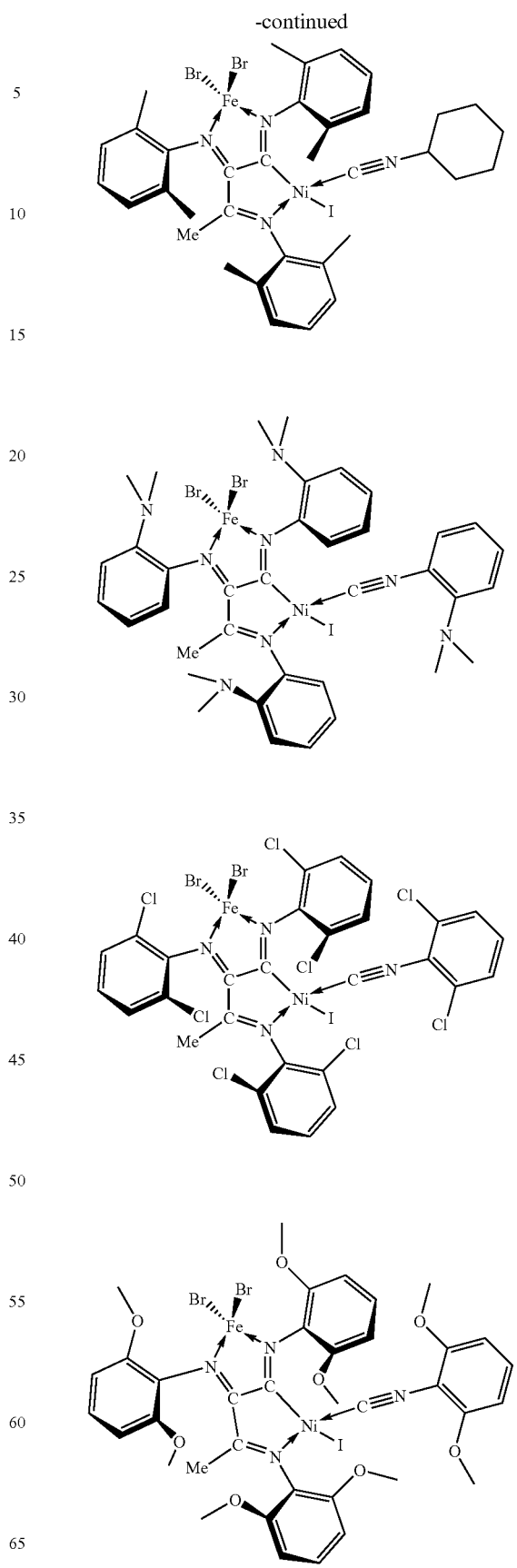

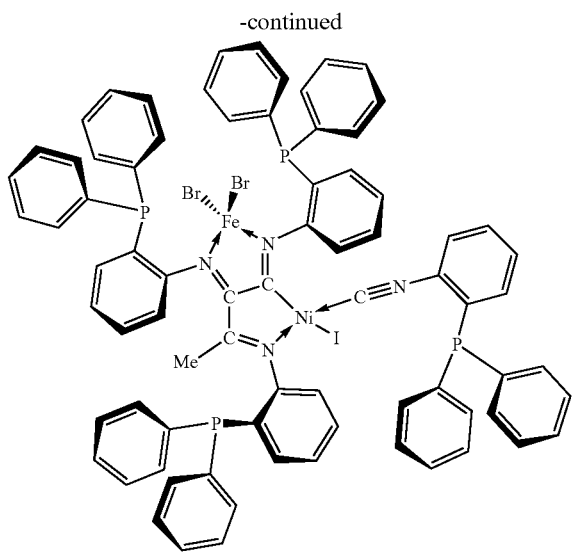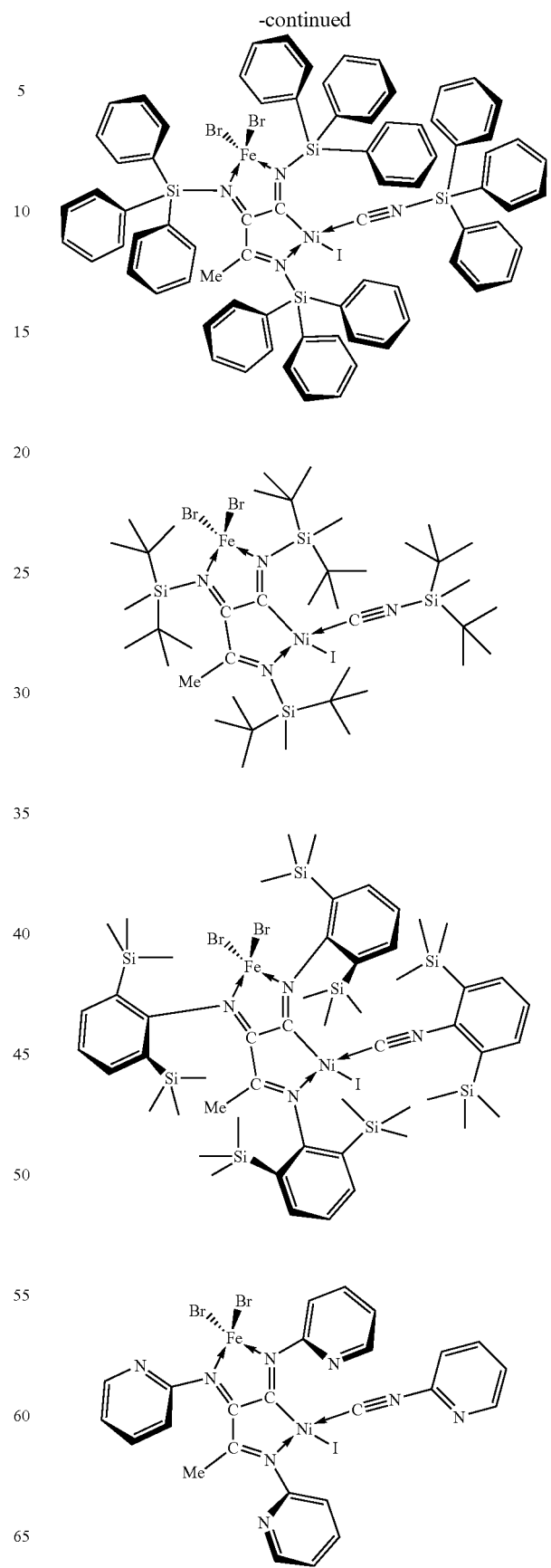

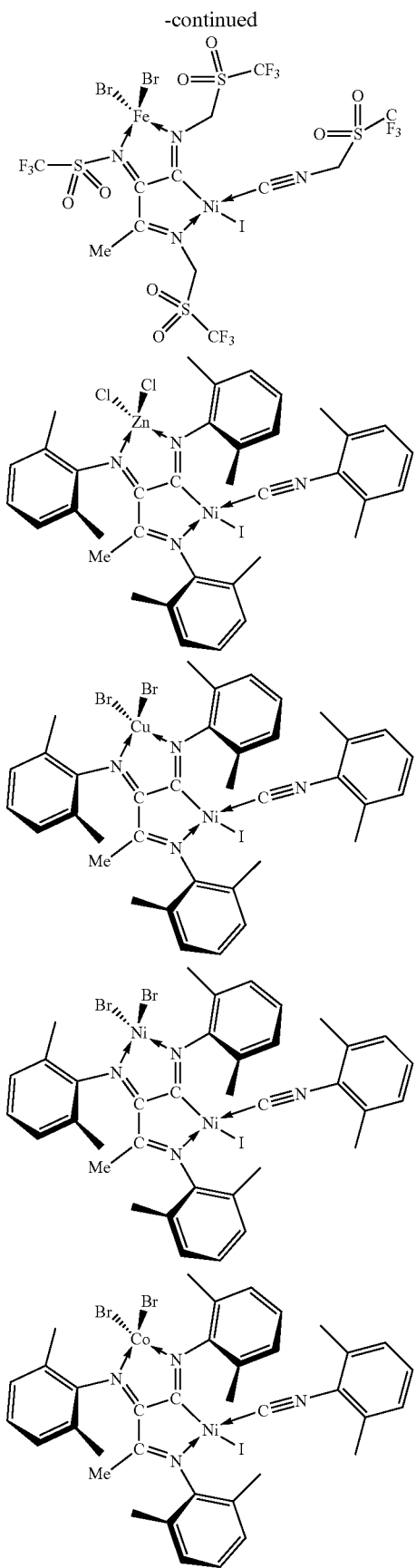
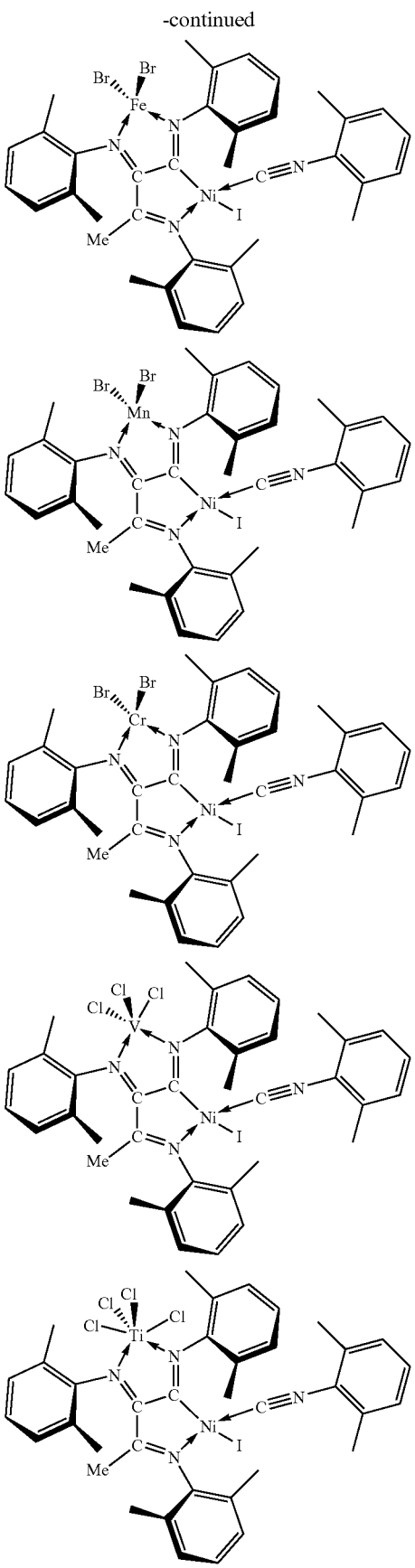

-continued
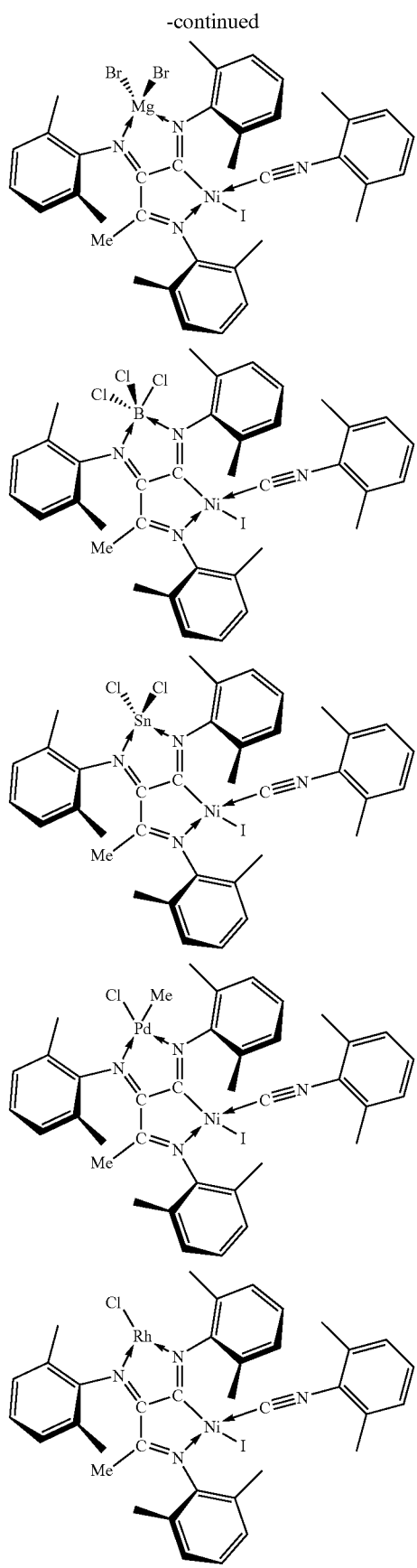
-continued
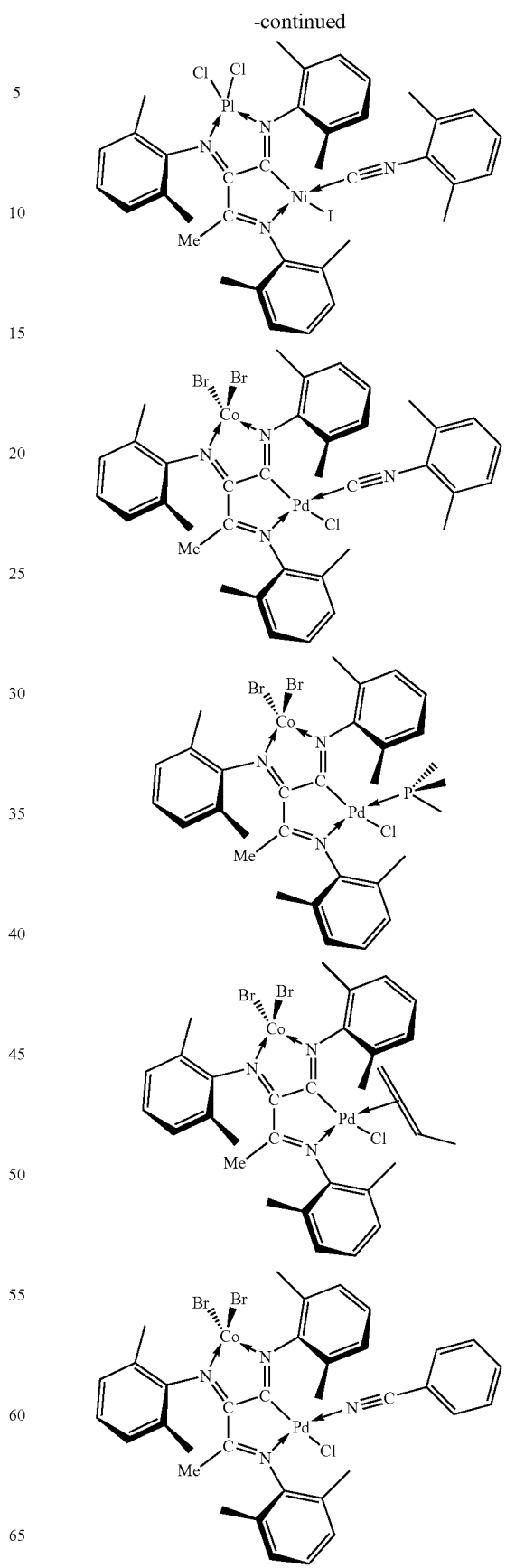

75
-continued
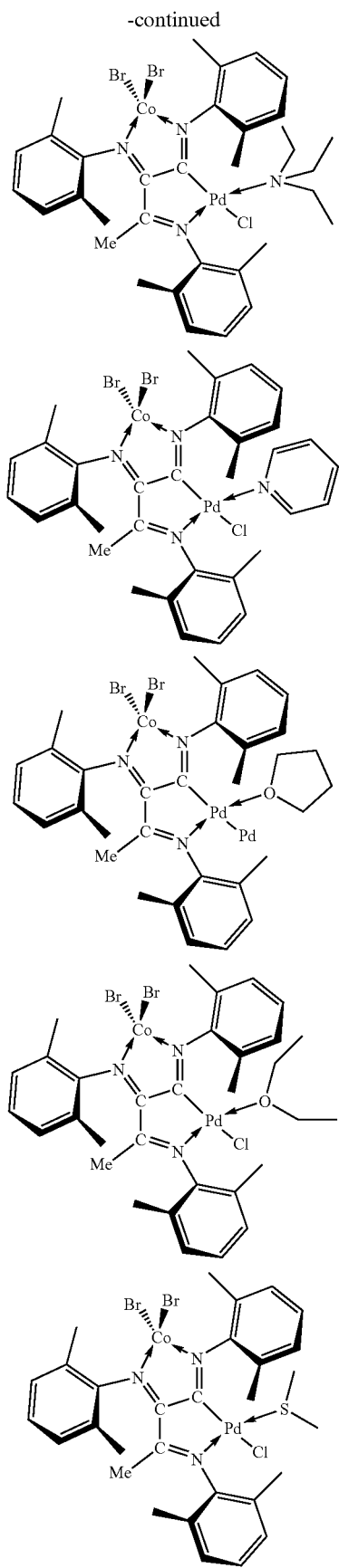
76
-continued
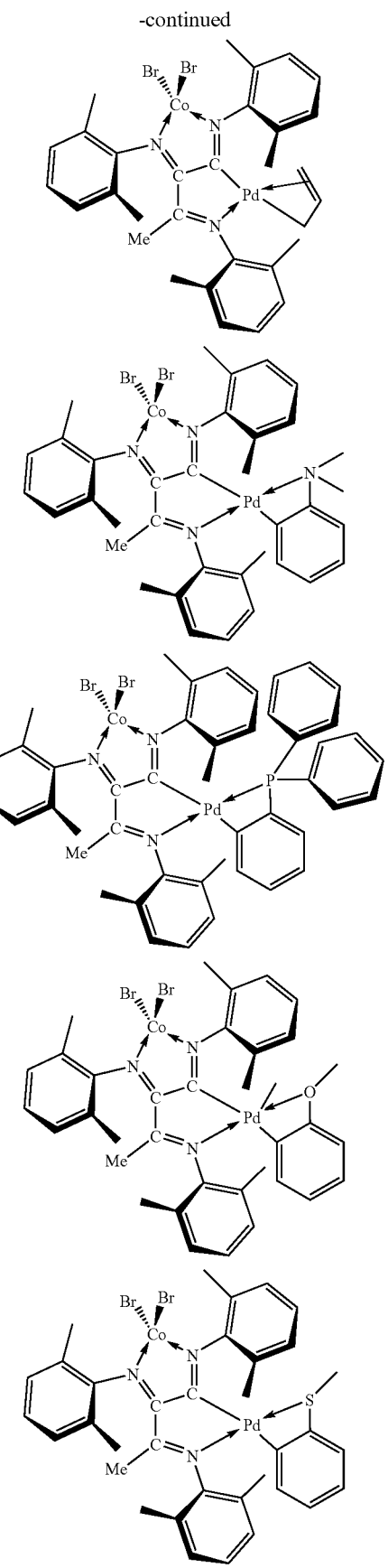

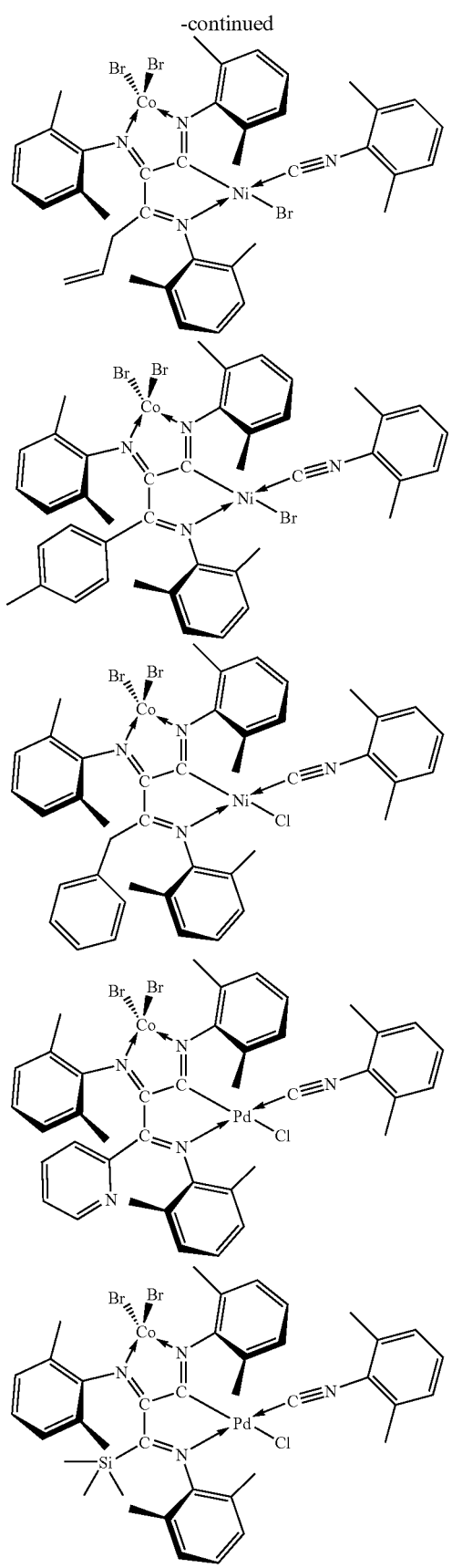

-continued

The process for preparing the transition metal compound of formula (8) is not particularly limited, but the transition metal compound of formula (8) can be prepared by the following process.

A transition metal compound represented by the following general formula (8-A):

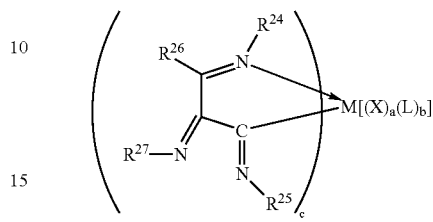

wherein $R^{24}$ through $R^{27}$, M, X, L, a, b and c are the same as $R^{24}$ through $R^{27}$, M, X, L, a, b and c, respectively, which are defined for formula (8), is allowed to react with a compound represented by the following formula: A(X')d(L')e wherein A, X', L', d and e are the same as A, X', L', d and e, respectively, which are defined for formula (8) to give the transition metal compound of formula (8). The transition metal compound of formula (8-A) can be synthesized by a conventional complex synthesizing process as described in, for example, Organometallic Chemistry, vol.11, 21–86, and J. Am. Chem. Soc., 91, 7196(1969). A reaction product of the compound of formula (8-A) with the compound of formula A(X')d(L')e can be used as a catalyst ingredient for polymerization of an olefin instead of the transition metal compound of formula (8) without separation of the reaction product.

In formula (9) representing a transition metal compound of the present invention, $R^{28}$, $R^{29}$ and $R^{31}$ through $R^{34}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for R', $R^2$ and $R^3$ in formula (2).

$R^{30}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for $R^1$ in formula (1).

M, X, L, a, b and c are the same as M, X, L, a, b and c, respectively, which are defined for formula (1). X and L may be bonded to each other, L and $R^{28}$ may bg bonded to each other, L and $R^{29}$ may be bonded to each other, and L and $R^{30}$ may be bonded to each other.

As specific examples of the transition metal compound represented by formula (9), there can be mentioned compounds represented by the following formulae.
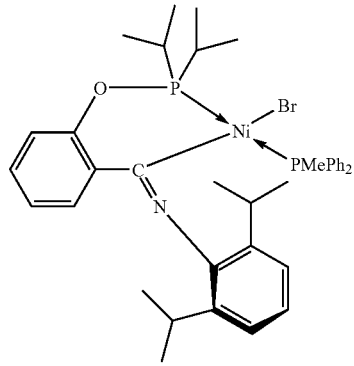
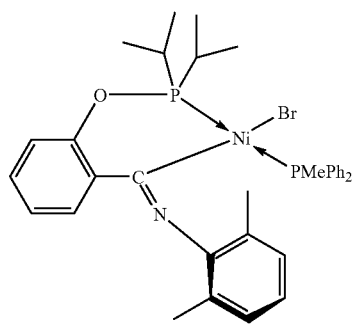
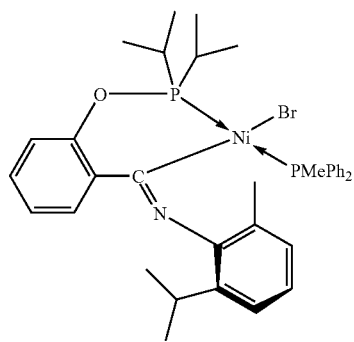
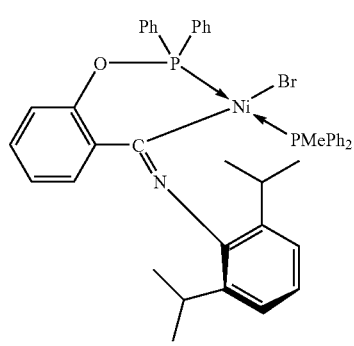
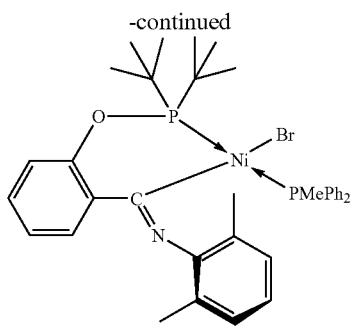
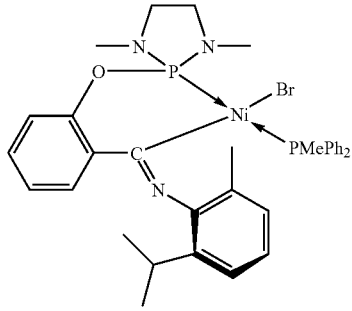
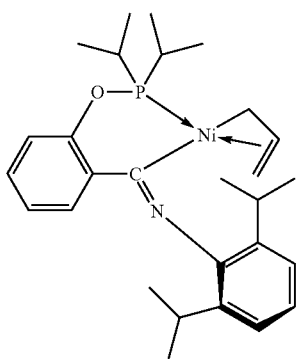
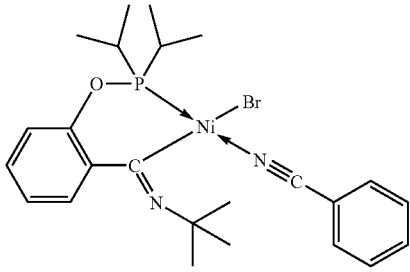
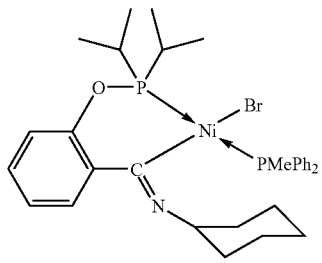
The process for preparing the transition metal compound of formula (9) is not particularly limited, but the transition metal compound of formula (9) can be prepared by the following process.

A ligand precursor represented by the following general formula (9-A):

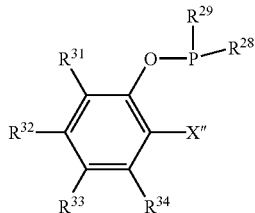

wherein $R^{28}$, $R^{29}$ and $R^{31}$ through $R^{34}$ are the same as $R^{28}$, $R^{29}$ and $R^{31}$ through $R^{34}$, respectively, which are defined for formula (9), and X″ represents a hydrogen atom, a substituted silyl group, a substituted stannyl group, a substituted sulfonate group or a halogen atom, is allowed to react with a raw material complex containing a transition metal M wherein M is the same as M defined for formula (9), to give a transition metal compound represented by the following general formula (9-B):

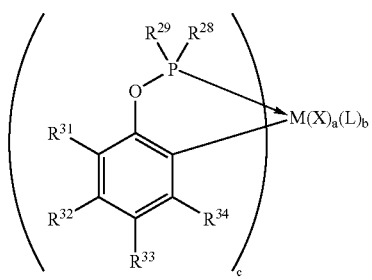

wherein $R^{28}$, $R^{29}$ and $R^{31}$ through $R^{34}$, M, X, L, a, b and c are the same as $R^{28}$, $R^{29}$ and $R^{31}$ through $R^{34}$, M, X, L, a, b and c, respectively, which are defined for formula (9). More specifically, X″ in the ligand precursor of formula (9-A) is metallized by an organometal reagent at a low temperature, and the thus-obtained compound is allowed to react with the transition metal-containing raw material complex to give a transition metal compound of formula (9-B). Alternatively, X″ in the ligand precursor of formula (9-A) is not metallized, and the ligand precursor of formula (9-A) is allowed to react with a raw material complex which is a transition metal compound having a low valence, whereby oxidative addition of C—X″ bond proceeds to give a transition metal compound of formula (9-B).

The transition metal compound of formula (9-B) is allowed to react with an isocyanide represented by the general formula: C≡N—$R^{30}$ wherein $R^{30}$ is the same as $R^{30}$ defined for formula (9), to give a transition metal compound represented by the general formula (9).

A reaction product of the compound of formula (9-B) with the isocyanide of C≡N—$R^{30}$ can be used as a catalyst ingredient for polymerization of an olefin instead of the transition metal compound of formula (9) without separation of the reaction product.

The transition metal compound used as an ingredient of a catalyst for polymerization of an olefin in the present invention includes transition metal compounds represented by the following formulae (10), (11), (12), (13) and (14).

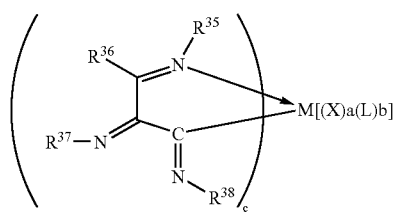

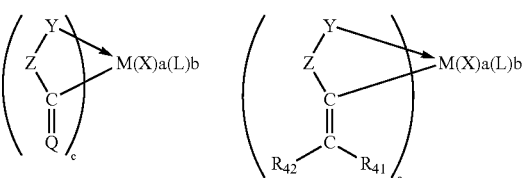

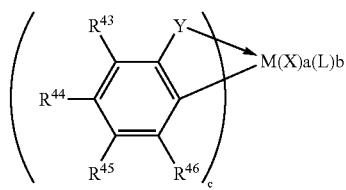

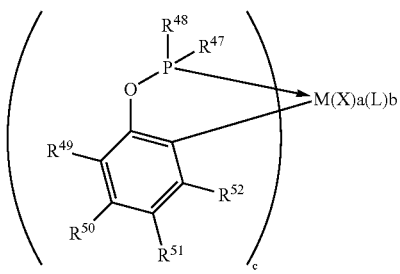

In formula (10), $R^{35}$ through $R^{38}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 30 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for $R^1$ in formula (1). M, X, L, a, b and c are the same as M, X, L, a, b and c, respectively, which are defined for formula (1).

As specific examples of the transition metal compound represented by formula (10), there can be mentioned compounds represented by the following formulae.

-continued

85
-continued
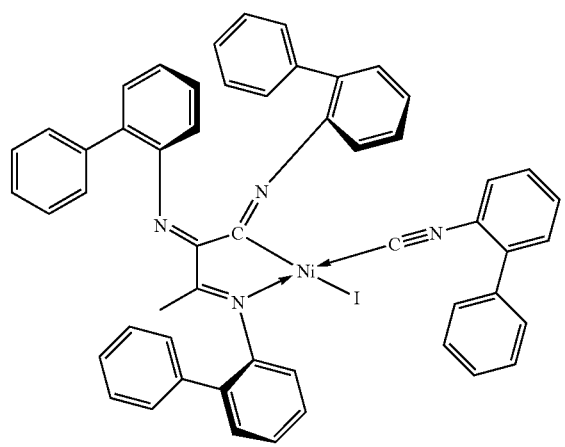
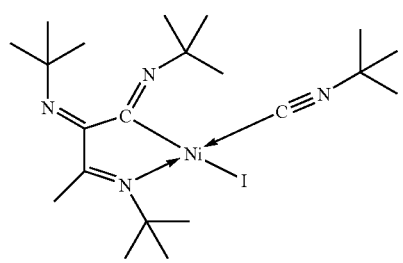
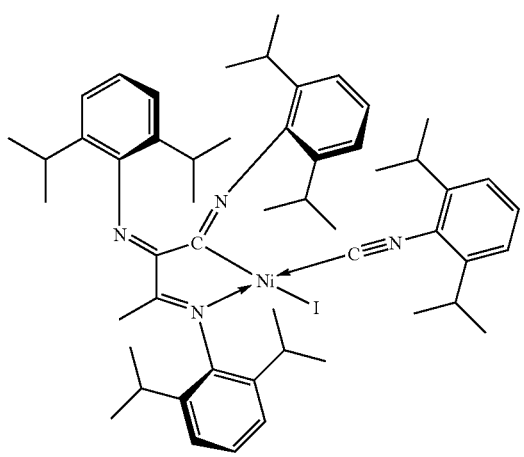
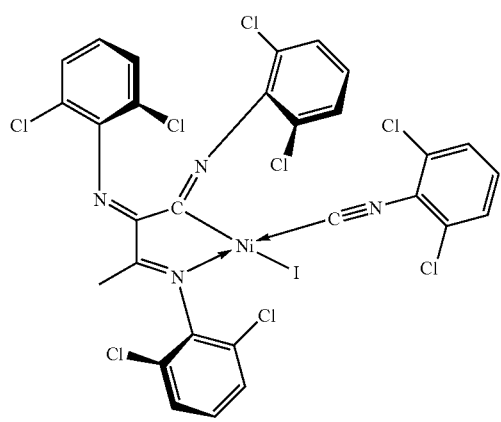
86
-continued
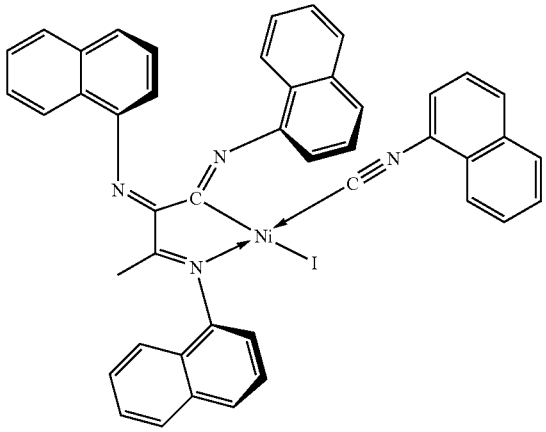
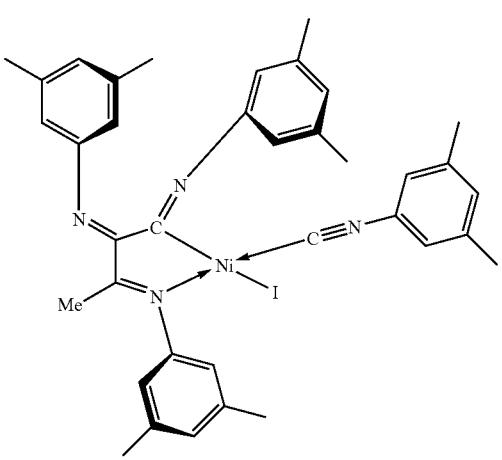
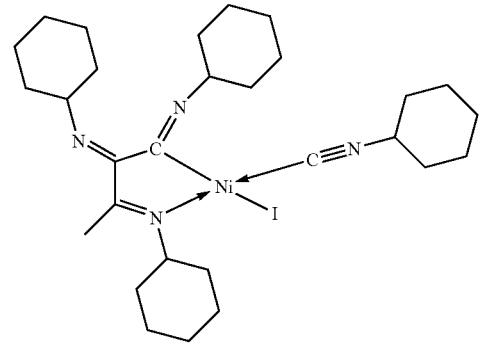
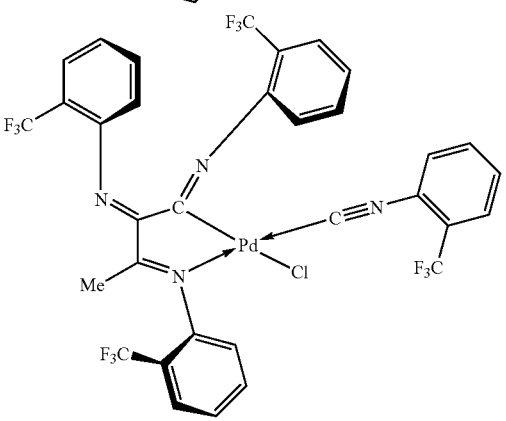

-continued
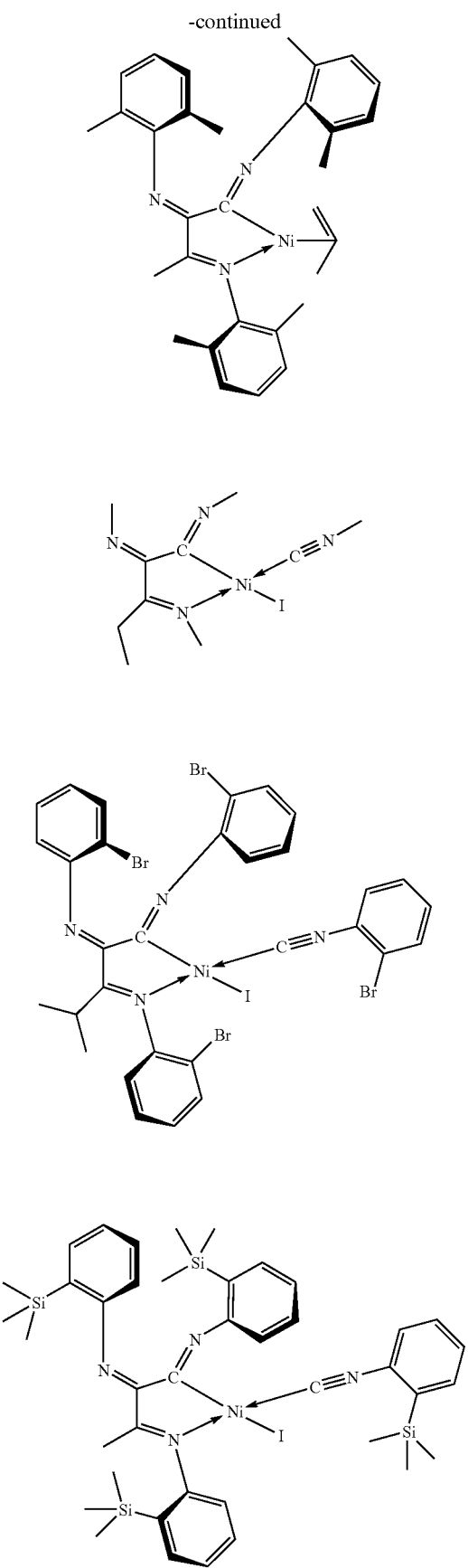
-continued
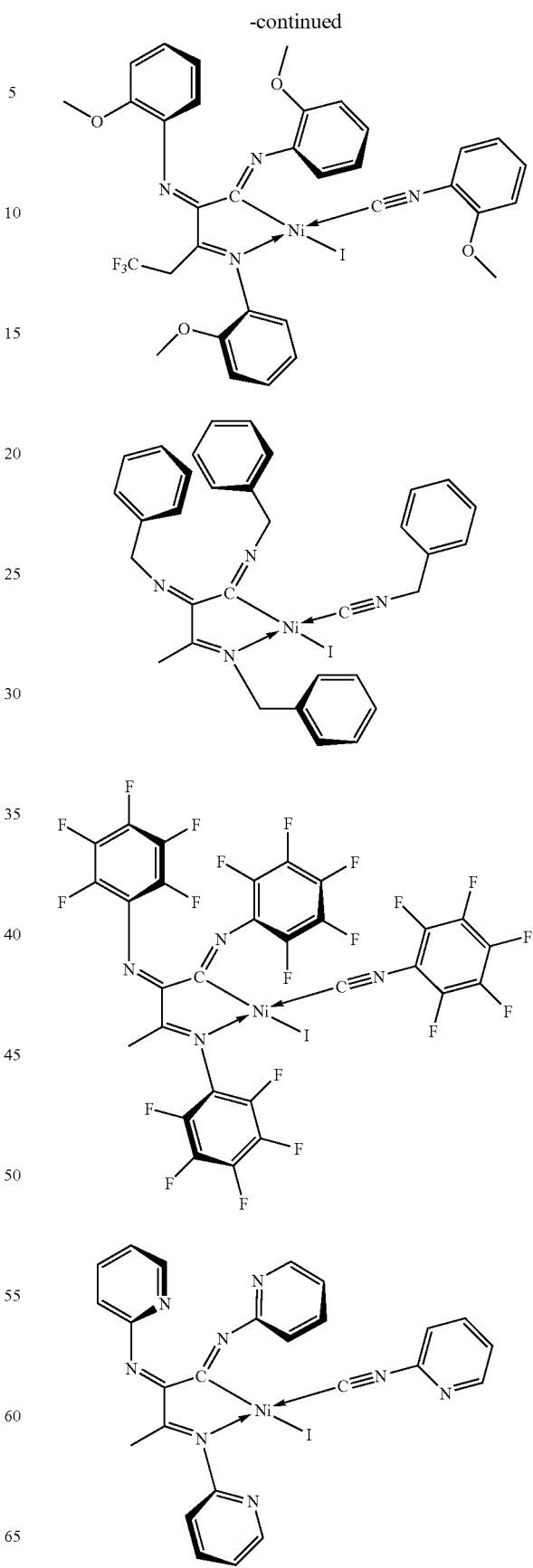

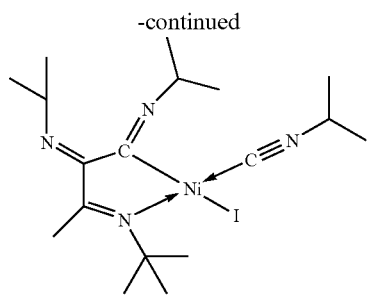

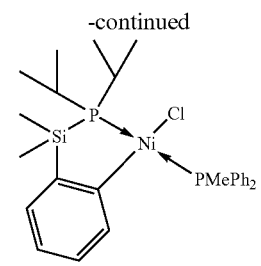

The process for preparing the transition metal compound of formula (10) is not particularly limited. For example, the transition metal compound of formula (10) can be prepared by a process as described in, for example, Organometallic Chemistry, vol. 11, 21–86, and J. Am. Chem. Soc., 91, 7196(1969). The transition metal compound as-produced by the above process can be used without separation as a catalyst ingredient for in-situ polymerization of an olefin.

In formula (11), Q represents an element of group 16 of the periodic table or $C(R^{39})(R^{40})$ wherein $R^{39}$ and $R^{40}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for R', $R^2$ and $R^3$ in formula (2). Z, Y, M, X, L, a, b and c are the same as Z, Y, M, X, L, a, b and c, respectively, which are defined for formula (1). Two members selected from Q, Z and Y may be bonded together to form a ring. X and L may be bonded to each other, and L and Y may be bonded to each other.

As specific examples of the transition metal compound represented by formula (11), there can be mentioned compounds represented by the following formulae.

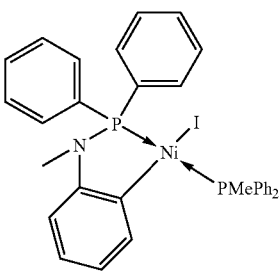

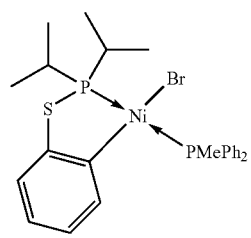 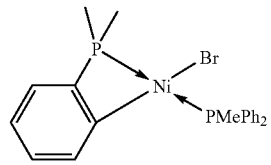

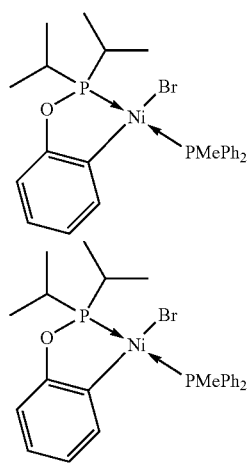 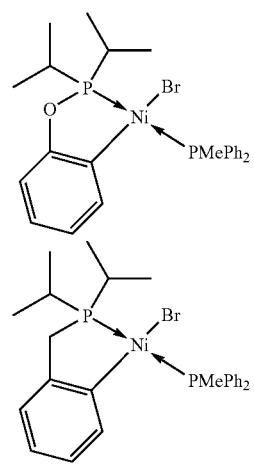

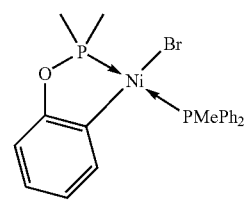 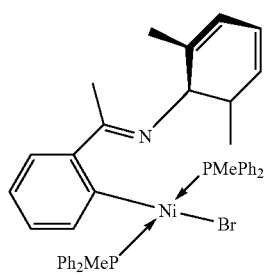

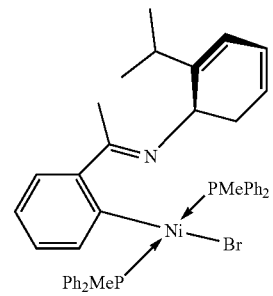

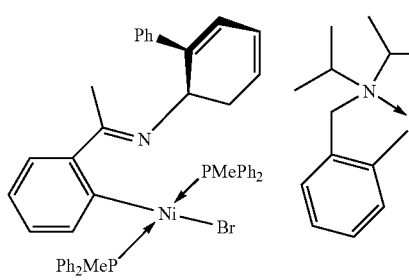

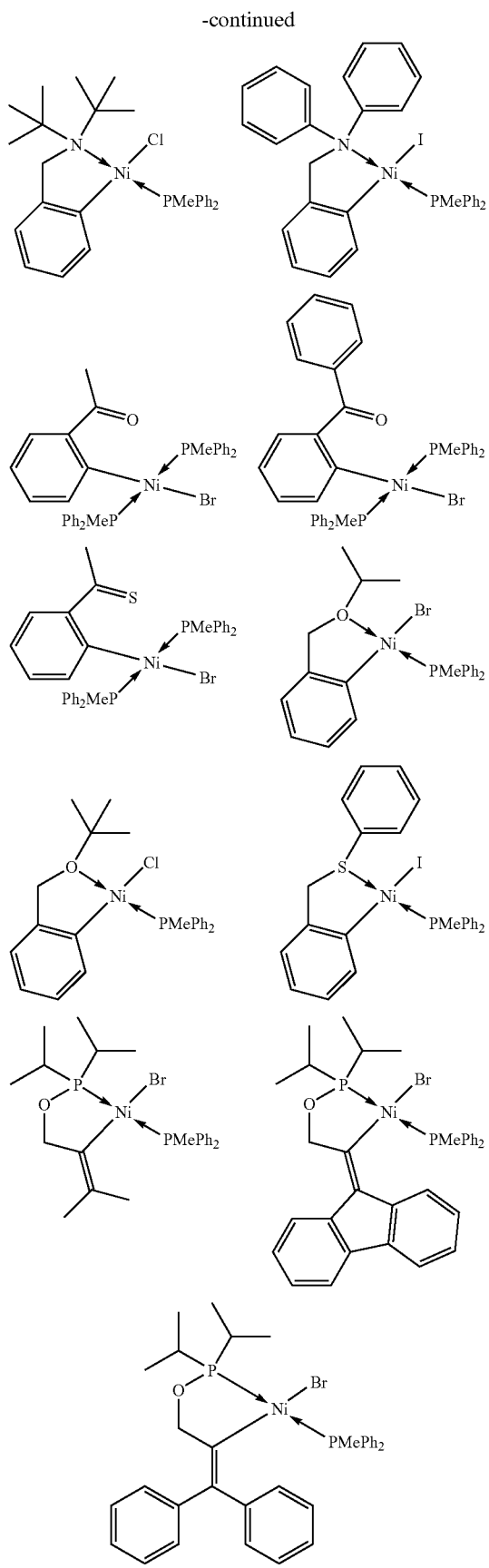

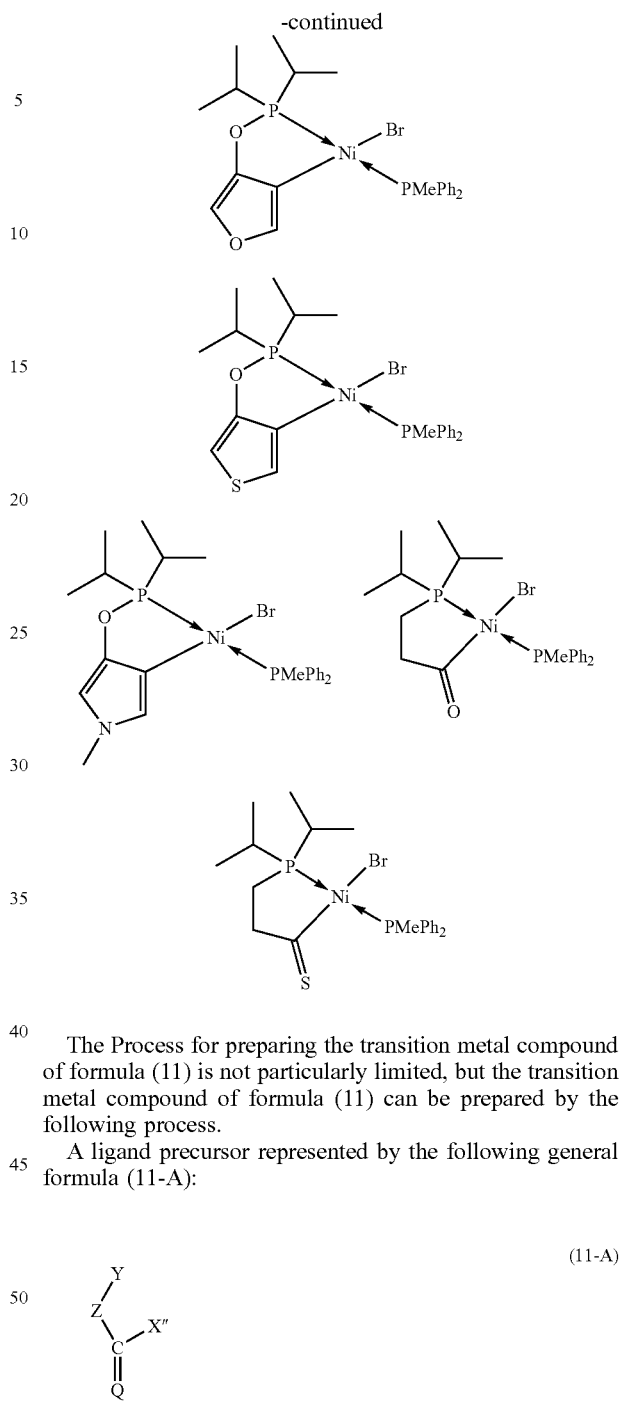

The Process for preparing the transition metal compound of formula (11) is not particularly limited, but the transition metal compound of formula (11) can be prepared by the following process.

A ligand precursor represented by the following general formula (11-A):

(11-A)

wherein Y, Z and Q are the same as Y, Z and Q, respectively, which are defined for formula (11) and X" represents a hydrogen atom, a substituted silyl group, a substituted stannyl group, a substituted sulfonate group or a halogen atom, is allowed to react with a raw material complex containing a transition metal M wherein M is the same as M defined for formula (11), to give the transition metal compound of formula (11). More specifically, X" in the ligand precursor of formula (11-A) is metallized by an organometal reagent at a low temperature, and the thus-obtained compound is allowed to react with the transition metal-containing raw material complex to give a transition metal compound of formula (11-B). Alternatively, X" in the ligand precursor of formula (11-A) is not metallized, and the ligand precursor of formula (11-A) is allowed to react with a raw material complex which is a transition metal compound having a low valence, whereby oxidative addition of C—X" bond proceeds to give a transition metal compound of formula (11-B).

A reaction product of the ligand precursor of formula (11-A) with the raw material complex can be used without separation as a catalyst ingredient for polymerization of an olefin instead of the transition metal compound of formula (11).

In formula (12), $R^{41}$ and $R^{42}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of group 15 or group 16 of the periodic table or a halogen atom. As specific examples of the hydrocarbon group having 1 to 20 carbon atoms, the substituted silyl group, the substituted amide group, the substituted alkoxy group, the substituted aryloxy group, and the hydrocarbon group containing a substituted silyl group, an atom of group 15 or group 16 of the periodic table or a halogen atom, there can be mentioned those groups which are hereinbefore recited for R', $R^2$ and $R^3$ in formula (2). $R^{41}$ and $R^{42}$ may be the same or different. Z, Y, M, X, L, a, b and c are the same as Z, Y, M, X, L, a, b and c, respectively, which are defined for formula (1). Two members selected from $R^{41}$, $R^{42}$, Z and Y may be bonded together to form a ring, provided that at least two rings can be formed. X and L may be bonded to each other, L and $R^{41}$ may be bonded to each other, L and $R^{42}$ may be bonded to each other, and L and Y may be bonded to each other.

As specific examples of the transition metal compound represented by formula (12), there can be mentioned compounds represented by the following formulae.

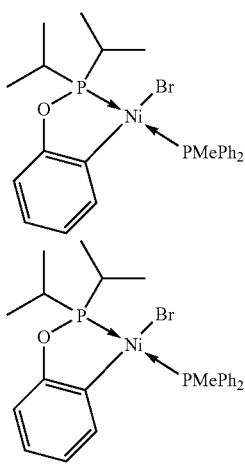

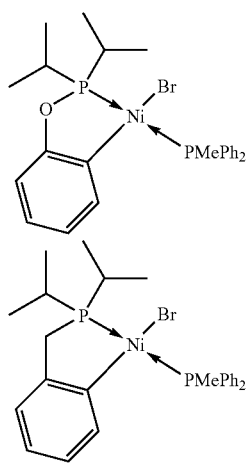

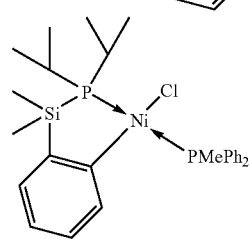

-continued

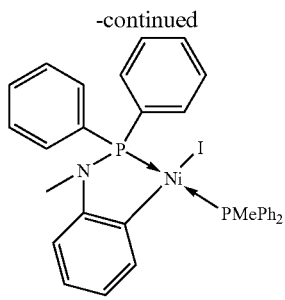

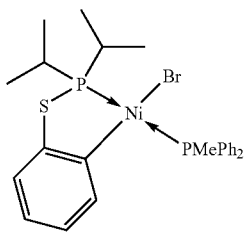 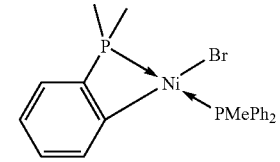

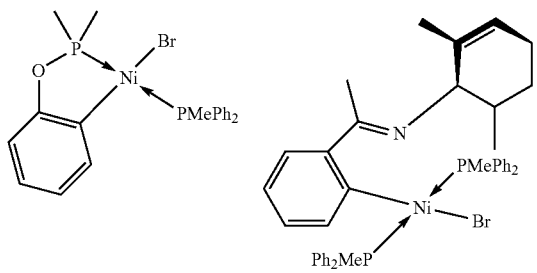

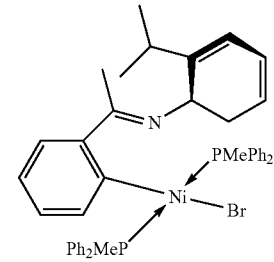

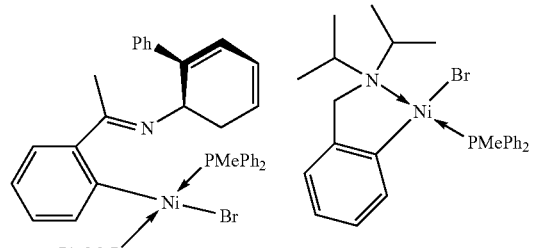

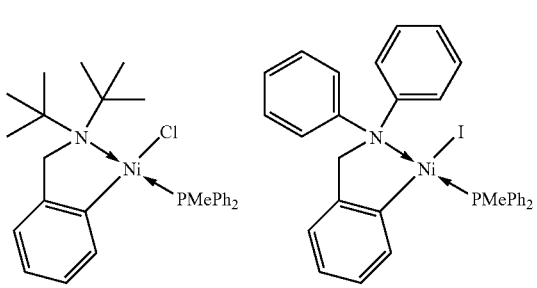

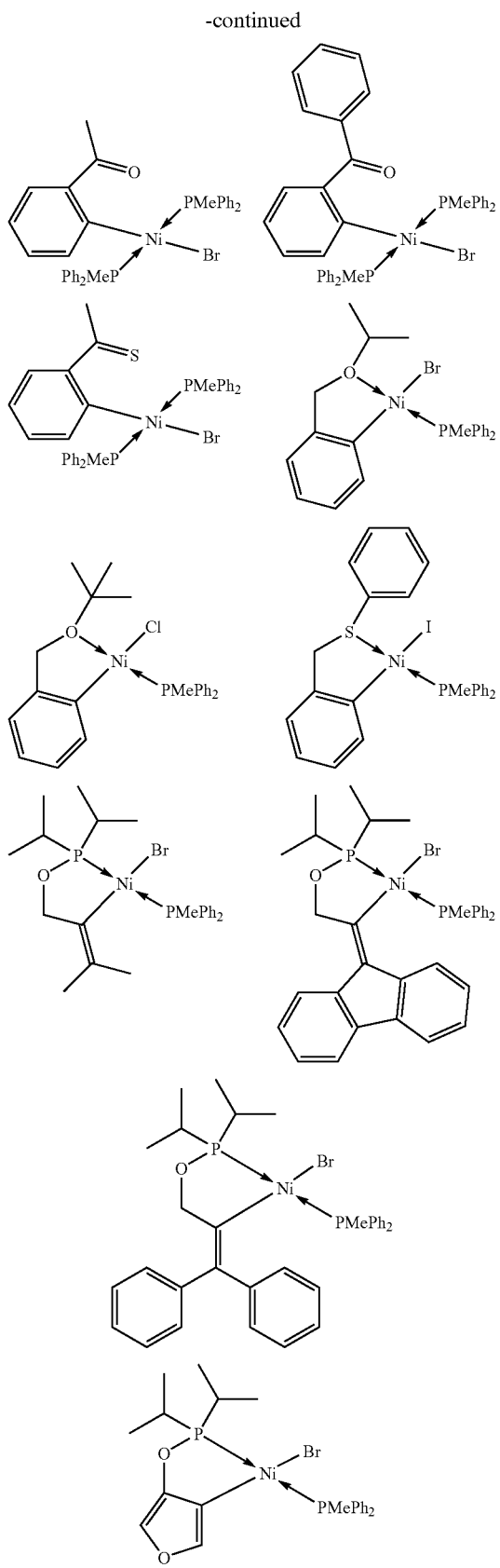

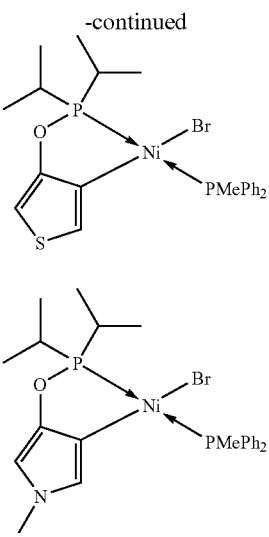

The process for preparing the transition metal compound of formula (12) is not particularly limited, but the transition metal compound of formula (12) can be prepared by the following process.

A ligand precursor represented by the following general formula (12-A):

$$\underset{R^{42}}{\overset{Z}{\diagdown}}\underset{C}{\overset{Y}{=}}\underset{R^{41}}{\overset{X''}{\diagup}} \qquad (12\text{-A})$$

wherein $R^{41}$, $R^{42}$, Y and Z are the same as $R^{41}$, $R^{42}$, Y and Z, respectively, which are defined for formula (12), and X'' represents a hydrogen atom, a substituted silyl group, a substituted stannyl group, a substituted sulfonate group or a halogen atom, is allowed to react with a raw material complex containing a transition metal M wherein M is the same as M defined for formula (12), to give the transition metal compound of formula (12). More specifically, X'' in the ligand precursor of formula (12-A) is metallized by an organometal reagent at a low temperature, and the thus-obtained compound is allowed to react with the transition metal-containing raw material complex to give a transition metal compound of formula (12-B). Alternatively, X'' in the ligand precursor of formula (12-A) is not metallized, and the ligand precursor of formula (12-A) is allowed to react with a raw material complex which is a transition metal compound having a low valence, whereby oxidative addition of C—X'' bond proceeds to give a transition metal compound of formula (12-B).

A reaction product of the ligand precursor of formula (12-A) with the raw material complex can be used without separation as a catalyst ingredient for polymerization of an olefin instead of the transition metal compound of formula (12).

In formula (13), $R^{43}$ through $R^{46}$ represent a hydrogen atom, a hydrocarbon group having 1 to 20 carbon atoms, a substituted silyl group, a substituted amide group, a substituted alkoxy group, a substituted aryloxy group, a halogen atom, or a substituent containing an atom of group 15 or group 16 of the periodic table. As specific examples of the hydrocarbon group having 1 to 20 carbon atoms, the substituted silyl group, the substituted amide group, the substituted alkoxy group, the substituted aryloxy group, and the substituent containing an atom of group 15 or group 16 of the periodic table, there can be mentioned those groups which are hereinbefore recited for R', $R^2$ and $R^3$ in formula (2). As specific examples of the halogen atom, there can be mentioned fluorine, chlorine, bromine and iodine. $R^{43}$ through $R^{46}$ may be the same or different. Y, M, X, L, a, b and c are the same as Y, M, X, L, a, b and c, respectively, which are defined for formula (1). Two members selected from Y and $R^{43}$ through $R^{46}$ may be bonded together to form a ring, provided that at least two rings can be formed. X and L may be bonded to each other, L and $R^{46}$ may be bonded to each other, and L and Y may be bonded together.

As specific examples of the transition metal compound represented by formula (13), there can be mentioned compounds represented by the following formulae.

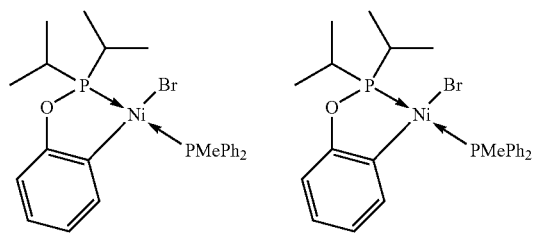

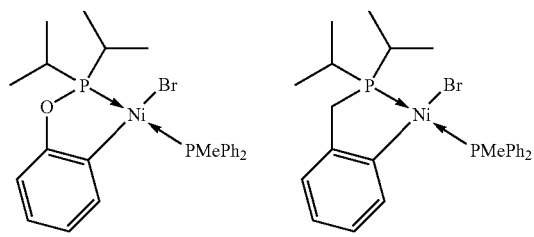

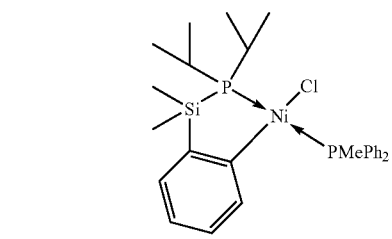

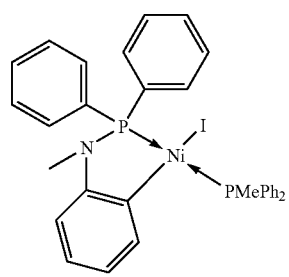

-continued

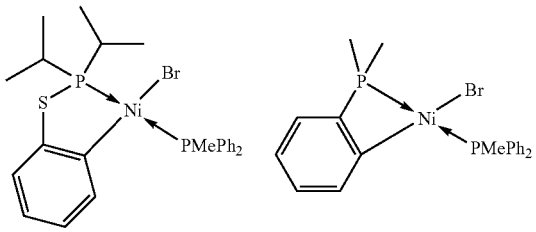

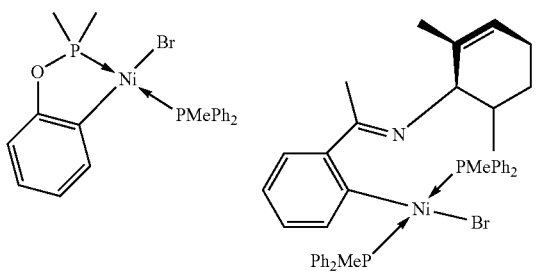

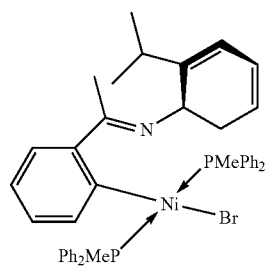

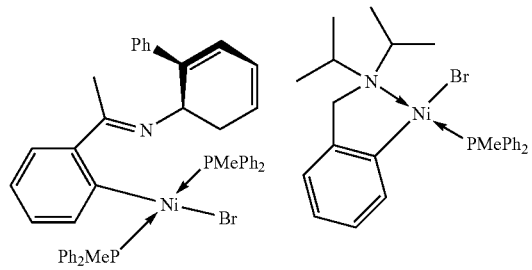

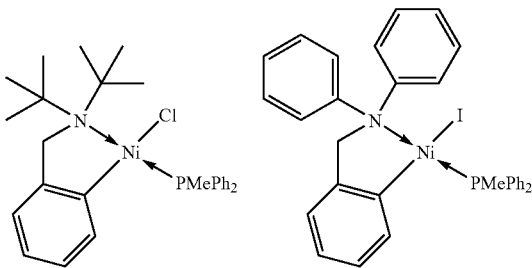

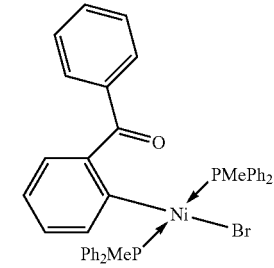

-continued

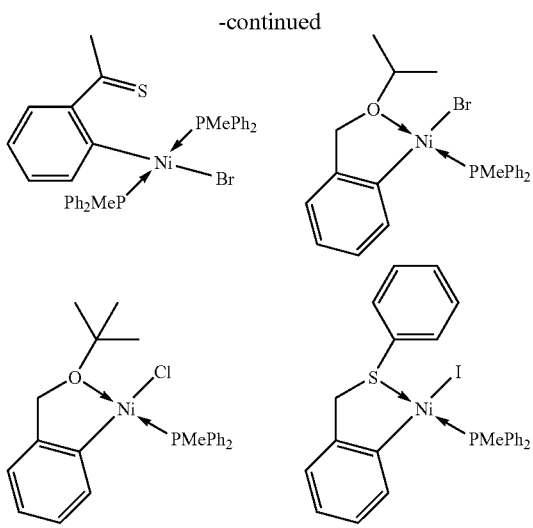

The process for preparing the transition metal compound of formula (13) is not particularly limited, but the transition metal compound of formula (13) can be prepared by the following process.

A ligand precursor represented by the following general formula (13-A):

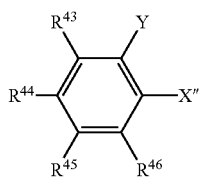

(13-A)

wherein $R^{43}$ through $R^{46}$ and Y are the same as $R^{43}$ through $R^{46}$ and Y, respectively, which are defined for formula (13), and X" represents a hydrogen atom, a substituted silyl group, a substituted stannyl group, a substituted sulfonate group or a halogen atom, is allowed to react with a raw material complex containing a transition metal M wherein M is the same as M defined for formula (13), to give the transition metal compound of formula (13). More specifically, X" in the ligand precursor of formula (13-A) is metallized by an organometal reagent at a low temperature, and the thus-obtained compound is allowed to react with the transition metal-containing raw material complex to give a transition metal compound of formula (13-B). Alternatively, X" in the ligand precursor of formula (13-A) is not metallized, and the ligand precursor of formula (13-A) is allowed to react with a raw material complex which is a transition metal compound having a low valence, whereby oxidative addition of C—X" bond proceeds to give a transition compound of formula (13-B).

A reaction product of the ligand precursor of formula (13-A) with the raw material complex can be used without separation as a catalyst ingredient for polymerization of an olefin instead of the transition metal compound of formula (13).

In formula (14), $R^{47}$ through $R^{52}$ represent a hydrogen atom, a hydrocarbon group having 1 to 20 carbon atoms, a substituted silyl group, a substituted amide group, a substituted alkoxy group, a substituted aryloxy group, a halogen atom, or a substituent containing an atom of group 15 or group 16 of the periodic table. As specific examples of the hydrocarbon group having 1 to 20 carbon atoms, the substituted silyl group, the substituted amide group, the substituted alkoxy group, the substituted aryloxy group, and the substituent containing an atom of group 15 or group 16 of the periodic table, there can be mentioned those groups which are hereinbefore recited for R', $R^2$ and $R^3$ in formula (2). As specific examples of the halogen atom, there can be mentioned fluorine, chlorine, bromine and iodine. $R^{47}$ through $R^{52}$ may be the same or different. M, X, L, a, b and c are the same as M, X, L, a, b and c, respectively, which are defined for formula (1). Two members selected from $R^{47}$ through $R^{52}$ may be bonded together to form a ring. X and L may be bonded to each other, L and $R^{47}$ may be bonded to each other, L and $R^{48}$ may be bonded to each other, and L and $R^{52}$ may be bonded to each other.

As specific examples of the transition metal compound represented by formula (14), there can be mentioned compounds represented by the following formulae.

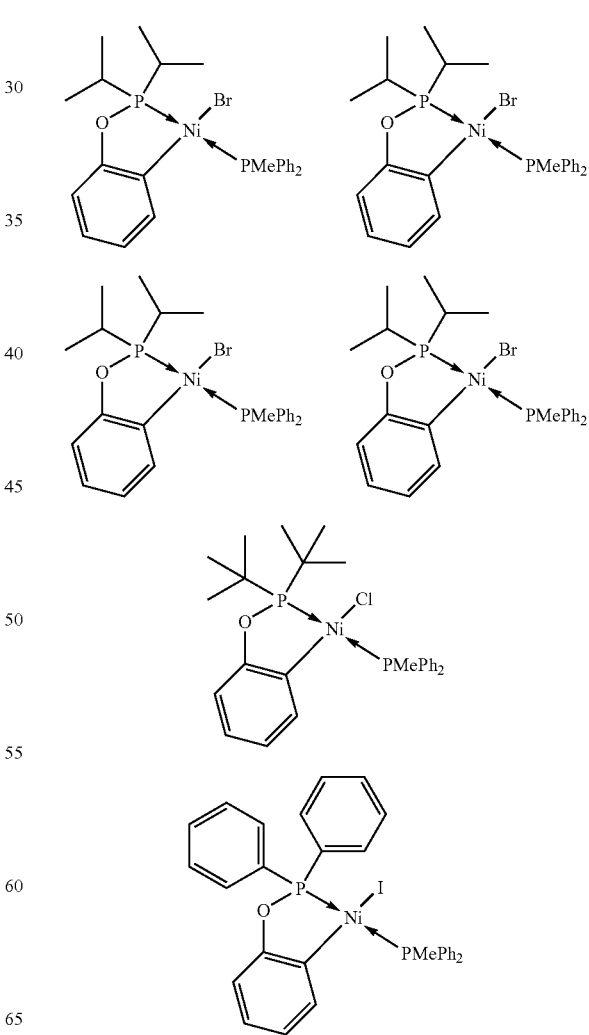

-continued

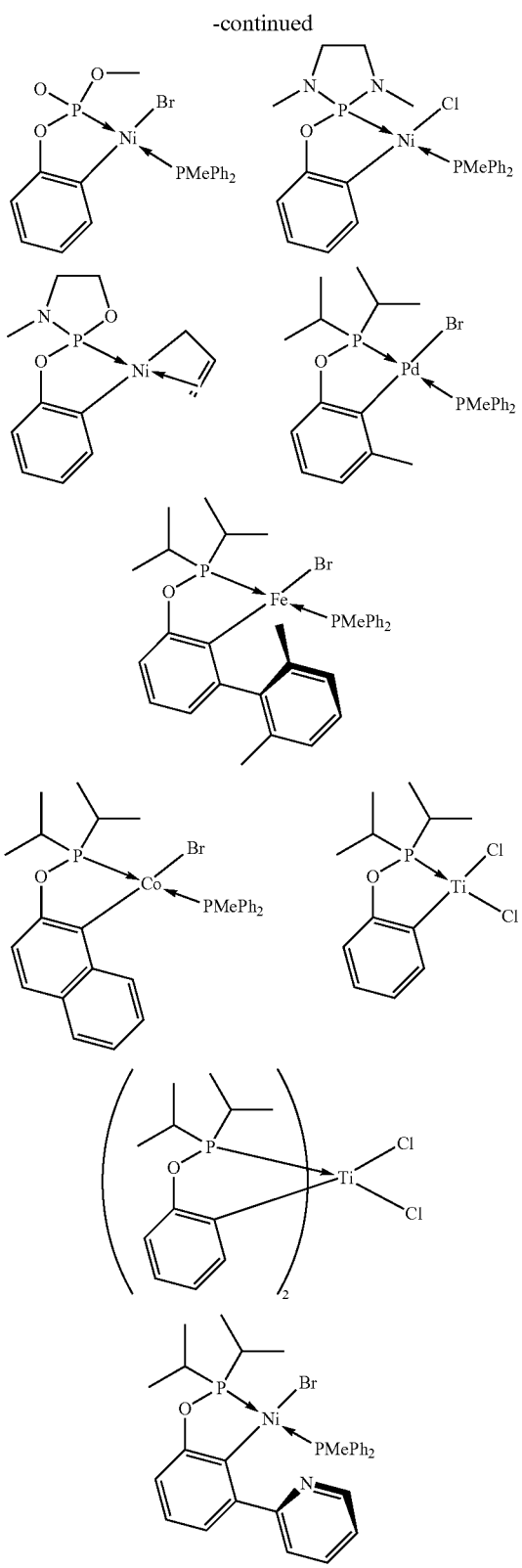

The process for preparing the transition metal compound of formula (14) is not particularly limited, but the transition metal compound of formula (14) can be prepared by the following process.

A ligand precursor represented by the following general formula (14-A):

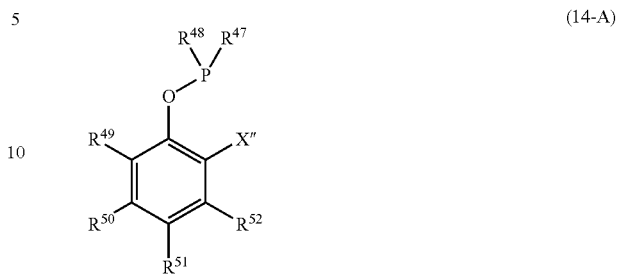

(14-A)

wherein $R^{47}$ through $R^{52}$ are the same as $R^{47}$ through $R^{52}$, respectively, which are defined for formula (14), and X" represents a hydrogen atom, a substituted silyl group, a substituted stannyl group, a substituted sulfonate group or a halogen atom, is allowed to react with a raw material complex containing a transition metal M wherein M is the same as M defined for formula (14), to give the transition metal compound of formula (14). More specifically, X" in the ligand precursor of formula (14-A) is metallized by an organometal reagent at a low temperature, and the thus-obtained compound is allowed to react with the transition metal-containing raw material complex to give a transition metal compound of formula (14-B). Alternatively, X" in the ligand precursor of formula (14-A) is not metallized, and the ligand precursor of formula (14-A) is allowed to react with a raw material complex which is a transition metal compound having a low valence, whereby oxidative addition of C—X" bond proceeds to give a transition compound of formula (14-B).

A reaction product of the ligand precursor of formula (14A) with the raw material complex can be used without separation as a catalyst ingredient for polymerization of an olefin instead of the transition metal compound of formula (14).

By the term "activating cocatalyst (B)" used in the present invention, we mean a compound having a function of forming an polymerization activation species capable of polymerizing an olefin by a cooperative action or reaction with the transition metal compound (A) containing a transition metal of groups 3 through 11 of the periodic table, which compound (A) is selected from those which are represented by formulae (1) and (4) through (14). The activating cocatalyst provides a compound which weakly coordinates or exhibits interaction for the thus-formed polymerization activation species, but does not directly react with the polymerization activation species.

The activating cocatalyst used in the present invention is classified into a first type which is used as a solution in a hydrocarbon solvent and a second type which is used as a suspension in a hydrocarbon solvent.

The first type activating cocatalyst (B) which is used as a solution in a hydrocarbon solvent includes, for example, alkylaluminoxanes which have been recently widely used as a cocatalyst for a homogeneous polymerization catalyst system for olefins, ionized ionic compounds having a non-coordinative anion, and compounds which are capable of forming a complex with L and dissociating L from M in each of formulae (1) and (4) through (14).

As preferable examples of the alkylaluminoxane as the activating cocatalyst (B), there can be mentioned compounds represented by the following formulae (15) and (16):

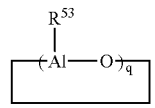 (15)

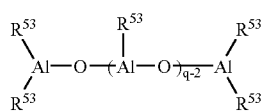 (16)

wherein $R^{53}$s may be the same or different and represent a hydrogen atom, or a hydrocarbon group having 1 to 20 carbon atoms such as methyl, ethyl, propyl and tert-butyl groups, and q is an integer in the range of 2 to 60. The alkylaluminoxanes may be used either alone or in combination. The alkylaluminoxanes may contain a minor amount of an organometallic comound.

As preferable examples of the ionized ionic compounds having a non-coordinative anion as the activating cocatalyst (B), there can be mentioned protonic acids represented by the following general formula (17), ionized ionic compounds represented by the following general formula (18), Lewis acids represented by the following general formula (19), and Lewis acidic compounds represented by the following general formula (20).

$$[H\ L^1][B(Ar)_4] \quad (17)$$

$$[A\ L^2{}_m][B(Ar)_4] \quad (18)$$

$$[D][B(Ar)_4] \quad (19)$$

$$B(Ar)_3 \quad (20)$$

wherein H is a propton, B is a boron atom or an aluminum atom, $L^1$ is a Lewis base, $L^2$ is a Lewis base or a cyclopentadienyl group, A is a cation of metal selected from lithium, sodium, iron and silver, D is a carbonium cation or a tropylium cation, Ar is a halogen-substituted aryl group having 6 to 20 carbon atoms, and m is an integer in the range of 0 to 2.

As specific examples of the protonic acids of formula (17), there can be mentioned diethyloxonium tetrakis[3,5-bis(trifluoromethyl)phenyl]borate, diethyloxonium tetrakis-(pentafluorophenyl)borate, dimethyloxonium tetrakis-(pentafluorophenyl)borate, tetramethyleneoxonium tetrakis-(pentaflourophenyl)borate, hydronium tetrakis-(pentafluorophenyl)borate, N,N-dimethylanilinium tetrakis-(pentafluorophenyl)borate, tri-N-butylammonium tetrakis-(pentafluorophenyl)borate, diethyloxonium tetrakis-(pentafluorophenyl)aluminate, dimethyloxonium tetrakis-(pentafluorophenyl)aluminate, tetramethyleneoxonium tetrakis(pentafluorophenyl)aluminate, hydronium tetrakis-(pentafluorophenyl)aluminate, N,N-dimethylanilinium tetrakis(pentafluorophenyl)aluminate and tri-N-butylammonium tetrakis(pentafluorophenyl)aluminate. The protonic acids of formula (17) are not limited to these compounds.

As specific examples of the ionized ionic compounds of formula (18), there can be mentioned sodium salts such as sodium tetrakis[3,5-bis(trifluoromethyl)phenyl]borate; lithium salts such as lithium tetrakis(pentafluorophenyl) borate and lithium tetrakis(pentafluorophenyl)aluminate, and ether complexes thereof; ferrocenium salts such as ferrocenium tetrakis(pentafluorophenyl)borate and ferrocenium tetrakis(pentafluorophenyl)aluminate; and silver salts such as silver tetrakis(pentafluorophenyl)borate and silver tetrakis(pentafluorophenyl)aluminate. The ionized ionic compounds of formula (18) are not limited to these compounds.

As specific examples of the Lewis acids of formula (19), there can be mentioned trityl tetrakis[3,5-bis-(trifluoromethyl)phenyl]borate, trityl tetrakis-(pentafluorophenyl)borate, trityl tetrakis-(pentafluorophenyl)aluminate, tropylium tetrakis-(pentafluorophenyl)borate and tropylium tetrakis-(pentafluorophenyl)aluminate. The Lewis acids of formula (19) are not limited to these compounds.

As specific examples of the Lewis acidic compounds of formula (20), there can be mentioned tris[3,5-bis(trifluoromethyl)phenyl]borate, tris(pentafluorophenyl)-borane, tris(2,3,5,6-tetrafluorophenyl)borane, tris(2,3,4,5-tetrafluorophenyl)borane, tris(3,4,5-trifluorophenyl)borane, phenyl-bis (perfluorophenyl)borane and tris(3,4,5-trifluorophenyl)aluminium. The Lewis acidic compounds of formula (20) are not limited to these compounds, As specific examples of the compounds which are capable of forming a complex with L and dissociating L from M in each of formulae (1) and (4) through (14), there can be mentioned bis(1,5-cyclooctadiene)nickel(0), bis(1,5-cyclooctadiene)-palladium(0), copper chloride(I), silver chloride(I), zinc chloride(II), titanium tetrachloride and titanium tetraisopropoxide.

The second type activating cocatalyst (B) which is used as a suspension in a hydrocarbon solvent includes, for example, clay compounds as described in, for example, Japanese Unexamined Patent Publication (hereinafter abbreviated to "JP-A") H5-301917, JP-A H7-224106, JP-A H10-139807, JP-A H10-204114, JP-A H10-231312, JP-A H10-231313, JP-A H10-182715 and JP-A H11-1509; topotactic reduction products accompanied by transfer of electrons as described in JP-A H10-56585; sulfonic acid salt compounds as described in JP-A H8-48713; alumina compounds as described in JP-A H8-157518, and solid ingredients comprised of the above-mentioned compound of formula (17), (18) or (19) chemically fixed to, for example, an inorganic oxide or an ion exchange resin as described in JP-A H8-291202. The second type activating cocatalyst (B) is not limited to these compounds.

Preferable examples of the modified clay compound as the activating cocatalyst (B) are modified clay compounds having a cation exchangeability. The modification of the clay compounds for the activating cocatalyst is preferably effected by subjecting the clay compound to treatments such as a chemical treatment with an acid, an alkali or a salt, or a treatment with an organic compound or an inorganic compound to form a composite.

As specific examples of the clay compound, there can be mentioned natural clays including kaoline group such as kaolinite, dickite and halloysite; smectite group such as montmorillonite, hectrite, beldellite, saponite, taeniolite and sauconite; mica group such as muscovite, paragonite and illite; vermiculite group; brittle mica group such as margarita and clintonite; chlorite group such as donbassite, cookeite and clinochlore; sepiolite and palygorskite; and synthetic clay compounds. The modified clay compounds are not limited to these compounds.

The treating agents used for a chemical treatment of the clay compounds include, for example, acids including brønsted acids such as hydrochloric acid, sulfuric acid, nitric acid and acetic acid; alkalis such as sodium hydroxide, potassium hydroxide and calcium hydroxide, and salts including inorganic salts which include ionic halides such as sodium chloride, potassium chloride, lithium chloride, magnesium chloride, aluminum chloride, iron chloride and ammonium chloride, sulfates such as sodium sulfate, potassium sulfate, aluminum sulfate and ammonium sulfate, carbonates such as potassium carbonate, sodium carbonate and calcium carbonate, and phosphates such as sodium phosphate, potassium phosphate, aluminum phosphate and ammonium phosphate, and organic acid salts such as sodium acetate, potassium acetate, potassium oxalate, sodium citrate and sodium tartrate.

The organic compound used for treating the clay compound to form an organic composite includes, for example, onium salts, carbon cation-forming compounds such as trityl chloride and tropylium bromide, metal complex cation-forming complex compounds such as ferrocenium salts. The inorganic compound used for treating the clay compound to form an inorganic composite includes, for example, hydroxide cation-forming metal hydroxides such as aluminum hydroxide, zirconium hydroxide and chromium hydroxide.

Among the modified clay compounds used in the present invention, an especially preferable modified clay compound is a clay compound/organic ion composite which is produced by a metal ion, i.e., an exchangeable cation, present within the clay compound is exchanged with a specific organic cation. As specific examples of the organic cation, there can be mentioned ammonium tons including aliphatic ammonium cations such as methylammonium, ethylammonium, butylammonium, hexylammonium, decylammonium, dodecylammonium, diamylammonium, tributylammonium, N,N-dimethyldodecylammonium, N,N-dimethyloctadecyl, N,N-dioctadecylmethylammonium and N,N-dioleylmethylammonium; and aromatic ammonium cations such as anilinium, N-methylanilinium, N,N-dimethylanilinium, N-ethylanilinium, N,N-diethylanilinium, benzylammonium, toluidinium, dibenzylammonium, tribenzylammonium and N,N,2,4,6-pentamethylanilinium; and oxonium ions such as dimethyloxonium and diethyloxonium. The organic cations used are not limited to these cations.

As preferable examples of the topotactic reduction product accompanied by transfer of electrons, there can be mentioned compounds represented by the following general formula (21):

wherein [J] is a host compound, k is a quantity of reduction, $E^{r+}$ is a guest cation with a valency of r, $L^3$ is a Lewis base, and h is a quantity of Lewis base.

The host compound [J] includes, for example, host compounds having a three-dimensional structure, host compounds having a two-dimensional structure, host compounds having a one-dimensional structure, and host compounds which are molecular solid.

As specific examples of the host compounds having a three-dimensional structure, there can be mentioned hexamolybdenum octasulfide, divanadium pentaoxide, tungsten trioxide, titanium dioxide, vanadium dioxide, chromium dioxide, manganese dioxide, tungsten dioxide, ruthenium dioxide, osmium dioxide and iridium dioxide.

As specific examples of the host compounds having a two-dimensional structure, there can be mentioned titanium disulfide, zirconium disulfide, hafnium disulfide, vanadium disulfide, niobium disulfide, tantalum disulfide, chromium disulfide, molybdenum disulfide, tungsten disulfide, rhenium disulfide, platinum disulfide, tin disulfide, lead disulfide, phosphomanganese trisulfide, tantalum sulfide carbide, molybdenum trioxide, vanadium pentaoxide gel, graphite and polyacene.

As specific examples of the host compounds having a one-dimensional structure, there can be mentioned titanium trisulfide and niobium triselenide.

As specific examples of the molecular solid host compounds, there can be mentioned tetracyanoquinodimethane and tetrathiofulvalene.

As the [J], a mixture of two or more of the above-mentioned host compounds can be used.

The value k is not particularly limited, but, in view of enhanced catalytic activity for polymerization of olefins, k is preferably in the range of $0<k\leq3$, and more preferably $0<k\leq2$.

The $L^3$ includes Lewis bases capable of coordinating to $E^{r+}$, and a cyclopentadienyl group. As specific examples of the Lewis bases, there can be mentioned water, amine compounds, nitrogen-containing heterocyclic compounds, ethers such as ethyl ether and n-butyl ether, amides such as formamide, N-methylformamide and N-methylacetamide, alcohols such as methyl alcohol and ethyl alcohol, and diols such as 1,2-butanediol and 1,3-butanediol. These bases may be used either alone or as a mixture of at least two thereof.

The value h can be in the range of $0\leq h\leq10$.

The guest cation $E^{r+}$ includes cations containing at least one atom selected from atoms of group 1 through group 14 of the periodic table, and r is in the range of $0<r\leq10$. In view of enhanced catalytic activity for polymerization of olefins, as preferable examples of the guest cation $E^{r+}$, there can be mentioned cations represented by the following formulae (22) and (23).

wherein $R^{54}_2R^{55}N$ is an amine compound, and $R^{54}$ independently represents a hydrogen atom or an aliphatic hydrocarbon group having 1 to 30 carbon atoms and $R^{55}$ is a hydrogen atom, an aliphatic hydrocarbon group having 1 to 30 carbon atoms or an aromatic hydrocarbon group having 6 to 50 carbon atoms.

wherein $(R^{56})^+$ is a carbonium cation or tropylium cation, which have 1 to 50 carbon atoms. These guest cations may be used either alone or in combination.

As specific examples of the amine compound represented by formula $R^{54}_2R^{55}N$, there can be mentioned aliphatic amines such as methylamine, ethylamine, n-propylamine, isopropylamine, n-butylamine, isobutylamine, tert-butylamine, allylamine, cyclopentylamine, N-methylcyclohexylamine, N,N-dimethyloctylamine, N,N-dimethylundecylamine, N,N-dimethyldodecylamine, N,N-dioctadecylmethylamine, trihexylamine, triisooctylamine, trioctylamine, tridodecylamine, N,N-dimethylcyclohexylamine and N,N-diethylcyclohexylamine; and aromatic amines such as aniline, N-methylaniline, N-ethylaniline, N-allylaniline, o-toluidine, m-toluidine, p-toluidine, N,N-dimethylaniline, N-methyl-o-toluidine, N-methyl-m-toluidine, N-methyl-p-toluidine, N-ethyl-o-toluidine and N-ethyl-m-toluidine.

As specific examples of the cation of formula (23), there can be mentioned a triphenylmethyl cation and a tropylium cation.

The catalyst of the present invention comprising the above-mentioned transition metal compound (A) and the above-mentioned activating cocatalyst (B) can be used in combination with an organometallic compound (C). As specific examples of the organometallic compound (C), there can be mentioned alkyllithium compounds such as methyllithium and n-butyllithium; Grignard reagents such as methylmagnesium chloride, ethylmagnesium chloride, isopropylmagnesium chloride, benzylmagnesium chloride, methylmagnesium bromide, ethylmagnesium bromide, isopropylmagnesium bromide and benzylmagnesium bromide; dialkylmagnesiums such as dimethylmagnesium, dialkylzincs such as dimethylzinc and diethylzinc; alkylboranes such as trimethylborane and triethylborane; alkylaluminums such as trimethylaluminum, triethylaluminum and truisobutylaluminum; and alkylaluminoxanes such as methylaluminoxane and ethylaluminoxane. Preferable examples of the organo metallic compounds are alkyllithiums, Grignard reagents, alkylaluminoxanes, and organoaluminum compounds represented by the following formula (24).

  (24)

wherein $R^{57}$s may be the same or different, and represent a hydrogen atom, an amide group, an alkoxy group or a hydrocarbon group, and at least one of $R^{57}$s is a hydrocarbon group. Trialkylaluminum, such as triethylaluminum and truisobutylaluminum are especially preferable.

The proportion of transition metal compound (A), activating cocatalyst (B) and organometallic compound (C) is not particularly limited, but preferably the following conditions are satisfied. When activating cocatalyst (B) is aluminoxane of formula (15) and/or (16), the ratio (A)/(B) is in the range of 100/1 to 1/1,000,000 by mole, more preferably 1/1 to 1/10,000 by mole based on the metal atom, and (A)/(C) is in the range of 100/1 to 1/100,000 by mole, more preferably 1/1 to 1/10,000 by mole based on the metal atom. When activating cocatalyst (B) is protonic acid of formula (17), ionized ionic compound of formula (18), Lewis acid (19) or Lewis acidic compound (20), the ratio (A)/(B) is in the range of 10/1 to 1/1,000 by mole, more preferably 3/1 to 1/100 by mole based on the metal atom, and (A)/(C) is in the range of 100/1 to 1/100,000 by mole, more preferably 1/1 to 1/10,000 by mole based on the metal atom. When activating cocatalyst (B) is a modified clay compound, the ratio (A)/(B) is in the range of 10/1 to 1/10,000 by weight, more preferably 3/1 to 1/10,000 by weight, and(A)/(C) is in the range of 100/1 to 1/100,000 by mole, more preferably 1/1 to 1/10,000 by mole based on the metal atom.

The method for preparing the catalyst for polymerization of an olefin comprising transition metal compound (A), activating cocatalyst (B) and organometallic compound (C) is not particularly limited, and includes, for example, a method wherein the three ingredients are placed in contact to be thereby reacted with each other in a liquid medium inactive to the three ingredients or in a monomer used for polymerization. The order in which the three ingredients are reacted with each other is not particularly limited. The conditions such as temperature and time for treating these ingredients are also not particularly limited. Each of the three ingredients (A), (B) and (C) may be used either alone or as a combination of at least two kinds of species.

In the present invention, a catalyst for polymerization of an olefin comprising transition metal compound (A) and activating cocatalyst (B) can be used in a form of being supported on finely divided solid particles. The solid particles used as carrier include inorganic solid particles and organic particles. As specific examples of the carrier, there can be mentioned inorganic particles of $SiO_2$, $Al_2O_3$, ZrO, $B_2O_3$, CaO, ZnO, $MgCl_2$ and $CaCl_2$, and combination of at least two thereof; and organic particles of polyolefins such as polyethylene, polypropylene, poly-1-butene and polystyrene, mixtures of these polyolefins with a polar polymer such as polyethyl methacryalte, polyester or polyimide, and copolymers of an olefin for these polyolefins with a monomer giving the polar polymer. The shape of the finely divided solid particles is not particularly limited, but, the solid particles preferably have an average particle diameter in the range of 5 to 200 μm and micro-pores with an average diameter in the range of 20 to 100 angstrom.

The polymerization of an olefin using the catalyst of the present invention can be carried out by ordinary polymerization procedures such as slurry polymerization, vapor phase polymerization, high-pressure polymerization, solution polymerization and bulk polymerization. By the term "polymerization" used herein, we mean not only homopolymerization for producing a homopolymer but also copolymerization for producing a copolymer.

The polymerization of an olefin can be carried out in the vapor phase or the liquid phase. When the polymerization is carried out in the vapor phase, substantially uniform polymer particles can be efficiently and stably produced. When the polymerization is carried out in the liquid phase, a liquid medium used is not particularly limited and may be selected from organic mediums which are generally used. The organic medium includes, for example, benzene,toluene, xylene, pentane, hexane and heptane. Olefins themselves such as propylene, 1-butene, 1 octene and 1-hexene may be used as the liquid medium.

As specific examples of the olefin to be polymerized in the presence of the catalyst of the present invention, there can be mentioned α-olefins such as ethylene, propylene, 1-butene, 4-methyl-1-pentene, 1-hexene and 1-otene; styrene; conjugated dienes and non-conjugated dienes such as butadiene, 1,4-hexadiene, 5-ethylidene-2-norbornene, cyclopentadiene, 4-methyl-1,4-hexadiene and 7-methyl-1,6-octadiene; cycloolefins such as cyclobutene; α, β-unsaturated carboxylic acids such as acrylic acid, methacrylic acid, fumaric acid, maleic anhydride, itaconic acid, itaconic anhydride and bicyclo(2,2,1)-5-heptene-2,3-dicarboxylic acid; metal salts of α, β-unsaturated carboxylic acids such as sodium, potassium, lithium, zinc, magnesium and calcium salts of the above-recited α, β-unsaturated carboxylic acids; esters of α, β-unsaturated carboxylic acids such as methyl acrylate, ethyl acrylate, isopropyl acrylate, n-butyl acrylate, isobutyl acrylate, tert-butyl acrylate, 2-ethylhexyl acrylate, methyl methacrylate, ethyl methacrylate, n-propyl methacrylate, isopropyl methacrylate, n-butyl methacrylate and isobutyl methacrylate; vinyl esters such as vinyl acetate, vinyl propionate, vinyl caproate, vinyl caprylate, vinyl laurate, vinyl stearate and vinyl trifluoroacetate; and unsaturated glycidyl esters such as glycidyl acrylate, glycidyl methacrylate, glycidyl itaconate and monoglycidyl itaconate. These olefins may be copolymerized by using at least two thereof, such as ethylene plus propylene, ethylene plus 1-butene, ethylene plus 1-hexene, ethylene plus 1-octene, ethylene plus vinyl acetate, ethylene plus methyl methacrylate, ethylene plus propylene plus styrene, ethylene plus 1-hexene plus styrene, and ethylene plus propylene plus ethylidene norbornene.

The polymerization conditions employed for polymerization of olefins are not particularly limited, but preferably, the polymerization temperature is in the range of –100° C. to 300° C., the polymerization time is in the range of 10 seconds to 48 hours, and the polymerization pressure is in the range of normal pressure to 300 MPa. At polymerization, the molecular weight can be controlled by using hydrogen. The polymerization procedure can be any of batchwise, semi-continuous and continuous manners. The polymerization can be carried out in two or more stages under different polymerization conditions. Olefin polymers are separated for recovery from a polymerization mixture and dried by a conventional procedure.

The invention will now be described by the following working examples that by no means limit the scope of the invention.

In the working examples, all of the reactions were carried out in an inert gas atmosphere. Liquid mediums used in the reactions were purified, dried or deoxygenated prior to the use by the conventional procedure.

Polymerization was carried out by using 100 ml pressure-resistant glass or stainless steel vessel with stirring by a stirrer tip, or 2 liter stainless steel vessel with stirring by a mechanical stirrer.

Melting point (Tm) of a polymer was measured by a differential scanning calorimeter (DSC). Number average molecular weight (Mn), weight average molecular weight (Mw) and molecular weight distribution (Mw/Mn) were determined by measurement by gel permeation chromatography (GPC) using 1,2,4-trichlorobenzene at a column temperature of 140° C.

EXAMPLE 1

Polymerization of Ethylene Using Complex 3a-Fe

[Synthesis of Complex 1a]

In an argon atmosphere, a Schlenk flask was charged with [bis(1.5-cyclooctadiene)nickel(0)](1.00g, 3.64 mmol), and dry diethyl ether (20 ml) was added in which the content of the flask was suspended. A solution of 2,6-dimethylphenylisocyanide (2.00 g, 15.24 mmol) in diethyl ether (30 ml) was dropwise added over a period of 5 minutes. The reaction liquid was changed to a red uniform solution and thereafter changed to a yellow suspension. After reaction was carried out for 1 hour, a supernatant was removed, and a precipitate was dissolved in benzene. The thus-obtained solution was filtered, and the filtrate was evaporated to dryness under vacuum to give a yellow powder (complex 1a)(yield: 1.76 g, 82%).

$^1$H-NMR ($\delta$, $C_6D_6$): 6.78(t, 1H), 6.72(d, 2H), 2.35(s, 6H)

[Synthesis of Complex 2a]

In an argon atmosphere, a Schlenk flask was charged with tetrakis(2,6-dimethylphenylisocyanide)nickel(0)(complex 1a)(1.42 g, 2.43 mmol), and dry benzene (30 ml) was added to dissolve complex 1a therein. MeI (1 ml, 16.06 mmol) was added, and reaction was carried out under reflux for 24 hours. After completion of the reaction, the reaction mixture was cooled to room temperature, and Filtered. The filtrate was evaporated to dryness under vacuum. The obtained solid was washed with hexane to give a reddish brown powder (complex 2a) (yields 1.57 g, 89%).

$^1$H-NMR ($\delta$, $C_6D_6$): 6.97–6.64(m, 6H), 6.62–6.60(m, 3H), 6.50–6.44(m, 3H), 2.32(s, 6H), 2.29(s, 6H), 2.09(s, 6H), 1.95(s, 6H), 1.81(s, 3H)

[Synthesis of Complex 3a-Fe]

In an argon atmosphere, a Schlenk flask was charged with iodo[1,2,3-tris(2,6-dimethylphenylimino)butyl](2,6-dimethylphenylisocyanide)nickel(II) (0.22 g, 0.33 mmol), and iron (II) dibromide (0.066 g, 0.31 mmol). Dry benzene (20 ml) and tetrahydrofuran (5 ml) were added. Reaction was carried out for 12 hours. After completion of the reaction, the solvent was removed ubder vacuum. The residue was recrystallized from hot toluene to give a black crystal (complex 3a-Fe) (yield: 0.18 g, 58%).

X-ray structure analysis of complex 3a-Fe [Iodo[1,2,3-tris(2,6-dimethylphenylimino)butyl](2,6-dimethylphenylisocyanide)nickel(II)]dibromoiron(II)] was carried out, and an ORTEP diagram thereof is shown in FIG. 1.

[Preparation of Catalyst]

In an argon atmosphere, a Schlenk flask was charged with iodo[1,2,3-tris(2,6-dimethylphenylimino)butyl](2,6-dimethylphenylisocyanide)nickel(II)dibromoiron(II) (complex 3a-Fe) (9.44 mg, 10 µmol). Dry toluene (49.4 ml) was added to prepare a suspension of complex 3a-Fe. A solution of methylaluminoxane in toluene ("PMAO-S" available from TOSOH-FINECHEM Corp.; conc. 3.13 mol/liter) (0.63 ml, 2.0 mmol) was added, and the mixture was stirred for 30 minutes to give a catalyst solution having a concentration of 0.2 mmol/liter.

[Polymerization of Ethylene]

In an argon atmosphere, a 100 ml pressure-resistant stainless steel vessel was charged with dry toluene (45 ml) and then the above-mentioned catalyst (5 ml, 1 µmol) was added. The content was stirred at room temperature. Then ethylene was blown into the pressure-resistant vessel in an amount such that the partial pressure of ethylene reached 0.8 MPa, to initiate polymerization. Polymerization was carried out for 20 minutes. Unreacted ethylene was removed, and methanol (5 ml) was added to stop the polymerization. The polymerization liquid was poured in hydrochloric acid-added methanol (300 ml) to precipitate a polymer. The polymer-containing liquid was filtered and the solid was dried to give polyethylene (yield: 540 mg; activity: 540 g/mmol) (Tm: 131.1° C., Mw: 190,000, Mw/Mn: 3.4).

EXAMPLE 2

Polymerization of Ethylene Using Complex 3a-Co

[Synthesis of Complex 3a-Co]

The procedure for the preparation of complex 3a-Fe in Example 1 was repeated wherein cobalt(II) dibromide was used instead of iron(II) bromide. Thus a black crystal (complex 3a-Co) was obtained (yield: 0.25 g, 81%).

Figure 2:
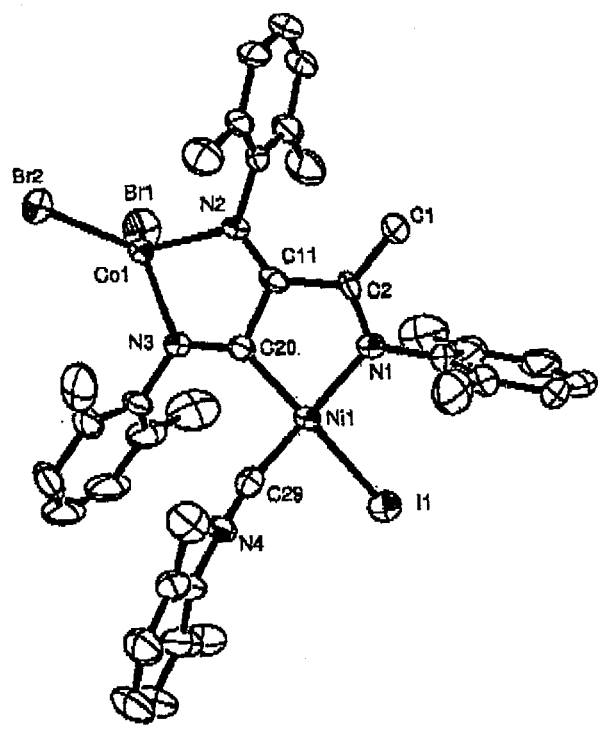
FIG. 2 is an ORTEP diagram of complex 3a-Co [Iodo[1,2,3-tris(2,6-dimethylphenylimino)butyl](2,6-dimethylphenylisocyanide)nickel(II)]dibromocobalt(II).

X-ray structure analysis of complex 3a-Co [Iodo[1,2,3-tris(2,6-dimethylphenylimino)butyl](2,6-dimethylphenylisocyanide)nickel(II)]dibromocobalt(II)] was carried out, and an ORTEP diagram thereof is shown in FIG. 2.

[Preparation of Catalyst]

A catalyst was prepared by the same procedure as that employed in Example 1 except that complex 3a-Co was used instead of complex 3a-Fe. Thus a catalyst solution having a concentration of 0.2 mmol/liter was obtained.

[Polymerization of Ethylene]

Ethylene was polymerized by the same procedure as that employed in Example 1 except that the catalyst solution containing complex 3a-Co was used instead of the catalyst solution containing complex 3a-Fe. Thus polyethylene was obtained in a yield of 234 mg (activity: 234 g/mmol) (Tm: 130.2° C., Mw: 280,000, Mw/Mn: 2.9).

COMPARATIVE EXAMPLE 1

Polymerization of Ethylene Using Dibromo[2,3-bis(2,6-dimethylphenylimino)butane]iron(II) (Complex A-Fe)

[Preparation of Catalyst]

A catalyst was prepared by the same procedure as that employed in Example 1 except that complex A-Fe was used instead of complex 3a-Fe, the amount of catalyst was changed from 10 µmol to 100 µmol, and the ratio of PMAO/complex was changed from 200 by mol to 100 by mol. Thus a catalyst solution having a concentration of 2.0 mmol/liter was obtained.

[Polymerization of Ethylene]

Ethylene was polymerized by the same procedure as that employed in Example 1 except that the catalyst solution containing complex A-Fe at a concentration of 2.0 mmol/liter was used instead of the catalyst solution containing complex 3a-Fe at a concentration of 0.2 mmol/liter, and the polymerization time was changed to 60 minutes. Thus polyethylene was obtained in a yield of 254 mg (activity: 2.54 g/mmol) (Tm: 131.1° C., Mw: 300,000, Mw/Mn: 2.3).

COMPARATIVE EXAMPLE 2

Polymerization of Ethylene Using Dibromo[2,3-bis(2,6-dimethylphenylimino)butane]cobalt(II) (Complex A-Co)

[Preparation of Catalyst]

A catalyst was prepared by the same procedure as that employed in Comparative Example 1 except that complex A-Co was used instead of complex A-Fe. Thus a catalyst solution having a concentration of 2.0 mmol/liter was obtained.

[Polymerization of Ethylene]

Ethylene was polymerized by the same procedure as that employed in Comparative Example 1 except that the catalyst solution containing complex A-Co was used instead of the catalyst solution containing complex A-Fe, and the polymerization time was changed to 40 minutes. Thus polyethylene was obtained in a yield of 135 mg (activity: 1.35 g/mmol) (Tm: 130.2° C., Mw: 360,000, Mw/Mn: 2.3).

EXAMPLE 3

Polymerization of Ethylene Using Complex 3b-Fe

[Synthesis of Complex 1b]

The procedure for the preparation of complex 1a in Example 1 was repeated wherein 2,6-diethylphenylisocyanide was used instead of 2,6-dimethylphenylisocyanide. Thus a yellow powder (complex 1b) was obtained in a yield of 1.87 g (71%).

$^1$H-NMR ($\delta$, $C_6D_6$): 6.92(t, 1H, J=7.80 Hz), 6.82(d, 2H, J=7.80 Hz), 2.84(q, 4H, J=7.59 Hz), 1.25(t, 6H, J=7.59 Hz)

[Synthesis of Complex 2b]

The procedure for the preparation of complex 2a in Example 1 was repeated wherein complex 1b was used instead complex 1a. Thus a reddish brown powder (complex 2b) was obtained in a yield of 1.57 g (89%).

$^1$H-NMR ($\delta$, $C_6D_6$): 7.13–7.08(m, 3H), 7.05–6.96(m, 3H), 6.79–6.57(m, 6H), 3.07(q, 1H, J=7.56 Hz), 3.04(q, 1H, J=7.56 Hz), 2.91(g, 1H, J=7.56 Hz), 2.87(t, 1H, J=7.56Hz), 2.73–2.47(m, 8H), 2.30(q, 4H, J=7.56 Hz), 1.89(s, 3H), 1.32(t, 6H, J=7.32 Hz), 1.31(t, 6H, J=7.56 Hz), 1.05(t, 6H, J=7.56Hz), 0.99(t, 6H, J=7.56 Hz)

[Synthesis of Complex 3b-Fe]

The procedure for the preparation of complex 3a-Fe in Example 1 was repeated wherein complex 2b was used instead of complex 2a. Thus a black crystal (complex 3b-Fe) was obtained in a yield of 0.12 g (67%).

[Preparation of Catalyst]

A catalyst was prepared by the same procedure as that employed in Example 1 except that complex 3b-Fe was used instead of complex 3a-Fe. Thus a catalyst solution having a concentration of 0.2 mmol/liter was obtained.

[Polymerization of Ethylene]

Ethylene was polymerized by the same procedure as that employed in Example 1 except that 50 ml of the catalyst solution containing complex 3b-Fe at a concentration of 0.2 mmol/liter was used instead of 5 ml (1 µmol) of the catalyst solution containing complex 3a-Fe at a concentration of 0.2 mmol/liter and 45 ml of toluene. Polyethylene was obtained in a yield of 284 mg (activity: 28.4 g/mmol) (Tm: 115.9° C., Mw: 690,000, Mw/Mn: 2.5).

EXAMPLE 4

Polymerization of Ethylene Using Complex 3c-Fe

[Synthesis of Complex 1c]

The procedure for the preparation of complex 1a in Example 1 was repeated wherein 2,6-diisopropylphenylisocyanide was used instead of 2,6-dimethylphenylisocyanide. Thus a yellow powder (complex 1c) was obtained in a yield of 1.44 g (62%).

$^1$H-NMR ($\delta$, $C_6D_6$): 7.02(t, 1H, J=6.39 Hz), 6.94(d, 2H, J=6.39 Hz), 3.70(sep, 2H, J=7.19 Hz), 1.26(d, 12H, J=7.19 Hz)

[Synthesis of Complex 2c]

The procedure for the preparation of complex 2a in Example 1 was repeated wherein complex 1c was used instead of complex 1a. Thus a reddish brown powder (complex 2c) was obtained in a yield of 0.47 g (66%).

$^1$H-NMR ($\delta$, $C_6D_6$): 7.06–6.95(m, 8H), 6.92–6.76(m, 4H), 3.68(br, 2H), 3.49(7th, 2H, J=6.77 Hz), 3.10(7th, 2H, J=6.77 Hz), 2.64(7th, 2H, J=6.77 Hz), 2.00(s, 3H), 1.68(d, 6H, J=6.77 Hz), 1.34(d, 6H, J=6.77Hz), 1.25(d, 6H, J=6.77 Hz), 1.20(d, 6H, J=6.77 Hz), 1.18(d, 18H, J=6.77 Hz), 1.03(d, 6H, J=6.52 Hz)

[Synthesis of Complex 3c-Fe]

The procedure for synthesis of complex 3a-Fe in Example 1 was repeated wherein complex 2c was used instead complex 2a. Thus a black crystal (complex 3c-Fe) was obtained in a yield of 0.14 g (64%).

[Preparation of Catalyst]

A catalyst was prepared by the same procedure as that employed in Example 1 except that complex 3c-Fe was used instead of complex 3a-Fe. Thus a catalyst solution having a concentration of 0.2 mmol/liter was obtained.

[Polymerization of Ethylene]

Ethylene was polymerized by the same procedure as that employed in Example 3 except that the catalyst solution containing complex 3c-Fe was used instead of the catalyst solution containing complex 3b-Fe. Polyethylene was obtained in a yield of 66 mg (activity; 6.6 g/mmol) (Tm: 90.5° C., Mw: 550,000, Mw/Mn: 5.0).

EXAMPLE 5

Polymerization of Ethylene Using Complex 3d-Fe

[Preparation of Catalyst]

In an argon atmosphere, a Schlenk flask was charged with bis(1,5-cyclooctadiene)nickel(0) (0.567 g, 2.06 mmol), and then dry diethyl ether (20 ml) was added to prepare a suspension of bis(1,5-cyclooctadiene)nickel(0). A solution of 2-isopropylphenylisocyanide (1.20 g, 8.26 mmol) in diethyl ether (10 ml) was dropwise added over a period of 5 minutes. The reaction liquid was changed to a red uniform solution and thereafter changed to a yellow suspension. After reaction was carried out for 1 hour, a supernatant was removed, and a precipitate was dissolved in benzene. The thus-obtained solution was filtered, and the filtrate was evaporated to dryness under vacuum. The solid reaction product was dissolved in dry benzene (30 ml), and MeI (0.64 ml, 10.30 mmol) was added. The mixture was allowed to react under reflux for 24 hours. After completion of the reaction, the reaction liquid was cooled to room temperature and filtered. The filtrate was evaporated to dryness under vacuum to give a black solid in a yield of 1.43 g.

In an argon atmosphere, a Schlenk flask was charged with the above black solid (0.36 g) and iron(II) dibromide (0.10 g, 0.46 mmol), and then dry benzene (20 ml) and tetrahydrofuran (5 ml) were added. Reaction was carried out for 12 hours. After completion of the reaction, the solvent was removed by distillation. The residue was recrystallized from hot toluene to give a black crystal in a yield of 0.42 g.

A catalyst was prepared by the same procedure as that employed in Example 1 except that the above black crystal was used instead of complex 3a-Fe. Thus a catalyst solution having a concentration of 0.2 mmol/liter was obtained.

[Polymerization of Ethylene]

Ethylene was polymerized by the same procedure as that employed in Example 1 except that the above catalyst solution was used instead of the catalyst solution containing complex 3a-Fe. Polyethylene was obtained in a yield of 343 mg (activity: 343 g/mmol) (Tm: 125.8° C., Mw: 41,000, Mw/Mn: 14).

EXAMPLE 6

Polymerization of Ethylene Using Complex 3e-Fe

[Preparation of Catalyst]

In an argon atmosphere, a Schlenk flask was charged with bis(1,5-cyclooctadiene)nickel(0) (0.617 g, 2.24 mmol), and then dry diethyl ether (20 ml) was added to prepare a suspension of bis(1,5-cyclooctadiene)nickel(0). A solution of 2-methyl-6-isopropylphenylisocyanide (1.43 g, 8.96 mmol) in diethyl ether (10 ml) was dropwise added over a period of 5 minutes. The reaction liquid was changed to a red uniform solution and thereafter changed to a yellow suspension. After reaction was carried out for 1 hour, a supernatant was removed, and a precipitate was dissolved in benzene. The thus-obtained solution was filtered, and the filtrate war evaporated to dryness under vacuum. The solid reaction product was dissolved in dry benzene (30 ml), and MeI (0.64 ml, 10.30 mmol) was added. The mixture was allowed to react under reflux for 24 hours. After completion of the reaction, the reaction liquid was cooled to room temperature and filtered. The filtrate was evaporated to dryness under vacuum to give a black solid in a yield of 1.93 g.

In an argon atmosphere, a Schlenk flask was charged with the above black solid (0.79 g) and iron(II) dibromide (0.20 g, 0.95 mmol), and then dry dichloromethane (15 ml) and ethanol (10 ml) were added. Reaction was carried out for 12 hours. After completion of the reaction, the solvent was removed under vacuum. The residue was recrystallized from hot toluene to give a black crystal in a yield of 0.42 g.

A catalyst was prepared by the same procedure as that employed in Example 1 except that the above black crystal (complex 3e-Fe) was used instead of complex 3a-Fe. Thus a catalyst solution having a concentration of 0.2 mmol/liter was obtained.

[Polymerization of Ethylene]

Ethylene was polymerized by the same procedure as that employed in Example 3 except that the above catalyst solution containing complex 3e-Fe was used instead of the catalyst solution containing complex 3b-Fe. Polyethylene was obtained in a yield of 991 mg (activity: 99.6 g/mmol) (Tm: 115.9° C., Mw: 1,140,000, Mw/Mn: 6.3).

EXAMPLE 7

Polymerization of Ethylene Using Reaction Product of Complex 2a with Dibromo(1,2-dimethoxyethane)nickel(II)

[Preparation of Catalyst]

In an argon atmosphere, a Schlenk flask was charged with complex 2a (7.25 mg, 10 μmol) and dibromo(1,2-dimethoxyethane)nickel(II) (3.09 g, 10 μmol). Dry benzene (20 ml) and tetrahydrofuran (5 ml) were added. Reaction was carried out for 12 hours. After completion of the reaction, the solvent was removed by distillation. Thus a black powder was obtained. The powdery reaction product was dissolved in dry toluene (49.4 ml), and a solution of methylaluminoxone in toluene ("PMAO-S" available from TOSOH-FINECHEM Corp.; conc. 3.13 mol/liter) (0.63 ml, 2.0 mmol) was added. The mixture was stirred for 30 minutes to give a catalyst solution.

[Polymerization of Ethylene]

Ethylene was polymerized by the same procedure as that employed in Example 1 except that the catalyst containing the reaction product of complex 2a with dibromo(1,2-dimethoxyethane)nickel(II) was used instead of the catalyst containing complex 3a-Fe. Polyethylene was obtained in, a yield of 709 mg (activity: 709 g/mmol) (Tm: 132.0° C., MW 240,000, Mw/Mn: 3.6).

EXAMPLE 8

Polymerization of Ethylene Using Reaction Product of Complex 2a with Dichloro (1.5-cyclooctadiene)platinum(II)

[Preparation of Catalyst]

A catalyst solution having a concentration of 0.2 mmol/liter was prepared by the same procedure as employed in Example 7 except that dichloro(1,5-cyclooctadiene)platinum(II) was used instead of dibromo(1,2-dimethoxyethane) nickel(II).

[Polymerization of Ethylene]

Ethylene was polymerized by the same procedure as that employed in Example 1 except that the catalyst containing the reaction product of complex 2a with dichloro(1,5-cyclooctadiene)platinum(II) was used instead of the catalyst containing complex 3a-Fe. Polyethylene was obtained in a yield of 559 mg (activity: 559 g/mmol) (Tm: 131.6° C., MW: 330,000, Mw/Mn: 2.4).

EXAMPLE 9

Polymerization of Ethylene Using Reaction Product of Complex 2a with Chloromethyl(1,5-cyclooctadiene)palladium(II)

[Preparation of Catalyst]

A catalyst solution having a concentration of 0.2 mmol/liter was prepared by the same procedure as employed in Example 7 except that chloromethyl(1,5-cyclooctadiene)-palladium(II) was used instead of dibromo(2-dimethoxyethane)nickel(II).

[Polymerization of Ethylene]

Ethylene was polymerized by the same procedure as that employed in Example 1 except that the catalyst containing the reaction product of complex 2a with chloromethyl(1,5-cyclooctadiene)palladium(II) was used instead of the catalyst containing complex 3a-Fe. Polyethylene was obtained in a yield of 935 mg (activity: 935 mmol) (Tm: 129.4° C., Mw: 260,000, Mw/Mn: 2,3).

The results of polymerization in Examples 1 to 9 and Comparative Examples 1 and 2 are shown in Table 1. and chemical structures of the compounds used in these working examples are shown in Table 2.

TABLE 1

| Example No. | Ex. 1 | Ex. 2 | Ex. 3 | Ex. 4 | Ex. 5 | Ex. 6 | Ex. 7 | Ex. 8 | Ex. 9 | C. Ex. 1 | C. Ex. 2 |
|---|---|---|---|---|---|---|---|---|---|---|---|
| Tran. metal cpd*1 | 3a-Fe | 3a-Co | 3b-Fe | 3c-Fe | 3d-Fe | 3e-Fe | 2a | 2a | 2a | 4-Fe | 4-Co |
| Amount (μmol) | 1 | 1 | 10 | 10 | 1 | 10 | 1 | 1 | 1 | 100 | 100 |
| Addive metal | — | — | — | — | — | — | Ni*3 | Pt*4 | Pd*5 | — | — |
| Amount (μmol) | — | — | — | — | — | — | 1 | 1 | 1 | — | — |
| Acti. cocata.*2 | PMAO | PMAO | PMAO | PMAO | PMAO | PMAO | PMAO | PMAO | PMAO | PMAO | PMAO |
| Amount (μmol) | 200 | 200 | 2000 | 2000 | 200 | 2 | 200 | 200 | 200 | 10000 | 10000 |
| Ethylene pressure (MPa) | 0.8 | 0.8 | 0.8 | 0.8 | 0.8 | 0.8 | 0.8 | 0.8 | 0.8 | 0.8 | 0.8 |
| Polymn. time (min) | 20 | 20 | 20 | 20 | 20 | 20 | 20 | 20 | 20 | 60 | 40 |
| Polymn. temp.*6 | r.t. | r.t. | r.t. | r.t. | r.t. | r.t. | r.t. | r.t. | r.t | r.t | r.t |
| Polymer yield (g) | 0.540 | 0.234 | 0.284 | 0.066 | 0.343 | 0.991 | 0.709 | 0.559 | 0.935 | 0.254 | 0.135 |
| Activity (g/mmol) | 540 | 234 | 28.4 | 6.6 | 343 | 99.6 | 709 | 559 | 935 | 2.54 | 1.35 |
| Melting point (° C.) | 131.1 | 130.2 | 115.9 | 90.5 | 125.8 | 115.9 | 132.0 | 131.6 | 129.4 | 131.1 | 130.2 |
| $Mn \times 10^3$ | 56 | 97 | 280 | 110 | 3 | 180 | 66 | 140 | 110 | 130 | 160 |
| $Mw \times 10^3$ | 190 | 280 | 690 | 550 | 41 | 1140 | 240 | 330 | 260 | 300 | 360 |
| Mw/Mn | 3.4 | 2.9 | 2.5 | 5.0 | 14 | 6.3 | 3.6 | 2.4 | 2.3 | 2.3 | 2.3 |

Note,
*1 Transition metal compound
*2 Activating cocatalyst
*3 $NiBr_2$ (dme)
*4 $PtCl_2$ (cod)
*5 PdClMe (cod)
*6 Polymerization temperature: r.t. = room temperature

TABLE 2

| Example | compound |
|---|---|
| 1 | 3a-Fe 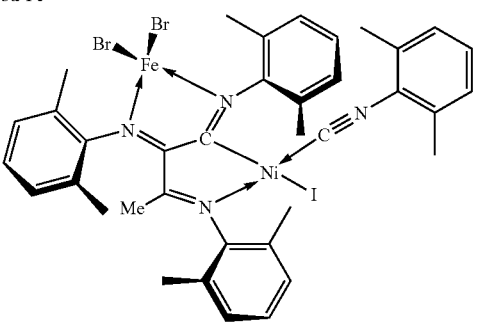 |
| 2 | 3a-Co 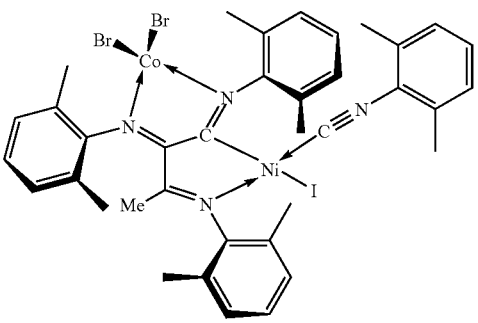 |

TABLE 2-continued
| Example | compound |
|---|---|
| 3 | 3b-Fe 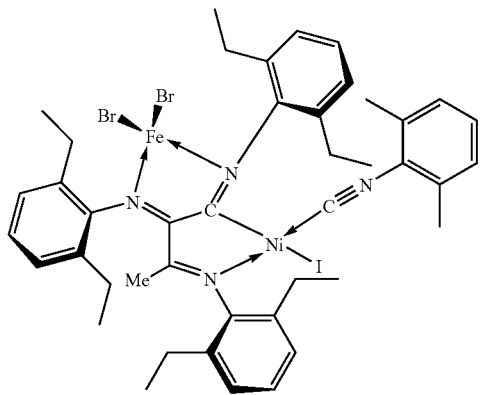 |
| 4 | 3c-Fe 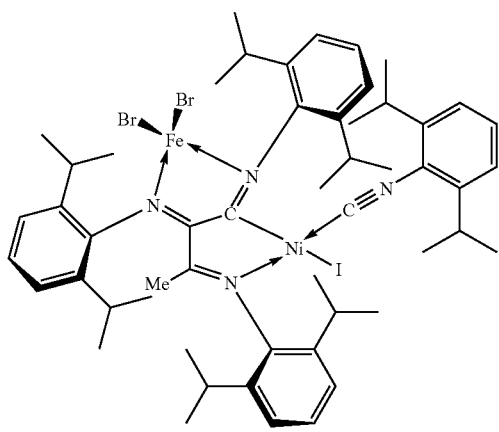 |
| 5 | 3d-Fe 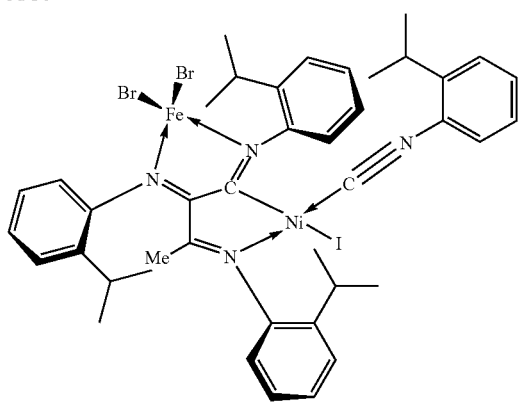 |

TABLE 2-continued

| Example | compound |
|---|---|
| 6 | 3e-Fe |
| 7 | 2a<br>+ NiBr$_2$(dme) |
| 8 | 2a<br>+ PtCl$_2$(cod) |
| 9 | 2a<br>+ PdMeCl(cod) |

TABLE 2-continued

| Example | compound |
|---|---|
| Comp. Ex.1 | A-Fe 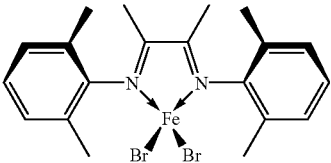 |
| Comp. Ex.2 | A-Co 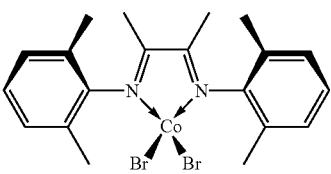 |

EXAMPLE 10

Polymerization of Ethylene Using Complex 3-Zn
[Synthesis of 3a-Zn]

By the same procedure as that employed for synthesis of complex 3a-Fe in Example 1, complex 3a-Zn was synthesized wherein zinc(II) dibromide was used instead of iron(II) dibromide. Thus a black crystal (complex 3a-Zn) was obtained in a yield of 0.54 g (77%).

Figure 3:
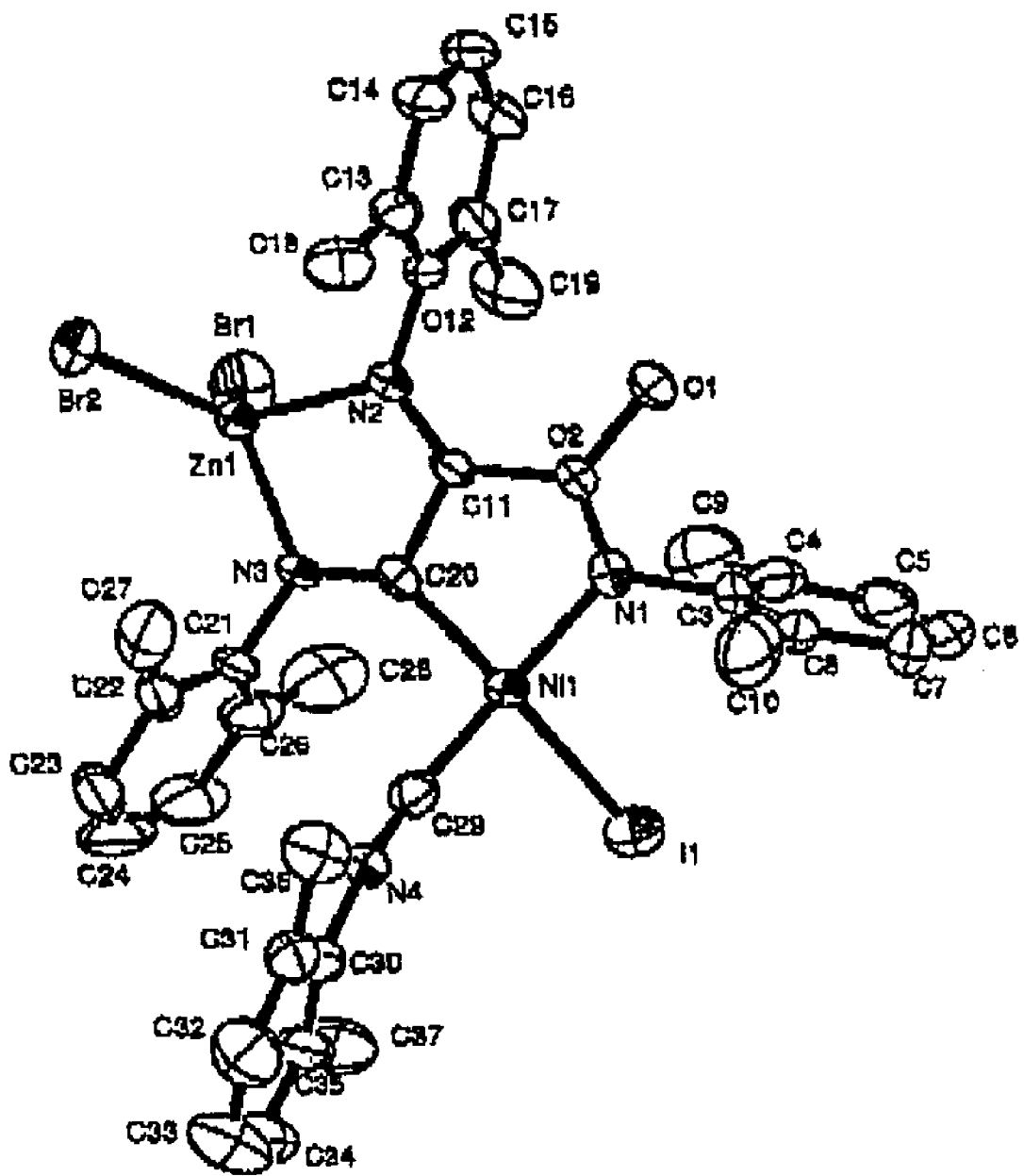
FIG. 3 is an ORTEP diagram of complex 3a-Zn [Iodo[1, 2,3-tris(2,6-dimethylphenylimino)butyl](2,6-dimethylphenylisocyanide)nickel(II)]dibromozinc(II).

X-ray structure analysis of complex 3a-Zn [Iodo[1,2,3-tris(2,6-dimethylphenylimino)butyl](2,6-dimethylphenyl-isocyanide)nickel(II)]dibromozinc(II)]was carried out, and an ORTEP diagram thereof Is shown in FIG. 3.

[Preparation of Catalyst]

In an argon atmosphere, a Schlenk flask was charged with complex 3a-Zn (160 mg, 168 µmol), and dry toluene (16.8 ml) was added to prepare a suspension of complex 3a-Zn. A solution of methylaluminoxane in toluene ("PMAO-S" available from TOSOH-FINECHEM Corp.; conc. 3.13 mol/liter) (10.7 ml, 33.6 mmol) was added, The mixture was stirred for 30 minutes to give a catalyst solution having a concentration of 10 mol/liter.

[Polymerization of Ethylene, at 30° C.]

In an argon atmosphere, a 2,000 ml pressure-resistant stainless steel vessel was charged with dry toluene (495 ml) and then the above-mentioned catalyst (5 ml, 50 µmol) was added. The content was stirred at 30° C. Then ethylene was blown into the pressure-resistant vessel in an amount such that the partial pressure of ethylene reached 1.0 MPa, to initiate polymerization. Polymerization was carried out for 60 minutes, while the temperature within the vessel was maintained at 30° C. Unreacted ethylene was removed, and methanol (5 ml) was added to stop the polymerization. The polymerization liquid was poured in hydrochloric acid-added methanol (300 ml) to precipitate a polymer. The polymer-containing liquid was filtered and the solid was dried to give polyethylene in a yield of 13.5 g (activity: 270 g/mmol) (Tm: 137.0° C., Mw: 260,000, Mw/Mn: 4.8).

EXAMPLE 11

[Polymerization of Ethylene, at 70° C.]

In an argon atmosphere, a 2,000 ml pressure-resistant stainless steel vessel was charged with dry toluene (495 ml) and then the same catalyst as used in Example 10 (5 ml, 50 µmol) was added. The content was stirred at 70° C. Then ethylene was blown into the pressure-resistant vessel in an amount such that the partial pressure of ethylene reached 1.0 MPa, to initiate polymerization. Polymerization was carried out for 60 minutes, while the temperature within the vessel was maintained at 70° C. Unreacted ethylene was removed, and methanol (5 ml) was added to stop the polymerization. The polymerization liquid was poured in hydrochloric acid-added methanol (300 ml) to precipitate a polymer. The polymer-containing liquid was filtered and the solid was dried to give polyethylene in a yield of 4.53 g (activity: 90.6 g/mmol) (Tm: 114.6° C., Mw: 84,000, Mw/Mn: 4 2).

EXAMPLE 12

[Preparation of Catalyst]

A catalyst was prepared by the same procedure as that employed in Example 10 wherein complex 3a-Fe was used instead of complex 3a-Zn. Thus a catalyst solution having a concentration of 10 mol/liter was obtained.

[Polymerization of Ethylene, at 30° C.]

In an argon atmosphere, a 2,000 ml pressure-resistant stainless steel vessel was charged with dry toluene (495 ml) and then the above-mentioned catalyst (5 ml, 50 µmol) was added. The content was stirred at 30° C. Then ethylene was blown into the pressure-resistant vessel in an amount such that the partial pressure of ethylene reached 1.0 MPa, to initiate polymerization. Polymerization was carried out for 60 minutes, while the temperature within the vessel was maintained at 30° C. Unreacted ethylene was removed, and methanol (5 ml) was added to stop the polymerization. The polymerization liquid was poured in hydrochloric acid-added methanol (300 ml) to precipitate a polymer. The polymer-containing liquid was filtered and the solid was dried to give polyethylene in a yield of 18.2 g (activity: 364 g/mmol) (Tm: 132.5° C., Mw: 310,000, Mw/Mn: 4.4).

EXAMPLE 13

[Polymerization of Ethylene, at 70° C.]

In an argon atmosphere, a 2,000 ml pressure-resistant stainless steel vessel was charged with dry toluene (495 ml) and then the same catalyst as used in Example 12 (5 ml, 50

µmol) was added. The content was stirred at 70° C. Then ethylene was blown into the pressure-resistant vessel in an amount such that the partial pressure of ethylene reached 1.0 MPa, to initiate polymerization. Polymerization was carried out for 60 minutes, while the temperature within the vessel was maintained at 70° C. Unreacted ethylene was removed, and methanol (5 ml) was added to stop the polymerization. The polymerization liquid was poured in hydrochloric acid-added methanol (300 ml) to precipitate a polymer. The polymer-containing liquid was filtered and the solid was dried to give polyethylene in a yield of 5.12 g (activity: 102.4 g/mmol) (Tm: 111.9° C., Mw: 72,000, Mw/Mn: 3.6).

EXAMPLE 14

Polymerization of Ethylene Using Complex 3a-Et-Zn

[Synthesis of Complex 2a-Et]

In an argon atmosphere, a Schlenk flask was charged with tetrakis(2,6-dimethylphenylisocyanide)nickel(0)(complex 1a)(0.76 g, 1.30 mmol), and dry benzene (30 ml) was added t dissolve complex 1a therein. Iodoethane (0.51 ml, 6.50 mmol was added, and reaction was carried out under reflux for 24 hours After completion of the reaction, the reaction mixture was cooled to room temperature, and filtered. The filtrate was evaporated to dryness under vacuum. The obtained solid was washed with hexane to give a reddish brown powder (complex 2a-Et) (yield 0.52 g, 54%).

$^1$H-NMR ($\delta$, $C_6D_6$): 6.98–6.95(m, 6H), 6.62–6.57(m, 3H), 6.46–6.44(m, 3H), 2.42(q, 2H, J=7.70 Hz), 2.36(s, 6H), 2.33 6H), 2.06(s, 6H), 1.95(s, 6H), 0.79(t, 3H, J=7.70 Hz)

[Synthesis of Complex 3a-Et-Zn]

In an argon atmosphere, a Schlenk flask was charged with complex 2a-Et (0.15 g, 0.20 mmol), and zinc(II) dibromide (78.7 mg, 0.35 mmol). Dry dichloromethane (10 ml) and ethanol (10 ml) were added. Reaction was carried out for 12 hours. After completion of the reaction, the solvent was removed by distillation. The residue was recrystallized from hot toluene to give a black powder (complex 3a-Et-Zn) (yield: 0.19 g).

[Preparation of Catalyst]

In an argon atmosphere, a Schlenk flask was charged with complex (3a-Et-Zn) (112 mg, 116 µmol). Dry toluene (4.2 ml) was added to prepare a suspension of complex 3a-Et-Zn. A solution of methylaluminoxane in toluene,("PMAO-S" available from TOSOH-FINECHEM Corp.; conc. 3.13 mol/liter) (7.4 ml, 23.2 mmol) was added, and the mixture was stirred for 30 minutes to give a catalyst solution having a concentration of 10 mol/liter.

[Polymerization of Ethylene]

In an argon atmosphere, a 2,000 ml pressure-resistant stainless steel vessel was charged with dry toluene (495 ml) and then the above-mentioned catalyst (5 ml, 50 µmol) was added. The content was stirred at 30° C. Then ethylene was blown into the pressure-resistant vessel in an amount such that the partial pressure of ethylene reached 1.0 MPa, to initiate polymerization. Polymerization was carried out for 60 minutes, while the temperature within the vessel was maintained at 30° C. Unreacted ethylene was removed, and methanol (5 ml) was added to stop the polymerization. The polymerization liquid was poured in hydrochloric acid-added methanol (300 ml) to precipitate a polymer. The polymer-containing liquid was filtered and the solid was dried to give polyethylene in a yield of 2.30 g (activity: 46.0 g/mmol) (Tm: 134.3° C.).

EXAMPLE 15

Polymerization of Ethylene Using Complex 3iPr—Zn

[Synthesis of Complex 2a-iPr]

In an argon atmosphere, a Schlenk flask was charged with tetrakis(2,6-dimethylphenylisocyanide)nickel(0)(complex 1a)(0.89 g, 1.52 mmol), and dry benzene (30 ml) was added to dissolve complex 1a therein. iPrI (1 ml, 10.02 mmol) was added, and reaction was carried out under reflux for 24 hours. After completion of the reaction, the reaction mixture was cooled to room temperature, and filtered. The filtrate was evaporated to dryness under vacuum. The obtained solid was washed with hexane to give a reddish brown powder (complex 2a-iPr) (yield: 0.81 g, 70%).

$^1$H-NMR ($\delta$, $C_6D_6$): 6.98–6.87(m, 6H), 6.62–6.57(m, 3H), 6.51–6.45(m, 3H), 2.69(sep, 1H, J=6.96 Hz), 2.43(s, 6H), 2.36(s, 6H), 2.05(s, 6H), 1.95(s, 6H), 1.21(d 6H, J=6.96 Hz)

[Synthesis of Complex 3a-iPr—Zn]

In an argon atmosphere, a Schlenk flask was charged with complex 2a-iPr (0.38 g, 0.50 mmol), and zinc(II) dibromide (0.11 g, 0.48 mmol). Dry dichloromethane (20 ml) and ethanol (5 ml) were added. Reaction was carried out for 12 hours. After completion of the reaction, the solvent was removed by distillation. The residue was recrystallized from hot toluene to give a black powder (complex 3a-iPr—Zn) (yield: 0.18 g).

[Preparation of Catalyst]

In an argon atmosphere, a Schlenk flask was charged with complex 3a-iPr—Zn) (249 mg, 254 µmol). Dry toluene (9.2 ml) was added to prepare a suspension of complex 3a-iPr—Zn. A solution of methylaluminoxane in toluene ("PMAO-S" available from TOSOH-FINECHEM Corp.; conc. 3.13 mol/liter) (16.2 ml, 33.6 mmol) was added, and the mixture was stirred for 30 minutes to give a catalyst solution having a concentration of 10 mol/liter.

[Polymerization of Ethylene]

In an argon atmosphere, a 2,000 ml pressure-resistant stainless steel vessel was charged with dry toluene (495 ml) and then the above-mentioned catalyst (5 ml, 50 µmol) was added. The content was stirred at 30° C. Then ethylene was blown into the pressure-resistant vessel in an amount such that the partial pressure of ethylene reached 1.0 MPa, to initiate polymerization. Polymerization was carried out for 60 minutes, while the temperature within the vessel was maintained at 30° C. Unreacted ethylene was removed, and methanol (5 ml) was added to stop the polymerization. The polymerization liquid was poured in hydrochloric acid-added methanol (300 ml) to precipitate a polymer. The polymer-containing liquid was filtered and the solid was dried to give polyethylene in a yield of 4.16 g (activity: 83.2 g/mmol) (Tm: 135.6° C.).

The results of polymerization in Examples 10 to 15 are shown in Table 3, and chemical structures of the compounds used in these examples are shown in Table 4.

TABLE 3

| Example No. | Ex. 10 | Ex. 11 | Ex. 12 | Ex. 13 | Ex. 14 | Ex. 15 |
|---|---|---|---|---|---|---|
| Tran. metal cpd*1 | 3a-Zn | 3a-Zn | 3a-Fe | 3a-Fe | 3a-Et-Zn | 3a-iPr-Zn |
| Amount (µmol) | 50 | 50 | 50 | 50 | 50 | 50 |
| Acti. cocata.*2 | PMAO | PMAO | PMAO | PMAO | PMAO | PMAO |
| Amount (mmol) | 10 | 10 | 10 | 10 | 10 | 10 |
| Ethylene pressure (MPa) | 1.0 | 1.0 | 1.0 | 1.0 | 1.0 | 1.0 |

TABLE 3-continued

| Example No. | Ex. 10 | Ex. 11 | Ex. 12 | Ex. 13 | Ex. 14 | Ex. 15 |
|---|---|---|---|---|---|---|
| Polymn. time (min) | 60 | 60 | 60 | 60 | 60 | 60 |
| Polymn. temp. (° C.) | 30 | 70 | 30 | 70 | 30 | 30 |
| Polymer yield (g) | 13.5 | 4.53 | 18.2 | 5.12 | 2.30 | 4.16 |
| Activity (g/mmol) | 270 | 90.6 | 364 | 102.4 | 46.0 | 83.2 |
| Melting point (° C.) | 137.0 | 114.6 | 132.5 | 111.9 | 134.3 | 135.6 |
| Mn × 10³ | 54 | 20 | 70 | 20 | — | — |
| Mw × 10³ | 260 | 84 | 310 | 72 | — | — |
| Mw/Mn | 4.8 | 4.2 | 4.4 | 3.6 | — | — |

Note,
*1 Transition metal compound
*2 Activating cocatalyst

TABLE 4

| Example | compound |
|---|---|
| 10, 11 | 3a-Zn |
| 12, 13 | 3a-Fe |
| 14 | 3a-Et—Zn |
| 15 | 3a-IPr—Zn |

EXAMPLE 16

Polymerization of Ethylene Using Complex 6a-Me

[Synthesis of Complex 4a]

In an inert gas atmosphere, a three-necked flask equipped with a Dean-Stark trap, a Dimroth condenser and a three-way cock was charged with dry toluene (200 ml), and then, paratoluenesulfonic acid monohydrate (5.6 g, 29.4 mmol), 2'-bromoacetophenone (7.26 ml, 53.0 mmol) and 2,6-dimethylaniline (6.64 ml, 53.9 mmol) were added. Reaction was carried out for 8 hours under reflux. The reaction liquid was cooled to room temperature, and then poured into an aqueous sodium hydrogen carbonate (10 g) solution (200 ml) and stirred for 20 minutes. The organic phase was separated, and then, dried over sodium sulfate, concentrated and then distilled under vacuum (0.1 mmHg, 125° C.) to give yellow oily ligand precursor 4a (yield: 2.45 g, 15%).

$^1$H-NMA (δ, $C_6D_6$, 400 MHz): 7.34(dd, 1H, J=7.70 Hz, 1.47 Hz, 2 or 5-H(Ar)), 7.30(dd, 1H, J=8.06 Hz, 1.10 Hz, 2 or 5-H(Ar)), 7.04(d, 2H, J=7.33 Hz, 3, 5-H(N—Ar)), 6.97–6.93(m, 2H, 3,5-H)(N—Ar) and 3 or 4-H(Ar)). 6.73 (dt, 1H, J=7.33, 1.83, 3 or 4-H(Ar)), 2.15(s, 6H, 2,6-Me (N—Ar)), 1.78(s, 3H, Me(C=N—Ar))

[Synthesis of Complex 5a]

In an inert gas atmosphere, a Schlenk flask (100 ml) was charged with bis(1,5-cyclooctadiene)nickel(0)(0.55 g, 1.99 mmol), and dry benzene (20 ml) was added to prepare a suspension of bis(1,5-cyclooctadiene)nickel(0). Dimethylphenyl-phosphine (0.30 ml, 2.13 mmol) was added, and reaction was carried out at room temperature for 1 hour. In another Schlenk falsk (50 ml), a solution of ligand precursor 4a (0.60 g, 2.00 mmol) in dry benzene (10 ml) was prepared. The suspension of ligand precursor 4a was added to the solution of bis(1,5-cyclooctadiene)nickel(0). The mixture was allowed to react at room temperature for 12 hours. After completion of the reaction, the reaction mixture was filtered, and the solvent was removed under vacuum from the filtrate to obtain reddish brown oil. The oil was reprecipitated from diethyl ether/pentane to give a reddish brown powder (complex 5a; yield 0.44 g, 35%).

$^1$H-NMR (δ, $C_6D_6$, 400 MHz): 7.52(d, 4H, J=6.23 Hz), 7.07–7.00(m, 8H), 6.75(t, 1H, J=7.31 Hz), 6.63(t, 1H, J=6.96 Hz), 6.48(d, 1H, J=7.69 Hz), 2.29(s, 6H, 2,6-Me (N—Ar)), 1.80(s, 3H Me(C=N—Ar)), 1.18(s, 12H, $PMe_2Ph$)

[Synthesis of Complex 6a-Me]

In an inert gas atmosphere, a Schlenk flask (50 ml) was charged with complex 5a (0.13 g, 0.25 mmol), and dry benzene (1 ml) was added to dissolve complex 5a. In another Schlenk falsk a solution (2.52 ml) of 2,6-dimethylphenylisocyanide (0.1 mol/liter) in benzene was prepared. The solution of 2,6-dimethylphenylisocyanide was added to the solution of complex 5a. The mixture was allowed to react at room temperature for 12 hours. After completion of the reaction, the reaction liquid was filtered and the solvent was removed under vacuum from the filtrate. The residue was washed with hexane to give a dark green powder (complex 6a-Me: yield: 0.058 g, 46%).

$^1$H-NMR ($\delta$, $C_6D_6$, 400 MHz): 7.62(br, 4H), 6.96–6.75 (m, 11H), 2.17(s, 6H, 2,6-Me(N—Ar)), 1.70–1.55(br, 14H, (Me(C=N—Ar), PMe$_2$Ph, 2,6-Me(Ni—C=N—Ar))

[Preparation of Catalyst Solution]

In an inert gas atmosphere, a Schlenk flask (100 ml) was charged with complex 6a-Me (0.334 g, 530 μmol). Dry toluene (53 ml) was added to prepare a solution of complex 6a-Me.

[Polymerization of Ethylene]

In an inert gas atmosphere, a 100 ml pressure-resistant glass vessel was charged with dry toluene (36.5 ml) and then the above-mentioned catalyst solution (10 ml, 100 μmol) was added. Then a solution of tris (pentafluorophenyl) borane in hydrocarbon (($C_6F_5$)$_3$B/Isopar-E, available from TOSOH-FINECHEM Corp., 0.079 mol/liter, 2.52 ml, 200 μmol) was added to the catalyst solution. The mixture was stirred for 30 minutes. Then a solution of methylaluminoxane in toluene ("PMAO-S" available from TOSOH-FINECHEM Corp.; conc. 2.85 mol/liter, 0.35 ml, 1 mmol) was added, and the mixture was stirred for 30 minutes. Then ethylene was blown into the pressure-resistant vessel in an amount such that the partial pressure of ethylene reached 1.0 MPa, to initiate polymerization. Polymerization was carried out for 30 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 0.11 g (activity: 1.1 g/mmol) (Tm: 127.5° C., Mw: 420,000, Mw/Mn: 100(multimodal)).

EXAMPLE 17

[Preparation of Catalyst Solution]

In an inert gas atmosphere, a Schlenk flask was charged with complex 5a (0.11 g, 173 μmol). Dry toluene (22.9 ml) was added to prepare a solution of complex 5a.

[Polymerization of Ethylene]

In an inert gas atmosphere, a 100 ml pressure-resistant glass vessel was charged with dry toluene (23.0 ml) and then the above-mentioned catalyst solution (10 ml, 75.5 μmol) was added. Then a solution (1 ml, 100 μmol) of 2,6-diisopropylphenylisocyanide (0.1 mol/liter) in diethyl ether was added, and the mixture was stirred for 30 minutes. Then a solution of tris(pentafluorophenyl)borane in hydrocarbon (($C_6F_5$)$_3$B/Isopar-E, available from TOSOH-FPNECHEM Corp., 0.079 mol/liter, 2.52 ml, 200 μmol) was added, and the mixture was stirred for 30 minutes. Then a solution of methylaluminoxane in toluene ("PMAO-S" available from TOSOH-FINECHEM Corp.; conc. 2.85 mol/liter, 3.5 ml, 10 mmol) was added, and the mixture was stirred for 30 minutes. Then ethylene was blown into the pressure-resistant vessel in an amount such that the partial pressure of ethylene reached 1.0 MPa, to Initiate polymerization. Polymerization was carried out for 180 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 0.59 g (activity: 7.8 mmol) (Tm: 129.3° C., Mw: 14,000, Mw/Mn: 2.7).

EXAMPLE 18

[Polymerization of Ethylene]

In an inert gas atmosphere, a 100 ml pressure-resistant glass vessel was charged with dry toluene (23.0 ml) and a solution (10 ml, 100 μmol) of complex 5a (10 mol/liter) in benzene. Then a solution (1 ml, 100 μmol) of,2,6-diisopropylphenylisocyanide (0.1 mol/liter) in diethyl ether was added, and the mixture was stirred for 30 minutes. Then a solution of tris(pentafluorophenyl)borane in hydrocarbon (($C_6F_5$)$_3$B/Isopar-E, available from TOSOH-FINECHEM Corp., 0.079 mol/liter, 5.1 ml, 100 μmol) was added, and the mixture was stirred for 30 minutes. Then a solution of methylaluminoxane in toluene ("PMAO-S" available from TOSOH-PINECHEM Corp.; conc. 2.85 mol/liter, 3.5 ml, 10 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 60 minutes. Unreacted ethylene was removed under vacuum, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give a trace amount of polyethylene.

EXAMPLE 19

Polymerization of Ethylene Using complex 6b

[Synthesis of Complex 4b]

In an inert gas atmosphere, a three-necked flask equipped with a Dean-Stark trap, a Dimroth condenser and a three-way cook was charged with dry toluene (150 ml), and then, paratoluenesulfonic acid monohydrate (4.0 g, 21.0 mmol), 2'-bromoacetophenone (5.0 ml, 37.0 mmol) and 2-biphenylamine (8.0 g, 47.3 mmol) were added. Reaction was carried out for 8 hours under reflux. The reaction liquid was cooled to room temperature, and then poured into an aqueous sodium hydrogen carbonate (10 g) solution (200 ml) and stirred for 20 minutes. The organic phase was separated, and then, dried over sodium sulfate, and then distilled under vacuum to remove the solvent. The residue was purified in a silica gel column using diethyl ether as developing agent to give reddish brown oily ligand precursor 4b (yield: 8.71 g, 66%).

$^1$H-NMR ($\delta$, $C_6D_6$, 400 MHz): 7.40–6.78(m, 13H), 1.82 (s, 3H, Me(C=N—Ar))

[Synthesis of Complex 5b]

In an inert gas atmosphere, a Schlenk flask (100 ml) was charged with bis(1,5-cyclooctadiene)nickel(0)(0.58 g, 2.12 mmol), and dry benzene (15 ml) was added to prepare a suspension of bis(1,5-cyclooctadiene)nickel(0). Dimethylphenylphosphine (0.78 ml, 4.20 mmol) was added, and reaction was carried out at room temperature for 1 hour. In another Schlenk falsk (50 ml), a solution of ligand precursor 4b (0.76 g, 2.12 mmol) in dry benzene (10 ml) was prepared.

The solution of ligand precursor 4b was added to the suspension of bis(1,5-cyclooctadiene)nickel(0). The mixture was allowed to react at room temperature for 12 hours. After completion of the reaction, the reaction mixture was filtered, and the solvent was removed under vacuum from the filtrate to obtain reddish brown oil. The oil was reprecipitated from pentane to give a reddish brown powder (complex 5b; yield 1.44 g, 83%).

$^1$H-NMR ($\delta$, $C_6D_6$, 400 MHz): 7.40–6.78(m, 33H), 1.82 (s, 3H, Me(C=N—Ar)), 1.55(s, 6H, $PMePh_2$)

[Preparation of Catalyst Solution]

In an inert gas atmosphere, a Schlenk flask (100 ml) was charged with complex 5b (0.104 g, 129 μmol). Dry toluene (12.9 ml) was added to prepare a solution of complex 6b.

[Polymerization of Ethylene]

In an inert gas atmosphere, a 100 ml pressure-resistant glass vessel was charged with dry toluene (23.0 ml) and then the above-mentioned catalyst solution (10 ml, 100 μmol) was added. Then a solution (1 ml, 100 μmol) of 2,6-dimethylphenylisocyanide (0.1 mol/liter) in benzene was added, and the mixture was stirred for 30 minutes. Then a solution of tris(pentafluorophenyl)-borane in hydrocarbon (($C_6F_5)_3$B/Isopar-E, available from TOSOH-FINECHEM Corp., 0.079 mol/liter, 5.1 ml, 400 μmol) was added, and the mixture was stirred for 30 minutes. Then a solution of methylaluminoxane in toluene ("PMAO-S" available from TOSOH-PINECHEM Corp.; conc. 2.85 mol/liter, 3.5 ml, 10 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 30 minutes, Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 0.099 g (activity: 1.0 g/mmol) (Tm: 113.2° C., 119.9° C., Mw: 51,000, Mw/Mn: 6.6).

EXAMPLE 20

Polymerization of Ethylene Using Complex 5b

[Preparation of Catalyst Solution]

In an inert gas atmosphere, a Schlenk flask was charged with complex 5b (0.18 g, 0.22 mmol) prepared in Example 19. Dry toluene (22.0 ml) was added to prepare a solution of complex 5b.

[Polymerization of Ethylene]

In an inert gas atmosphere, a 100 ml pressure-resistant glass vessel was charged with dry toluene (23.0 ml) and then the above-mentioned catalyst solution (10 ml, 100 μmol) was added. Then a solution (1 ml, 100 μmol) of 2,6-diisopropylphenylisocyanide (0.1 mol/liter) in benzene was added, and the mixture was stirred for 30 minutes. Then a solution of tris(pentafluorophenyl)borane in hydrocarbon (($C_6F_5)_3$B/Isopar-E, available from TOSOH-FINECHEM Corp., 0.079 mol/liter, 5.1 ml, 400 μmol) was added, and the mixture was stirred for 30 minutes. Then a solution of methylaluminoxane in toluene ("PMAO-S" available from TOSOH-PINECHEM Corp.; conc. 2.85 mol/liter, 3.5 ml, 10 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 30 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 0.019 g (activity; 0.2 g/mmol) (Tm: 129.0° C. Mw: 120,000, Mw/Mn: 26).

EXAMPLE 21

Polymerization of Ethylene

[Synthesis of Complex 7]

In an inert gas atmosphere, a 100 ml Schlenk flask was charged with tetrachrolobis(tetrahydrofuran)titanium(IV) (0.25 g, 0.76 mmol), and then dry tetrahydrofuran (20 ml) was added to prepare a suspension of tetrachrolobis-(tetrahydrofuran)titanium(IV). Then the suspension was cooled to −78° C. In another schlenk flask (100 ml), a solution of N-2,6-dimethylphenyl)-2'-bromoacetophenoneimine (4a) (0.51 g, 1.69 mmol) in dry tetrahydrofuran (40 ml) was prepared, and then, at −78° C., a solution (1.18 ml) of n-butyllithium (1.59 mol/liter) in hexane was added. The mixture was stirred for 1 hour while the temperature was maintained at −78° C. Thereafter, the resultant reaction liquid was added to the above-mentioned suspension of tetrachrolobis(tetrahydrofuran)titanium(IV). The mixture was allowed to react for 12 hours while the temperature naturally rose to room temperature. After completion of the reaction, the solvent was removed under vacuum, and the residue was dissolved in benzene. Then the solution was filtered, and the solvent was removed by distillation to give a blackish brown powder (complex 7; yield 0.26 g, 61%).

$^1$H-NMR ($\delta$, $C_6D_5$, 400 MHz): 7.96–6.92(m, 14H), 1.99 (s, 12H, Ar-Me), 1.69(s, 6H)

[Preparation of Catalyst Solution]

In an inert gas atmosphere, a Schlenk flask was charged with complex 7 (0.15 g) and dry benzene (20 ml) was added to dissolve complex 7 therein. In another Schlenk flask, a solution of 2,6-dimethylphenylisocyanide (0.07 g) in dry benzene (20 ml) was prepared, and then, this solution was added to the solution of complex 7. The mixture was allowed to react at room temperature for 6 hours. Then the reaction liquid was filtered, and the solvent was removed under vacuum from the filtrate. The residue was washed with hexane to give a blackish brown powder (0.11 g).

The blackish brown powder (41.2 mg) was dissolved in dry toluene (495 ml), A solution of methylaluminoxane in toluene ("PMAO-S" available from TOSOH-FINECHEM Corp.; conc. 2.85 mol/liter, 4.39 ml, 12.5 mmol) was added, and the mixture was stirred for 30 minutes to prepare a catalyst solution.

[Polymerization of Ethylene]

In an inert gas atmosphere, the above-mentioned catalyst solution was placed in a 2,000 ml pressure-resistant stainless steel vessel, and maintained at 30° C. Then ethylene was blown into the pressure-resistant vessel in an amount such that the partial pressure of ethylene reached 1.0 MPa, to initiate polymerization. Polymerization was carried out for 60 minutes. Unreacted ethylene was removed, and methanol (5 ml) was added to stop the polymerization. The solvent was removed from the polymerization liquid, and the polymerization liquid was poured in 10% hydrochloric acid-added methanol (300 ml) to precipitate a polymer. The polymer-containing liquid was filtered and the solid was dried under vacuum to give polyethylene in a yield of 9.7 g (Tm: 138.8° C.).

EXAMPLE 22

Polymerization of Ethylene
[Synthesis of Complex 8]

In an inert gas atmosphere, a 100 ml Schlenk flask was charged with zirconium(IV) chloride (0.35 g, 1.5 mmol), and then dry tetrahydrofuran (20 ml) was added to prepare a suspension of zirconium(IV) chloride. Then the suspension was cooled to −78° C. In another Schlenk flask (100 ml), a solution of N-2,6-dimethylphenyl)-2'-bromoacetophenoneimine (4a). (0.90 g, 3.0 mmol) in dry tetrahydrofuran (40 ml) was prepared, and then, at −78° C., a solution (2 ml) of n-butyllithium (1.59 mol/liter) in hexane was added. The mixture was stirred for 1 hour while the temperature was maintained at −78° C. Thereafter, the resultant reaction liquid was added to the above-mentioned zirconium(IV) chloride solution. The mixture was allowed to react for 12 hours while the temperature naturally rose to room temperature. After completion of the reaction, the solvent was removed under vacuum, and the residue was dissolved in benzene. Then the solution was filtered, and the solvent was removed by distillation to give a blackish brown powder (complex 8: yield 0.61 g, 67%).

$^1$H-NMR (δ, $C_6D_6$, 400MHz): 7.97–6.97(m, 14H), 1.98(s, 12H, Ar-Me), 1.69(s, 6H)

[Preparation of Catalyst Solution]

In an inert gas atmosphere, a Schlenk flask was charged with complex 8 (0.45 g) and dry benzene was added to dissolve complex 8 therein. In another Schlenk flask, a solution of 2,6-dimethylphenylisocyanide (0.12 g) in dry-benzene (20 ml) was prepared, and then, this solution was added to the solution of complex 8. The mixture was allowed to react at room temperature for 6 hours. Then the reaction liquid was filtered, and the solvent was removed under vacuum from the filtrate. The residue was washed with hexane to give a blackish brown powder (0.15 g).

The blackish brown powder (43 mg) was dissolved in dry toluene (495 ml). A solution of methylaluminoxane in toluene ("PMAO-S" available from TOSOH-FINECHEM Corp.; conc. 2.85 mol/liter, 4.39 ml, 12.5 mmol) was added, and the mixture was stirred for 30 minutes to prepare a catalyst solution.

[Polymerization of Ethylene]

In an inert gas atmosphere, the above-mentioned catalyst solution (10 ml, 10 μmol) was placed in a 2,000 ml pressure-resistant stainless steel vessel, and maintained at 30° C. Then ethylene was blown into the pressure-resistant vessel in an amount such that the partial pressure of ethylene reached 1.0 MPa, to initiate polymerization. Polymerization was carried out for 60 minutes. Unreacted ethylene was removed, and methanol (5 ml) was added to stop the polymerization. The solvent was removed from the polymerization liquid, and the polymerization liquid was poured in 10% hydrochloric acid-added methanol (300 ml) to precipitate a polymer. The polymer-containing liquid was filtered and the solid was dried under vacuum to give polyethylene in a yield of 14.01 g (Tm: 139.7° C.).

The results of polymerization in Examples 16 to 22 are shown in Table 5, and chemical structures of the compounds used in these examples are shown in Table 6.

TABLE 5

| Example No. | Ex. 16 | Ex. 17 | Ex. 18 | Ex. 19 | Ex. 20 | Ex. 21 | Ex. 22 |
|---|---|---|---|---|---|---|---|
| Tran. metal cpd*1 | 6a-Me | 5a-CN-Me | 5a-CN-iPr | 5b-CN-Me | 5b-CN-iPr | 7 CN-Me | 8 CN-ME |
| Amount (μmol) | 100 | 75.5 | 100 | 100 | 100 | 5 | 5 |
| Acti. cocata.*2 | PMAO | PMAO | PMAO | PMAO | PMAO | PMAO | PMAO |
| Amount (mmol) | 10 | 10 | 10 | 10 | 10 | 12.5 | 12.5 |
| Addive | $B(C_6F_5)_3$ | $B(C_6F_5)_3$ | $B(C_6F_5)_3$ | $B(C_6F_5)_3$ | $B(C_6F_5)_3$ | — | — |
| Amount (μmol) | 200 | 200 | 400 | 400 | 400 | — | — |
| Ethylene pressure (MPa) | 1.0 | 1.0 | 0.8 | 0.8 | 0.8 | 1.0 | 1.0 |
| Polymn. time (min) | 30 | 180 | 30 | 30 | 30 | 60 | 60 |
| Polymn. temp. (° C.)*3 | r.t. | r.t. | r.t. | r.t. | r.t. | 30 | 30 |
| Polymer yield (g) | 0.11 | 0.59 | trace | 0.0099 | 0.0192 | 9.7 | 14.1 |
| Activity (g/mmol) | 1.1 | 7.8 | — | 0.10 | 0.19 | 1940 | 2820 |
| Melting point (° C.) | 127.5 | 129.3 | — | 113.2 119.9 | 129.3 | 138.8 | 139.7 |
| Mn × 10$^3$ | 4.2 | 5.2 | — | 7.7 | 4.6 | — | — |
| Mw × 10$^3$ | 420 | 14 | — | 51 | 120 | — | — |
| Mw/Mn | 100 *4 | 2.7 | — | 6.6 | 26 | — | — |

Note,

*1 Transition metal compound; CN-Me = CN-(2,6-Me$_2$-C$_6$H$_3$), CN-iPr = CN-(2,6-iPr$_2$-C$_6$H$_3$)

*2 Activating cocatalyst

*3 Polymerization temperature: r.t. = room temperature

*4 Multimodal

TABLE 6

| Example | compound |
|---|---|
| 16 | 4a |
| 19 | 4b |
| 16, 17, 18 | 5a |
| 19, 20 | 5b |
| 16 | 6a-Me |

TABLE 6-continued

| Example | compound |
|---|---|
| 21 | 7 |
| 22 | 8 |

EXAMPLE 23

Polymerization of Ethylene Using Complex 11a

[Synthesis of Diisopropyl(2-bromopheoxy)phosphine (9)]

In an inert gas atmosphere, sodium hydride (0.42 g, 17.5 mmol) was placed in a Schlenk flask, and then dry diethyl ether (20 ml) was added. The flask was cooled to 0° C. in an ice bath. Orthobromophenol (2.03 ml, 17.5 mmol) was dropwise added. After completion of the dropwise-addition, reaction was carried out for 2 hours. Then, using a dropping funnel, a solution of diisopropylchlorophosphine (2.7 ml. 17.0 mmol) in diethyl ether (20 ml) was dropwise-added over a period of 10 minutes. Recation was carried out at room temperature for 12 hours. The reaction liquid was filtered to remove an inorganic salt. Then the filtrate was concentrated under vacuum, and purified by distillation under vacuum ($3.0 \times 10^{-4}$ Torr, 65–70° C.) to colorless oily ligand precursor 9.

$^1$H-NMR (δ, $C_6D_6$, 400 MHz): 7.41–7.35(m, 2H), 6.91–6.87(m, 1H), 6.48–6.44(m, 1H), 1.78(sep-d, 2H), $J_{HH}$=6.97 Hz, $J_{PH}$=7.32 Hz), 1.14(dd, 6H, $J_{HH}$=6.97 Hz, $J_{PH}$=15.76 Hz)

[Synthesis of Complex 10]

In an inert gas atmosphere, a Schlenk flask (100 ml) was charged with bis(1.5-cyclooctadiene)nickel(0)(0.37 g, 1.35 mmol), and dry benzene (10 ml) was added to prepare a suspension of bis(1,5-cyclooctadiene)nickel(0). Methyl-diphenyl-phosphine (0.50 ml, 2.70 mmol) was added, and reaction was carried out at room temperature for 1 hour. In another Schlenk falsk (50 ml), a solution of ligand precursor 7 (0.39 g, 1.35 mmol) in dry benzene (10 ml) was prepared. The solution of ligand precursor 7 was added to the suspension of bis(1,5-cyclooctadiene)nickel(0). The mixture was allowed to react at room temperature for 12 hours. After completion of the reaction, the reaction mixture was filtered, and the solvent was removed under vacuum from the filtrate to obtain reddish brown oil. The oil was reprecipitated from pentane to give a reddish brown powder (complex 10; yield 0.39 g, 53%).

$^1$H-NMR (δ, $C_6D_6$, 400 MHz): 7.71(br, 4H), 7.02–6.80 (m, 9H), 6.36(t, 1H), 2.46(sep-d, 2H, $J_{HH}$=6.96 Hz, $J_{PH}$=14.28 Hz), 1.50(dd, 6H, $J_{HH}$=6.96 Hz, $J_{PH}$=16.86 Hz), 1.28(dd, 6H, $J_{HH}$=6.96 Hz, $J_{PH}$=14.29 Hz)

[Synthesis of Complex 11a]

In an inert gas atmosphere, a Schlenk flask (50 ml) was charged with complex 10 (0.16 g, 0.29 mmol), and dry benzene (10 ml) was added to dissolve complex 10. In another Schlenk falsk, a solution (0.57 ml) of 2,6-diisopropylphenylisocyanide (0.5 mol/liter) in benzene was prepared. The solution of 2,6-diisopropylphenylisocyanide was added to the solution of complex 10. The mixture was allowed to react at room temperature for 12 hours. After completion of the reaction, the reaction liquid was filtered and the solvent was removed under vacuum from the filtrate. The residue was recrystallized from pentane to give a reddish brown powder (complex 11a; yield: 0.125 g, 43%).

$^1$H-NMR (δ$C_6D_6$, 400 MHz): 7.65–7.42(m, 4H), 7.12–7.03(m, 9H), 6.83–6.66(m, 2H), 6.25(br, 1H), 3.22(br, 2H), 2.25(br, 2H), 1.44(dd, 6H, $J_{HH}$=7.33 HZ, $J_{PH}$=18.69 Hz), 1.18(dd 6H, $J_{HH}$=6.96 Hz, $J_{PH}$=14.66 Hz), 1.12(d, 12H, $J_{HH}$=6.96)

[Preparation of Catalyst Solution]

In an inert gas atmosphere, a Schlenk flask (100 ml) was charged with complex 11a (0.125 g, 169 μmol). Dry toluene (16.9 ml) was added to prepare a solution of complex 11a.

[Polymerization of Ethylene]

In an inert gas atmosphere, a 100 ml pressure-resistant glass vessel was charged with dry toluene (36.5 ml) and then the above-mentioned catalyst solution (10 ml, 100 μmol) was added. Then a solution of tris(pentafluorophenyl)borane in hydrocarbon (($C_6F_5$)$_3$B/Isopar-E, available from TOSOH-FINECHEM Corp., 0.079 mol/liter, 5.1 ml, 400 μmol) was added to the catalyst solution. The mixture was stirred for 30 minutes. Then a solution of methylaluminoxane in toluene ("PMAO-S" available from TOSOH-FINECHEM Corp. conc. 2.85 mol/liter. 3.5 ml, 10 mmol) was added, and the mixture was stirred for 30 minutes. Then ethylene was blown into the pressure-resistant vessel in an amount such that the partial pressure of ethylene reached 0.8 MPa. to initiate polymerization. Polymerization was carried out for 30 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 0.95 g (activity: 9.5 g/mmol) (Tm: 86.0° C., 115° C., Mw: 64,000, Mw/Mn: 2.6).

EXAMPLE 24

Polymerization of Ethylene

[Preparation of Catalyst Solution]

In an inert gas atmosphere, a Schlenk flask (100 ml) was charged with complex 10 (0.116 g, 212 μmol). Dry toluene (21.2 ml) was added to prepare a solution of complex 10 having a concentration of 10 mmol/liter.

[Polymerization of Ethylene]

In an inert gas atmosphere, a 100 ml pressure-resistant glass vessel was charged with dry toluene (23.0 ml) and then the above-mentioned catalyst solution (10 ml, 100 μmol) was added. Then a solution (1 ml, 100 μmol) of 2,6-dimethylphenylisocyanide (0.1 mol/ liter) in benzene was added, and the mixture was stirred for 30 minutes. Then a solution of tris(pentafluorophenyl)-borane in hydrocarbon (($C_6F_5$)$_3$B/Isopar-E, available from TOSOH-FINECHEM Corp., 0.079 mol/liter, 5.1 ml, 400 μmol) was added, and the mixture was stirred for 30 minutes. Then a solution of methylaluminoxane in toluene ("PMAO-S" available from TOSOH-FINECHEM Corp.; conc. 2.85 mol/liter, 3.5 ml, 10 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 30 minutes. Unreacted ethylene was removed, and methanol (5 ml) was added to stop the polymerization. The polymerization liquid was poured in water (300 ml) to precipitate a polymer. The organic phase was separated, and dried over sodium sulfate. Then the solvent was removed by distillation to give viscous oily material in a yield of 0.61 g.

EXAMPLE 25

Polymerization of Ethylene

[Polymerization of ethylene ]

In an inert gas atmosphere, a 100 ml pressure-resistant glass vessel was charged with dry toluene (23.0 ml) and then the above-mentioned solution of complex 10 (10 ml, 100 μmol) in toluene was added. Then a solution (1 ml, 100 μmol) of 2-methyl-6-isopropylphenylisocyanide (0.1 mol/ liter) in benzene was added, and the mixture was stirred for 30 minutes. Then a solution of tris(pentafluorophenyl)borane in hydrocarbon (($C_6F_5$)$_3$B/Isopar-E, available from TOSOH-FINECHEM Corp., 0.079 mol/liter, 5.1 ml, 400 μmol) was added, and the mixture was stirred for 30 minutes. Then a solution of methylaluminoxane in toluene ("PMAO-S" available from TOSOH-FINECHEM Corp.; conc. 2.85 mol/liter, 3.5 ml, 10 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 30 minutes. Unreacted ethylene was removed, and methanol (5 ml) was added to stop the polymerization. The polymerization liquid was poured in water (300 ml) to precipitate a polymer. The organic phase was separated, and dried over sodium sulfate. Then the solvent was removed by distillation to give viscous oily material in a yield of 0.70 g.

The results of polymerization:in Examples 23 to 25 are shown in Table 7, and chemical structures of the compounds used in these examples are shown in Table 8.

TABLE 7

| Example No. | Ex. 23 | Ex. 24 | Ex. 25 |
|---|---|---|---|
| Tran. metal cpd *1 | 11a | 10 | 10 |
|  |  | CN—Me | CN—Me—iPr |
| Amount (μmol) | 100 | 100 | 100 |
| Acti. cocata. *2 | PMAO | PMAO | PMAO |
| Amount (mmol) | 10 | 10 | 10 |
| Additve | B($C_6F_5$)$_3$ | B($C_6F_5$)$_3$ | B($C_6F_5$)$_3$ |
| Amount (μmol) | 400 | 400 | 400 |
| Ethylene pressure (MPa) | 0.8 | 0.8 | 0.8 |
| Polymn. time (min) | 30 | 30 | 30 |
| Polymn. temp. (° C.)*3 | r.t. | r.t. | r.t. |
| Polymer yield (g) | 0.95 | 0.61 | 0.70 |
| Activity (g/mmol) | 9.5 | 6.1 | 7.0 |

TABLE 7-continued

| Example No. | Ex. 23 | Ex. 24 | Ex. 25 |
|---|---|---|---|
| Melting point (° C.) | 86.0 | — | — |
|  | 115.0 |  |  |
| Mn × $10^3$ | 24 | — | — |
| Mw × $10^3$ | 64 | — | — |
| Mw/Mn | 2.6 | — | — |

Note, *1 Transition metal compound: CN—Me = CN—(2-Me$_3$—C$_6$H$_4$)
CN—Me—iPr = CN—(2-Me-6-iPr—C$_6$H$_3$)
*2 Activating cocatalyst
*3 Polymerization temperature: r.t. = room temperature

TABLE 8

| Example | compound |
|---|---|
| 23 | 9 |
| 23 24 25 | 10 |
| 23 | 11a |

EXAMPLE 26

Polymerization of Ethylene Using Complex 2a
[Polymerization of Ethylene]

In an inert gas atmosphere, a 100 ml pressure-resistant stainless steel vessel was charged with dry toluene (36.5 ml), and then a solution (1 ml, 10 μmol) of complex 2a (10 mmol/liter) in toluene was added. A solution of methylaluminoxane in toluene ("PMAO-S" available from TOSOH-FINECHEM Corp.; conc. 2.85 mol/liter, 0.35 ml, 1 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 30 minutes. Unreacted ethylene was removed, and methanol (5 ml) was added to stop the polymerization, The polymerization liquid was poured in 10% hydrochloric acid-added methanol (300 ml) to precipitate a polymer. The polymer-containing liquid was filtered and the solid was dried under vacuum to give polyethylene in a yield of 0.25g (activity: 25 g/mmol) (Tm: 128° C., Mw: 330,000, Mw/Mn: 3.3).

EXAMPLE 27

Polymerization of Ethylene Using Complex 2b
[Polymerization of Ethylene]

In an inert gas atmosphere, a 100 ml pressure-resistant stainless steel vessel was charged with dry toluene (36.5 ml), and then a solution (1 ml, 10 μmol) of complex 2b (10 mmol/liter) in toluene was added. A solution of methylaluminoxane in toluene ("PMAO-S" available from TOSOH-FINECHEM Corp.; conc. 2.85 mol/liter, 0.35 ml, 1 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 30 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 0.60 g (activity: 60 g/mmol) (Tm: 116° C.).

EXAMPLE 28

Polymerization of Ethylene Using Complex 2c
[Polymerization of Ethylene]

In an inert gas atmosphere, a 100 ml pressure-resistant stainless steel vessel was charged with dry toluene (36.5 ml), and then a solution (10 ml, 100 μmol) of complex 2c (10 mmol/liter) in toluene was added. A solution of methylaluminoxane in toluene ("PMAO-S" available from TOSOH-FINECHEM Corp.; conc. 2.85 mol/liter, 3.5 ml, 10 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 30 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 0.27 g (activity: 2.7 g/mmol) (Tm: 87.8° C.).

EXAMPLE 29

Polymerization of Ethylene
[Preparation of Complex Solution]

In an argon atmosphere, a Schlenk flask was charged with bis(1,5-cyclooctadiene)nickel(0) (0.567 g, 2.06 mmol), and then dry diethyl ether (20 ml) was added to prepare a suspension of bis(1,5-cyclooctadiene)nickel(0). A solution of 2-isopropylphenylisocyanide (1.20 g, 8.26 mmol) in diethyl ether (10 ml) was dropwise added over a period of 5 minutes. The reaction liquid was changed to a red uniform solution and thereafter changed to a yellow suspension. After reaction was carried out for 1 hour, a supernatant was removed, and a precipitate was dissolved in benzene. The thus-obtained solution was filtered, and the filtrate was evaporated to dryness under vacuum. The solid reaction product was dissolved in dry benzene (30 ml), and MeI (0.64 ml, 10.30 mmol) was added. The mixture was allowed to react under reflux for 24 hours. After completion of the reaction, the reaction liquid was cooled to room temperature and filtered. The filtrate was evaporated to dryness under vacuum to give a black solid in a yield of 1.43 g.

In an argon atmosphere, a Schlenk flask was charged with the above black solid (0.36 g, 0.46 mmol), and then dry toluene (46 ml) was added to dissolve the black solid therein.

[Polymerization of Ethylene]

In an inert gas atmosphere, a 100 ml pressure-resistant stainless steel vessel was charged with dry toluene (36.5 ml), and then the above-mentioned black solid complex solution (1 ml, 10 µmol) was added. Then a solution of methylaluminoxane in toluene ("PMAO-S" available from TOSOH-FINECHEM Corp.; conc. 2.85 mol/liter, 0.35 ml, 1 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 20 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 1.26 g (activity: 126 g/mmol) (Tm: 122.7° C., Mw: 12,000, Mw/Mn: 5.1).

EXAMPLE 30

Polymerization of Ethylene

[Preparation of Complex Solution]

In an argon atmosphere, a Schlenk flask was charged with bis(1,5-cyclooctadiene)nickel(0) (0.617 g, 2.24 mmol), and then dry diethyl ether (20 ml) was added to prepare a suspension of bis(1,5-cyclooctadiene)nickel(0). A solution of 2-methyl-6-isopropylphenylisocyanide (1.43 g. 8.96 mmol) in diethyl ether (10 ml) was dropwise added over a period of 5 minutes. The reaction liquid was changed to a red uniform solution and thereafter changed to a yellow suspension. After reaction was carried out for 1 hour, a supernatant was removed, and a precipitate was dissolved in benzene. The thus-obtained solution was filtered, and the filtrate was evaporated to dryness under vacuum. The solid reaction product was dissolved in dry benzene (30 ml), and MeI (0.64 ml, 10.30 mmol) was added. The mixture was allowed to react under reflux for 24 hours. After completion of the reaction, the reaction liquid was cooled to room temperature and filtered. The filtrate was evaporated to dryness under vacuum to give a black solid in a yield of 1.93 g.

In an argon atmosphere, a Schlenk flask was charged with the above black solid (0.79 g, 0.95 mmol), and then dry toluene (95 ml) was added to dissolve the black solid therein.

[Polymerization of Ethylene]

In an inert gas atmosphere, a 100 ml pressure-resistant stainless steel vessel was charged with dry toluene (36.5 ml), and then the above-mentioned black solid complex solution (1 ml, 10 µmol) was added. Then a solution of methylaluminoxane in toluene ("PMAO-S" available from TOSOH-FINECHEM Corp.; conc. 2.85 mol/liter, 0.35 ml, 1 mmol) was added, and the mixture was stirred for 30 minutes. Then ethylene was blown into the pressure-resistant vessel in an amount such that the partial pressure of ethylene reached 0.8 MPa, to initiate polymerization. Polymerization was carried out for 20 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give polyethylene in a yield of 0.18 g (activity: 18 g/mmol) (Tm: 121.7° C., Mw: 950,000, Mw/Mn: 3.4).

EXAMPLE 31

Polymerization of Ethylene Using Complex 5a

[Polymerization of Ethylene]

In an Inert gas atmosphere, a 100 ml pressure-resistant stainless steel vessel was charged with dry toluene (36.5 ml) and a solution (10 ml, 100 µmol) of complex 5a (10 mmol/liter) in toluene. Then a solution of tris(pentafluorophenyl)borane in hydrocarbon ($(C_6F_5)_3$B/Isopar-E, available from TOSOH-FINECHEM Corp., 0.079 mol/liter, 2.52 ml, 200 µmol) was added to the complex 5a solution. The mixture was stirred for 30 minutes. Then a solution of methylaluminoxane in toluene ("PMAO-S" available from TOSOH-FINECHEM Corp.; conc. 2.85 mol/liter, 0.35 ml, 1 mmol) was added, and the mixture was stirred for 30 minutes. Then ethylene was blown into the pressure-resistant vessel in an amount such that the partial pressure of ethylene reached 1.0 MPa, to initiate polymerization. Polymerization was carried out for 30 minutes. Unreacted ethylene was removed, and methanol (5 ml) was added to stop the polymerization. The polymerization liquid was poured in 10% hydrochloric acid-added methanol (300 ml) to precipitate a polymer. The polymer-containing liquid was filtered and the solid was dried under vacuum to give waxy polyethylene in a yield of 0.18 g (activity: 1.8 g/mmol) (Tm: 47.0° C., Mw: 665, Mw/Mn: 1.9).

EXAMPLE 32

Polymerization of Ethylene

[Preparation of Catalyst Solution]

In an inert gas atmosphere, complex 7 (28 mg) was dissolved in dry toluene (495 ml), and then, a solution of methylaluminoxane in toluene ("PMAO-S" available from TOSOH-FINECHEM Corp.; conc. 2.85 mol/liter, 4.39 ml, 12.5 mmol) was added, and the mixture was stirred for 30 minutes to prepare a catalyst solution.

[Polymerization of Ethylene]

In an inert gas atmosphere, the above-mentioned catalyst solution was placed in a 2,000 ml pressure-resistant stainless steel vessel, and the temperature was maintained at 30° C. Then ethylene was blown into the pressure-resistant vessel in an amount such that the partial pressure of ethylene reached 1.0 MPa, to initiate polymerization. Polymerization was carried out for 60 minutes. Unreacted ethylene was removed, and methanol (5 ml) was added to stop the polymerization. The solvent was removed under vacuum from the polymerization liquid, and the polymerization liquid was poured in 10% hydrochloric acid-added methanol (300 ml) to precipitate a polymer. The polymer-containing liquid was filtered and the solid was dried under vacuum to give polyethylene in a yield of 10.5 g (Tm: 138.7° C.).

EXAMPLE 33

Polymerization of Ethylene
[Preparation of Catalyst Solution]
In an inert gas atmosphere, complex 8 (30.3 mg, 50 μmol) was dissolved in dry toluene (495 ml), and then, a solution of methylaluminoxane in toluene ("PMAO-S" available from TOSOH-FINECHEM Corp.; conc. 2.85 mol/liter, 4.39 ml, 12.5 mmol) was added, and the mixture was stirred for 30 minutes to prepare a catalyst solution.
[Polymerization of Ethylene]
In an inert gas atmosphere, the above-mentioned catalyst solution was placed in a 2,000 ml pressure-resistant stainless steel vessel, and the temperature was maintained at 30° C. Then ethylene was blown into the pressure-resistant vessel in an amount such that the partial pressure of ethylene reached 1.0 MPa, to initiate polymerization. Polymerization was carried out for 60 minutes. Unreacted ethylene was removed, and methanol (5 ml) was added to stop the polymerization. The solvent was removed under vacuum from the polymerization liquid, and the polymerization liquid was poured in 10% hydrochloric acid-added methanol (300 ml) to precipitate a polymer. The polymer-containing liquid was filtered and the solid was dried under vacuum to give polyethylene in a yield of 19.34 g (Tm: 139.2° C.).

EXAMPLE 34

Polymerization of Ethylene Using Complex 10
[Polymerization of ethylene]
In an inert gas atmosphere, a 100 ml pressure-resistant stainless steel vessel was charged With dry toluene (21.4 ml) and a solution (10 ml, 100 μmol) of complex 10 (10 mmol/liter) in toluene. Then a solution of tris(pentafluorophenyl)borane in hydrocarbon (($C_6F_5$)$_3$B/Isopar-E, available from TOSOH-FINECHEM Corp., 0.079 mol/liter, 5.1 ml, 400 μmol) was added to the complex 10 solution. The mixture was stirred for 30 minutes. Then a solution of methylaluminoxane in toluene ("PMAO-S" available from TOSOH-FINECHEM Corp.; conc. 2.85 mol/liter, 3.5 ml. 10 mmol) was added, and the mixture was stirred for 30 minutes. Then ethylene was blown into the pressure-resistant vessel in an amount such that the partial pressure of ethylene reached 0.8 MPa,to initiate polymerization. Polymerization was carried out for 30 minutes. Unreacted ethylene was removed, and methanol (5 ml) was added to stop the polymerization. The polymerization liquid was poured in water (300 ml). The organic phase was separated and dried over sodium sulfate. Then the solvent was removed by distillation to give viscous oil in a yield of 0.31 g.

The results of polymerization in Examples 26 to 34 are shown in Table 9, and chemical structures of the compounds used in these examples are shown in Table 10

As seen from the examples, a catalyst for polymerization of an olefin, which comprises the transition metal compound of the present invention, exhibits an improved activity for polymerization of an olefin. Thus, industrially useful polyolefin can be efficiently produced by using the catalyst.

TABLE 9

| Example No. | Ex. 26 | Ex. 27 | Ex. 28 | Ex. 29 | Ex. 30 | Ex. 31 | Ex. 32 | Ex. 33 | Ex. 34 |
| --- | --- | --- | --- | --- | --- | --- | --- | --- | --- |
| Tran. metal cpd*1 | 2a | 2b | 2c | Ni-CN-iPr MeI | Ni-CN-Me iPr-MeI | 5a | 7 | 8 | 10 |
| Amount (μmol) | 10 | 10 | 100 | 10 | 10 | 100 | 50 | 50 | 100 |
| Acti. cocata.*2 | PMAO | PMAO | PMAO | PMAO | PMAO | PMAO | PMAO | PMAO | PMAO |
| Amount (mmol) | 1 | 1 | 10 | 1 | 1 | 10 | 12.5 | 12.5 | 10 |
| Addive | — | — | — | — | — | B($C_6F_5$)$_3$ | — | — | B($C_6F_5$)$_3$ |
| Amount (μmol) | — | — | — | — | — | 400 | — | — | 400 |
| Ethylene pressure (MPa) | 0.8 | 0.8 | 0.8 | 0.8 | 0.8 | 0.8 | 1.0 | 1.0 | 0.8 |
| Polymn. time (min) | 30 | 30 | 30 | 30 | 30 | 30 | 60 | 60 | 30 |
| Polymn. temp. (° C.)*3 | r.t. | r.t. | r.t. | r.t. | r.t. | r.t. | 30 | 30 | r.t. |
| Polymer yield (g) | 0.25 | 0.60 | 0.27 | 1.26 | 0.18 | 0.47 | 10.5 | 19.34 | 0.31 |
| Activity (g/mmol) | 25 | 60 | 2.7 | 126 | 18 | 4.7 | 210 | 386.8 | 3.1 |
| Melting point (° C.) | 128.0 | 116.0 | 87.8 | 122.7 | 121.7 | 47 | 138.7 | 139.2 | — |
| Mn × $10^3$ | 100 | — | — | 2.4 | 280 | 0.35 | — | — | — |
| Mw × $10^3$ | 330 | — | — | 12 | 950 | 0.665 | — | — | — |
| Mw/Mn | 3.3 | — | — | 5.1 | 3.4 | 1.9 | — | — | — |

Note,
*1 Transition metal compound;
Ni- = Ni(cod)$_2$
CN-iPr = 4 equiv. CN-(2-iPr-$C_6H_4$)
CN-Me-iPr = 4 equiv. CN-(2-Me-6-iPr-$C_6H_3$)
*2 Activating cocatalyst
*3 Polymerization temperature: r.t. = room temperature

TABLE 10

| Example | compound |
|---|---|
| 26 | 2a |
| 27 | 2b |
| 28 | 2c |

TABLE 10-continued

| Example | compound |
|---|---|
| 31 | 5a |
| 32 | 7 |
| 33 | 8 |
| 34 | 10 |

What is claimed is:
1. A transition metal compound represented by the following general formula (1):

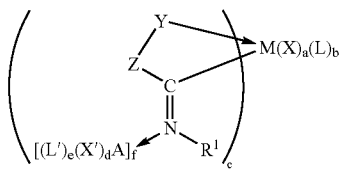

wherein $R^1$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom;

Z represents a substituent selected from the group consisting of substituents represented by the following formulae (2):

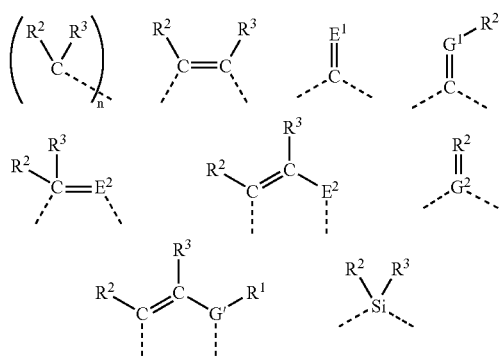

wherein R', $R^2$ and $R^3$ independently represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom, R', $R^2$ and $R^3$ may be the same or different, and two members selected from R', $R^2$ and $R^3$ may be bonded together to form a ring, provided that at least two rings can be formed; $E^1$ and $E^2$ represent an atom of Group 16 of the Periodic Table, G', $G^1$ and $G^2$ represent an atom of Group 15 of the Periodic Table, n is an integer of 0 to 2 provided that a case when n is 0 means that Y and the iminoacyl group in formula (1) are directly bonded to each other;

Y represents a substituent selected from the group consisting of substituents represented by the following formulae (3),

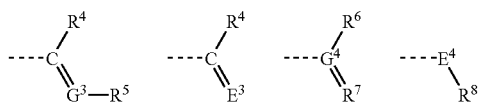

wherein $R^4$, $R^7$ and $R^8$ independently represents a hydrogen atom, a hydrocarbon group having 1 to 20 carbon atoms, a substituted silyl group, a substituted amide group, a substituted, alkoxy group, a substituted aryloxy group, or a hydrocarbon group containing a substituted silyl group, an atom of Group 15 or Group 16 of the Periodic Table or a halogen atom, $R^5$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom, $R^6$ represents a hydrocarbon group having 1 to 20 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom, $E^3$ and $E^4$ represent an atom of Group 16 of the Periodic Table, $G^3$ and $G^4$ represent an atom of Group 15 of the Periodic Table, $R^4$ and $R^5$ may be bonded together to form a ring, and $R^6$ and $R^7$ may be bonded together to form a ring;

two members selected from $R^1$, Z and Y may be bonded together to form a ring, provided that at least two rings can be formed; A represents a transition metal atom of Groups 3 to 11 of the Periodic Table or a typical element of Groups 1, 2 and 11 to 16 of the Periodic Table;

X' represents a hydrogen atom, a hydrocarbon group having 1 to 20 carbon atoms, a substituted silyl group, a substituted amide group, a substituted alkoxy group, a substituted aryloxy group, a hydrocarbon group containing a substituted silyl group, or a hydrocarbon group containing an atom of Group 15 or Group 16 of the Periodic Table or a halogen atom, or X' is a halogen atom; and d is an integer of 0 to 6 and, when n is at least 2, X's may be the same or different;

L' is a coordinate bond-forming compound having a coordinating member selected from the group consisting of a electron, atoms of Groups 14, 15 and 16 of the Periodic Table and halogen atoms, and e is an integer of 0 to 6 and, when e is at least 2, L's may be the same or different;

d is an oxidation number of the central metal A, and f is an integer of 0 or 1;

M represents a transition metal atom of Groups 3 to 11 of the Periodic Table;

X represents a hydrogen atom, a hydrocarbon group having 1 to 20 carbon atoms, a substituted silyl group, a substituted amide group, a substituted alkoxy group, a substituted aryloxy group, a hydrocarbon group containing a substituted silyl group, or a hydrocarbon group containing an atom of Group 15 or Group 16 of the Periodic Table or a halogen atom, or X is a halogen atom; and a is an integer of 1 to 5 and, when a is at least 2, Xs may be the same or different:

L is a coordinate bond-forming compound having a coordinating member selected from the group consisting of π electron, atoms of Groups 14, 15 and 16 of the Periodic Table and halogen atoms, and b is an integer of 0 to 6 and, when b is at least 2, Ls may be the same or different; and X and L may be bonded to each other, L and $R^1$ may be bonded to each other, and L grid Y may be bonded to each other; and c is an integer of 1 to 5 and the sum of a+c is an oxidation number of the central metal M.

2. A transition metal compound represented by the following general formula (4):

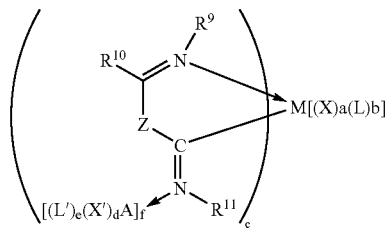

wherein $R^9$ and $R^{11}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom; $R^{10}$ represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of Group 15 or group 16 of the Periodic Table or a halogen atom; Z, M, X, L, A, X', L', a, b, c, a, e and f are the same as Z, M, X, L, A, X', L', a, b, c, d, e and f, which are defined for formula (1); two members selected from the group consisting of $R^9$, $R^{10}$, $R^{11}$ and Z are optionally bonded to each other to form a ring, provided that at least two rings can be formed, X and L are optionally bonded to each other, L and $R^9$ are optionally bonded to each other, and L and $R^{11}$ are optionally bonded to each other.

3. A transition metal compound represented by the following formula (5):

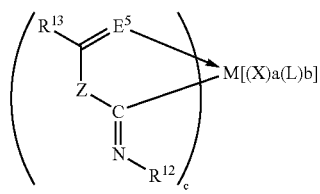

wherein $R^{12}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom; $R^{13}$ represents a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom;

$E^5$ represents an atom of Group 16 of the Periodic Table of the periodic table; Z, M, X, L, a, b and c are the same as Z, M, X, L, a, b and c, respectively, which are defined for formula (1); two members selected from the group $R^{12}$, $R^{13}$ and Z are optionally bonded to each other to form a ring, provided that at least two rings can be formed; X and L are optionally bonded to each other, and L and $R^{12}$ are optionally bonded to each other.

4. A transition metal compound represented by the following general formula (6):

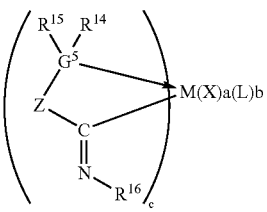

wherein $R^{14}$ and $R^{15}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom, $R^{14}$ and $R^{15}$ may be the same or different, and $R^{14}$ and $R^{15}$ are optionally bonded together to form a ring; $R^{16}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom; $G^5$ represents an atom of Group 15 of the Periodic Table; Z, M, X, L, a, b and c are the same as Z, M, X, L, a, b and c, respectively, which are defined for formula (1); two members selected from the group consisting of $R^{14}$, $R^{15}$, $R^{16}$ and Z are optionally bonded together to form a ring, provided that at least two rings can be formed; X and L are optionally bonded to each other, L and $R^{14}$ may be bonded to each other, L and $R^{15}$ are optionally bonded to each other, and L and $R^{16}$ are optionally bonded to each other.

5. A transition metal compound represented by the following general formula (7):

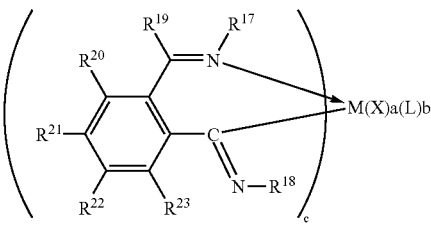

wherein $R^{17}$ and $R^{18}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom, and $R^{17}$ and $R^{18}$ are the same or different; $R^{19}$ through $R^{23}$ represent a hydrogen atom, a halogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom, $R^{19}$ through $R^{23}$ are optionally the same or different, and two members selected from $R^{17}$ through $R^{23}$ are optionally bonded together to form a ring, provided that at least two rings can be formed; M, X, L, a, b and c are the same as M, X, L, a, b and c, respectively, which are defined for formula (1): and X and L are optionally bonded to each other, L and $R^{17}$ are optionally bonded to each other, and L and $R^{18}$ are optionally bonded to each other.

6. A transition metal compound represented by the following general formula (8):

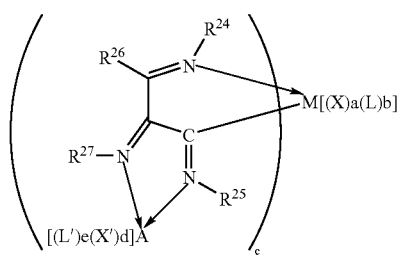

wherein $R^{24}$ through $R^{27}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom; and M, X, L, A, X', L', a, b, c, d and e are the same as M, X, L, A, X', L', a, b, c, d and e, respectively, which are defined for formula (1).

7. A transition metal compound represented by the following general formula (9):

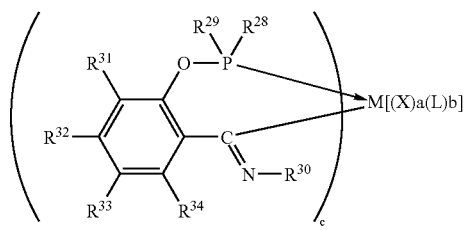

wherein $R^{28}$, $R^{29}$ and $R^{31}$ through $R^{34}$ represent a hydrogen atom, a hydrocarbon group having 1 to 20 carbon atoms, a substituted silyl group, a substituted amide group, a substituted alkoxy group, a substituted aryloxy group, or a substituent containing a substituted silyl group, an atom of Group 15 or Group 16 of the Periodic Table or a halogen atom; $R^{30}$ represents a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom, M, X, L, a, b and c are the same as M, X, L, a, b and c, respectively, which are defined for formula (1); and X and L are optionally bonded to each other, L and $R^{28}$ are optionally bonded to each other, L and $R^{29}$ are optionally bonded to each other, and L and $R^{30}$ are optionally bonded to each other.

8. A catalyst for polymerization of an olefin, which comprises (A) a transition metal compound as claimed in any one of claims 1 to 7, and (B) an activating cocatalyst.

9. A catalyst for polymerization of an olefin, which comprises (A) a transition metal compound and (B) an activating cocatalyst; said transition metal compound (A) being represented by the following general formula (10):

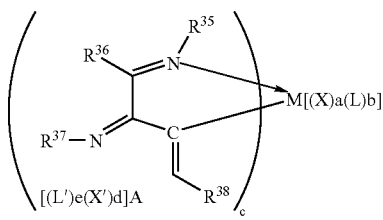

wherein $R^{35}$ through $R^{38}$ represent a hydrogen atom, a hydrocarbon group having 1 to 30 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom; and M, X, L, a, b and c are the same as M, X, L, a, b and c, respectively, which are defined for formula (1).

10. A catalyst for polymerization of an olefin, which comprises (A) a transition metal compound and (B) an activating cocatalyst; said transition metal compound (A) being represented by the following general formula (11):

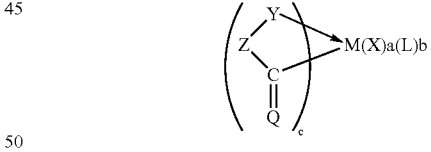

wherein Q represents an element of Group 16 of the Periodic table or $C(R^{39})(R^{40})$ wherein $R^{39}$ and $R^{40}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom; Z, Y, M, X, L, a, b and c are the same as Z, Y, M, X, L, a, b and c, respectively, which are defined for formula (1); and two members selected from the group consisting of Q, Z and Y are optionally bonded together to form a ring, provided that at least two rings can be formed; X and L may be bonded to each other, and L and Y are optionally bonded to each other.

11. A catalyst for polymerization of an olefin, which comprises (A) a transition metal compound and (B) an activating cocatalyst; said transition metal compound (A) being represented by the following general formula (12):

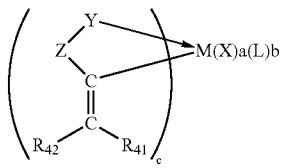

wherein $R^{41}$ and $R^{42}$ represent a hydrogen atom, a hydrocarbon group having 1 to 20 carbon atoms, a substituted silyl group, a substituted amide group, a substituted alkoxy group, a substituted aryloxy group, or a hydrocarbon group containing a substituted silyl group, an atom of Group 15 or Group 16 of the Periodic Table or a halogen atom, and $R^{41}$ and $R^{42}$ are optionally the same or different;

Z, Y, M, X, L, a, b and c are the same as Z, Y, M, X, L, a, b and c, respectively, which are defined for formula (1); and two members selected from the group consisting of $R^{41}$, $R^{42}$, Z and Y are optionally bonded together to form a ring, provided that at least two rings can be formed; X and L are optionally bonded to each other, L and $R^{41}$ are optionally bonded to each other, L and $R^{42}$ are optionally bonded to each other, and L and Y are optionally bonded to each other.

12. A catalyst for polymerization of an olefin, which comprises (A) a transition metal compound and (B) an activating cocatalyst; said transition metal compound (A) being represented by the following general formula (13):

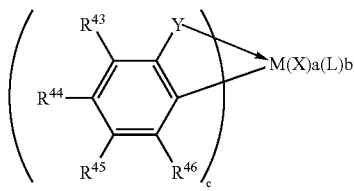

wherein $R^{43}$ through $R^{46}$ represent a hydrogen atom, a hydrocarbon group having 1 to 20 carbon atoms, a substituted silyl group, a substituted amide group, a substituted alkoxy group, a substituted aryloxy group, a halogen atom, or a substituent containing an atom of Group 15 or Group 16 of the Periodic Table, and $R^{43}$ through $R^{46}$ may be the same or different;

Y, M, X, L, a, b and c are the same as Y, M, X, L, a, b and c, respectively, which are defined for formula (1); and two members selected from the group consisting of Y and $R^{43}$ through $R^{46}$ are optionally bonded together to form a ring, provided that at least two rings can be formed; X and L are optionally bonded to each other, L and $R^{46}$ are optionally bonded to each other, and L and Y are optionally bonded to each other.

13. A catalyst for polymerization of an olefin, which comprises (A) a transition metal compound and (H) an activating cocatalyst; said transition metal compound (A) being represented by the following general formula (14):

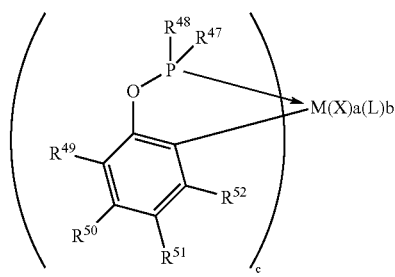

wherein $R^{47}$ through $R^{52}$ represent a hydrogen atom, a hydrocarbon group having 1 to 20 carbon atoms, a substituted silyl group, a substituted amide group, a substituted alkoxy group, a substituted aryloxy group, a halogen atom, or a substituent containing an atom of Group 15 or Group 16 of the Periodic Table, and $R^{47}$ through $R^{52}$ are optionally the same or different;

M, X, L, a, b and c are the same as M, X, L, a, b and c, respectively, which are defined for formula (1); and two members selected from the group consisting of $R^{47}$ through $R^{52}$ are optionally bonded together to form a ring, provided that at least two rings can be formed; X and L are optionally bonded to each other, L and $R^{47}$ are optionally bonded to each other, L and $R^{48}$ are optionally bonded to each other, and L and $R^{52}$ are optionally bonded to each other.

14. A catalyst for polymerization of an olefin, which comprises (A) a transition metal compound as claimed in any one of claims 1 to 7, (B) an activating cocatalyst, and (C) an organometallic compound.

15. A catalyst for polymerization of an olefin, which comprises a catalyst as claimed in any one of claims 9 to 13, and (C) an organometallic compound.

16. A process for polymerizing an olefin, which comprises polymerizing an olefin in the presence of a catalyst comprising (A) a transition metal compound as claimed in claim 1, and (B) an activating cocatalyst.

17. A process for polymerizing an olefin, which comprises polymerizing an olefin in the presence of a catalyst comprising (A) a transition metal compound as claimed in claim 1, (B) an activating cocatalyst, and (C) an organometallic compound.

* * * * *

UNITED STATES PATENT AND TRADEMARK OFFICE
CERTIFICATE OF CORRECTION

PATENT NO. : 7,153,916 B2 Page 1 of 1
APPLICATION NO. : 10/094799
DATED : December 26, 2006
INVENTOR(S) : Masao Tanabiki et al.

It is certified that error appears in the above-identified patent and that said Letters Patent is hereby corrected as shown below:

Column 145, formulae (2),

"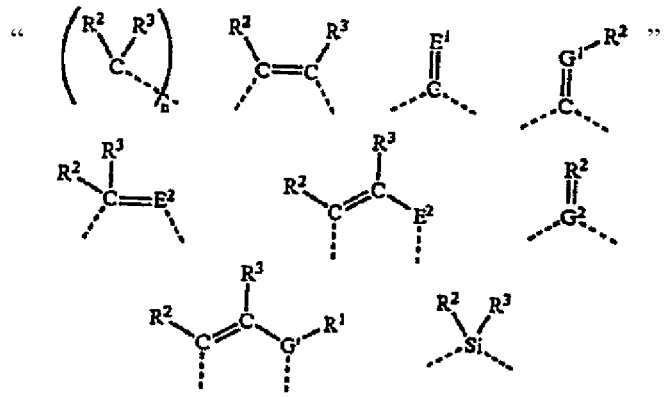"

should read

--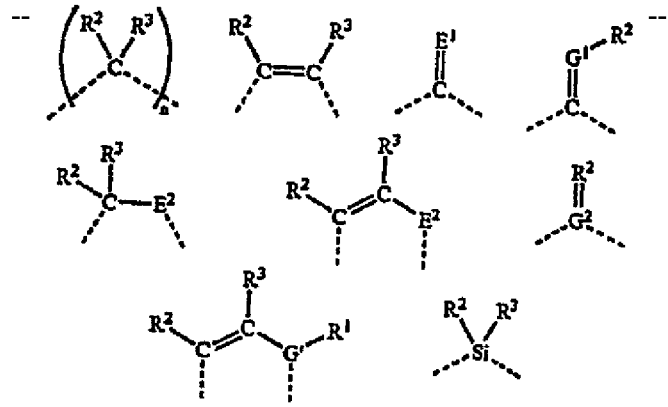--.

Signed and Sealed this

Eleventh Day of September, 2007

JON W. DUDAS
*Director of the United States Patent and Trademark Office*